United States Patent
Afonso et al.

(10) Patent No.: US 6,214,827 B1
(45) Date of Patent: Apr. 10, 2001

(54) TRICYCLIC COMPOUNDS USEFUL FOR INHIBITION OF G-PROTEIN FUNCTION AND FOR TREATMENT OF PROLIFERATIVE DISEASES

(75) Inventors: Adriano Afonso, West Caldwell, NJ (US); John J. Baldwin, Gwynedd Valley, PA (US); Ronald J. Doll, Maplewood, NJ (US); Ge Li, Franklin Park, NJ (US); Alan K. Mallams, Long Valley, NJ (US); F. George Njoroge, Union, NJ (US); Dinanath F. Rane, Morganville, NJ (US); John C. Reader, Princeton, NJ (US); Randall R. Rossman, Nutley, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/108,124

(22) Filed: Jun. 23, 1998

Related U.S. Application Data

(63) Continuation of application No. 08/713,324, filed on Sep. 13, 1996, now Pat. No. 5,801,175, which is a continuation-in-part of application No. 08/418,323, filed on Apr. 7, 1995, now abandoned.

(30) Foreign Application Priority Data

Apr. 3, 1996 (WO) .................................. PCT/US96/04172

(51) Int. Cl.[7] ...................... A61K 31/495; A61K 31/445; A61P 35/00; C07D 401/00; C07D 241/02
(52) U.S. Cl. ............................... 514/252.13; 514/253.03; 514/254.11; 514/255.01; 514/255.03; 514/318; 514/320; 514/324; 514/325; 544/361; 544/375; 544/381; 546/80; 546/89; 546/196; 546/202; 546/203
(58) Field of Search ..................................... 514/318, 320, 514/324, 325, 252.13, 253.03, 254.11, 255.01, 255.03; 544/361, 375, 381; 546/80, 89, 196, 202, 203

(56) References Cited

U.S. PATENT DOCUMENTS

| | | | |
|---|---|---|---|
| 3,326,924 | 6/1967 | Villani | 260/293 |
| 4,144,337 | 3/1979 | Bastian | 424/250 |
| 4,282,233 | 8/1981 | Villani | 424/267 |
| 4,470,972 | 9/1984 | Gold et al. | 424/177 |
| 4,826,853 | 5/1989 | Piwinski et al. | 514/290 |
| 4,831,042 | 5/1989 | Villani | 514/316 |
| 4,863,931 | 9/1989 | Schumacher et al. | 514/290 |
| 5,089,496 | 2/1992 | Piwinski et al. | 514/253 |
| 5,104,876 | 4/1992 | Piwinski et al. | 514/254 |
| 5,141,851 | 8/1992 | Brown et al. | 435/15 |
| 5,151,423 | 9/1992 | Piwinski et al. | 514/254 |
| 5,185,248 | 2/1993 | Barbacid et al. | 435/15 |
| 5,204,348 | 4/1993 | Fukazawa et al. | 514/253 |
| 5,393,890 | 2/1995 | Syojii et al. | 546/80 |
| 5,405,843 | 4/1995 | Fukazawa et al. | 514/183 |
| 5,801,175 | * 9/1998 | Afonso et al. | 514/254 |
| 5,883,096 | * 3/1999 | Lowe et al. | 514/252 |

FOREIGN PATENT DOCUMENTS

| | | |
|---|---|---|
| 4243496 | 3/1994 | (DE) . |
| 0042544 | 12/1981 | (EP) . |
| 0270818 | 6/1988 | (EP) . |
| 0347123 | 12/1989 | (EP) . |
| 0363212 | 11/1990 | (EP) . |
| 0396083 | 11/1990 | (EP) . |
| 0495484 | 7/1992 | (EP) . |
| 0556813 | 2/1993 | (EP) . |
| 0535730 | 4/1993 | (EP) . |
| 682015 | 11/1995 | (EP) . |
| 710661 | 5/1996 | (EP) . |
| WO 88/03138 | 5/1988 | (WO) . |
| WO 89/10363 | 11/1989 | (WO) . |
| WO 89/10369 | 11/1989 | (WO) . |
| WO 90/13548 | 11/1990 | (WO) . |
| WO 92/00293 | 1/1992 | (WO) . |
| WO 92/06970 | 4/1992 | (WO) . |
| WO 92/11034 | 7/1992 | (WO) . |
| WO 92/20681 | 11/1992 | (WO) . |
| WO 93/02081 | 2/1993 | (WO) . |
| WO 94/04561 | 3/1994 | (WO) . |
| WO 94/05693 | 3/1994 | (WO) . |
| WO 94/08051 | 4/1994 | (WO) . |

(List continued on next page.)

OTHER PUBLICATIONS

*Cell*, 65, 1–4 (1991).
*J. Biol. Chem.*, 266, (24) 15575–15578 (1991).
*Nature*, 356, 713–715 (1992).

(List continued on next page.)

*Primary Examiner*—Mukund J. Shah
*Assistant Examiner*—Brenda Coleman
(74) *Attorney, Agent, or Firm*—Margaret M. Albanese; Henry C. Jeanette

(57) ABSTRACT

Novel compounds of Formula

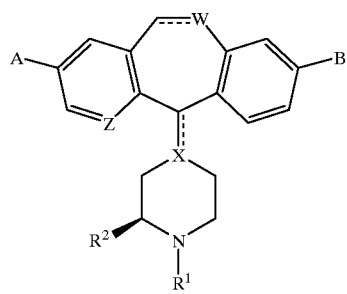

are disclosed. Also disclosed is a method of inhibiting Ras function and therefore inhibiting the abnormal growth of cells. The method comprises administering a compound of the above formula to a biological system. In particular, the method inhibits the abnormal growth of cells in a mammal such as a human being.

8 Claims, No Drawings

FOREIGN PATENT DOCUMENTS

| | | |
|---|---|---|
| WO 94/24107 | 10/1994 | (WO) . |
| WO 95/00497 | 1/1995 | (WO) . |
| WO 95/10514 | 4/1995 | (WO) . |
| WO 95/10515 * | 4/1995 | (WO) . |
| WO 95/10516 | 4/1995 | (WO) . |
| WO 95/15949 | 6/1995 | (WO) . |

OTHER PUBLICATIONS

*Proc. Natl. Acad. Sci. USA*, 87, 3042–3046 (1990).
*Proc. Natl. Acad. Sci. USA*, 87, 7541–7545 (1990).
*Proc. Natl. Acad. Sci. USA*, 88, 8631–8635 (1991).
*Biochemistry*, 31, 3800–3807, (1992).
*Cell*, 62, 81–88 (1990).
*J. Biol. Chem.*, 265, (25) 14701–14704 (1990).
*Proc. Natl. Acad. Sci. USA*, 87, 7926–7929 (1990).
*Science*, 260 (1993), 1937–1942.
Chem. Abstracts No. 121:53129x (1994) for WO 94/04561.
Masci, *J. Chem. Soc. Chem. Commun.*, 1262–1263 (1982).
Masci, *J. Org. Chem.*, 50, 4081–4087 (1985).
Piwinski et al., *J. Med. Chem.*, 34, (1) 457–461 (1991).
Sebti et al., *Proc. Ann. Meeting AM Assoc. Cancer Res.*, 33:A2217 (1992).
Villani et al., *J. Med. Chem.*, 15, (7) 750–754 (1972).
Billah et al., *Lipids*, 26, (12) 1172–1174 (1991).
Furth et al., *J. Virology*, 43, 294–304 (1982).
Omer et al., *Biochemistry*, 32, 5167–5176 (1993).
Price et al., *Proc. Natl. Acad. Sci. USA*, 84, 156–160 (1987).
Villani et al., *Arzneim.–Forsch./Drug Res.*, 36(II), 1311–1314 (1986).
Yokoyama et al., *Proc. Natl. Acad. Sci. USA*, 88, 5302–5306 (1991).
*Advanced Organic Chemistry*, 3rd ed., Part B: Reactions and Synthesis (1990), 571–573.*
*Chemical Abstracts*, 121 (1994) 301326v, abstract for DN.*
Graham, *Exp. Opin. Ther. Patents*, 5, 1269–1285 (1995).*
Khosravi–Far et al., *Cell Growth & Differentiation*, 3, 461–469 (1992).*
Sarges et al., *J. Med. Chem.*, 33, 1859–1865 (1990).*
Comins et al., *Tetrahedron Letters*, vol. 27, No. 38, pp. 4549–4552 (1986).
E.M. Smith et al., *J. Med. Chem.*, 32, pp. 1600–1606 (1989).
Gustavson, et al., *Synthetic Communications*, 21(2), pp. 265–270 (1991).
Kohl et al., *Science*, vol. 260, pp. 1934–1937 (1993).
Pavia et al., *J. Med. Chem.*, 33, pp. 854–861 (1990).
Pavia et al., *J. Med. Chem.*, 35, pp. 4238–4248 (1992).

* cited by examiner

TRICYCLIC COMPOUNDS USEFUL FOR INHIBITION OF G-PROTEIN FUNCTION AND FOR TREATMENT OF PROLIFERATIVE DISEASES

CROSS REFERENCE TO RELATED APPLICATIONS

This application is a continuation of application Ser. No. 08/713,324 filed on Sep. 13, 1996 (which is now U.S. Pat. No. 5,801,175) which is in turn is a continuation-in-part of application Ser. No. 08/418,323 filed on Apr. 7,1995, now abandoned, the disclosures of which are incorporated herein by reference thereto.

BACKGROUND

International Publication Number WO92/11034, published Jul. 9, 1992, discloses a method of increasing the sensitivity of a tumor to an antineoplastic agent, which tumor is resistant to the antineoplastic agent, by the concurrent administration of the antineoplastic agent and a potentiating agent of the formula:

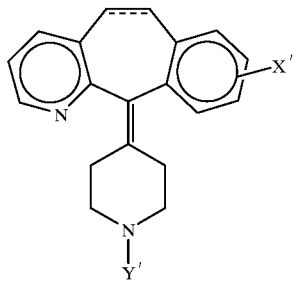

wherein Y' is hydrogen, substituted carboxylate or substituted sulfonyl. Examples of such potentiating agents include 11-(4-piperidylidene)-5H-benzo[5,6]cyclohepta[1,2-b]pyridines such as Loratadine.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of ras are frequently found in many human cancers, most notably in more than 50% of colon and pancreatic carcinomas (Kohl et al., Science, Vol. 260, 1834 to 1837, 1993).

A welcome contribution to the art would be compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

The compounds useful in the claimed methods are novel compounds represented by Formula (1.0)

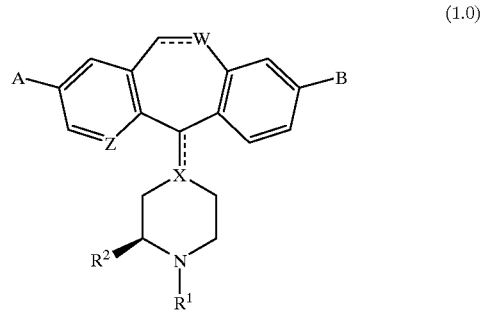

(1.0)

wherein:

—A and B are independently selected from H, halo or $C_1$–$C_6$ alkyl;

Z is N or CH;

W is CH, $CH_2$, O or S, wherein the dotted line to W represents a double bond which is present when W is CH;

X is C, CH or N, wherein the dotted line connecting X to the tricyclic ring system represents a double bond which is present when X is C;

$R^1$ is selected from:

1) a group of the formula:

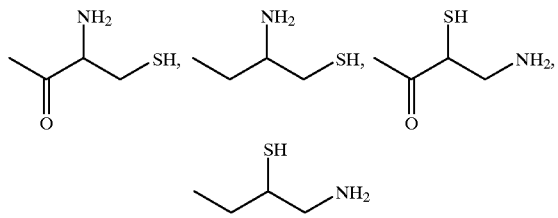

or disulfide dimers thereof;

2) a group of the formula:

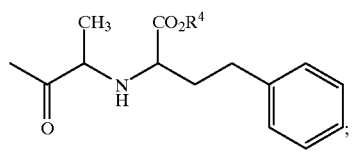

3) a group of the formula:

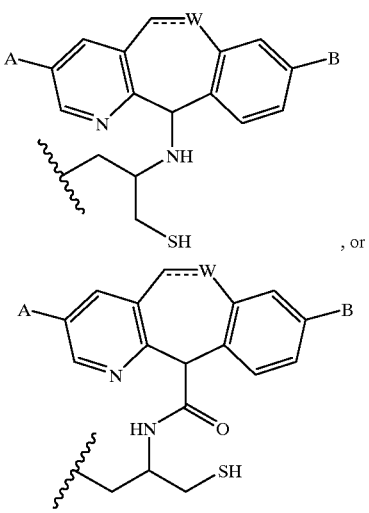

, or wherein W, A and B are as defined above;
4) a group of the formula:

(159.0)

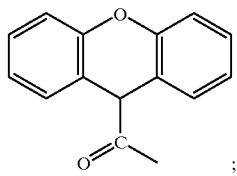

5) a group of the formula:

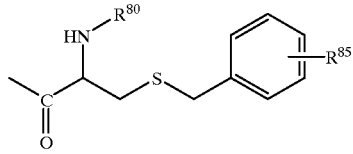

wherein $R^{80}$ is selected from H or —C(O)OR$^{90}$ wherein $R^{90}$ is a $C_1$–$C_6$ alkyl group (e.g., —C(CH$_3$)$_3$), and $R^{85}$ is a $C_1$–$C_6$ alkoxy group (e.g., p-OCH$_3$); and
6) a group of the formula:

(82.0)

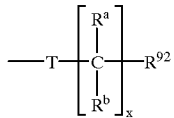

wherein:
(a) T is selected from:

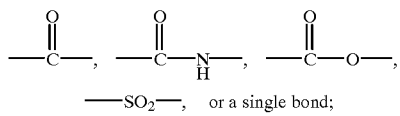

(b) x is 0, 1, 2, 3, 4, 5 or 6;

(c) each $R^a$ and each $R^{b\ is}$ independently selected from H, aryl, alkyl, alkoxy, aralkyl, amino, alkylamino, heterocyloalkyl, —COOR$^{60}$, —NH{C(O)}$_z$R$^{60}$ (wherein z is 0 or 1), or —(CH)$_w$S(O)$_m$R$^{60}$ (wherein w is 0, 1, 2 or 3, and m is 0, 1 or 2); or $R^a$ and $R^b$ taken together can represent cycloalkyl, =N—O-alkyl, =O or heterocycloalkyl; with the proviso that for the same carbon, $R^a$ is not selected from alkoxy, amino, alkylamino or —NH{C(O)}$_z$R$^{60}$ when $R^b$ is selected from alkoxy, amino, alkylamino or —NH{C(O)}$_z$R$^{60}$; and with the proviso that when T is a single bond, for the first carbon containing $R^a$ and $R^b$, $R^a$ and $R^b$ are not selected from alkoxy, alkylamino, amino or —NHR$^{60}$ (i.e., —NH{C(O)}$_z$R$^{60}$ wherein z is 0) (i.e., $R^a$ and $R^b$ on the first carbon bound to T, when T is a single bond, are not alkoxy, alkylamino, amino or —NHR$^{60}$); and (d) $R^{92}$ can represent H, alkyl, aryl, aryloxy, arylthio, aralkoxy, aralkyl, heteroaryl or heterocycloalkyl;

$R^{60}$ represents H, alkyl, aryl or aralkyl;
$R^4$ is H or $C_1$–$C_6$ alkyl;
$R^2$ is selected from: H, —C(O)OR$^6$, —C(O)NR$^6$R$^7$, $C_1$–$C_8$ alkyl, $C_2$–$C_8$ alkenyl, $C_2$–$C_8$ alkynyl, substituted ($C_1$–$C_8$)alkyl, substituted ($C_2$–$C_8$)alkenyl, substituted ($C_2$–$C_8$)alkynyl, wherein said substituted groups have one or more substituents selected from:
1) aryl, arylalkyl, heteroarylalkyl, heteroaryl, heterocycloalkyl, B-substituted aryl, B-substituted arylalkyl, B-substituted heteroarylalkyl, B-substituted heteroaryl or B-substituted heterocycloalkyl, wherein B is selected from $C_1$–$C_4$ alkyl, —(CH$_2$)$_n$OR$^6$, —(CH$_2$)$_n$NR$^6$R$^7$ and halo;
2) $C_3$–$C_6$ cycloalkyl;
3) —OR$^6$;
4) —SH or —S(O)$_r$R$^6$;
5) —NR$^6$R$^7$;
6) —N(R$^6$)—C(O)R$^7$;
7) —N(R$^6$)—C(O)NR$^7$R$^{12}$;
8) —O—C(O)NR$^6$R$^7$;
9) —O—C(O)OR$^6$;
10) —SO$_2$NR$^6$R$^7$;
11) —N(R$^6$)—SO$_2$—R$^7$;
12) —C(O)NR$^6$R$^7$;
13) —C(O)OR$^6$; and
provided where $R^1$ is D, $R^2$ is not H or $C_1$–$C_8$ alkyl, and where $R^1$ is D and $R^2$ is substituted $C_1$–$C_8$ alkyl, the substituents on said alkyl group are not substituents 3), 4), 5), 9), or 13); D is —C(O)—CH$_2$—R$^5$, —C(O)—O—R$^5$ or —C(O)—NH—R$^5$, wherein $R^5$ is pyridyl, pyridyl N-oxide,

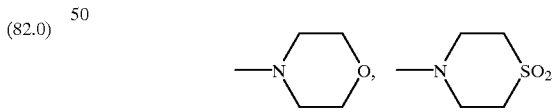

or a piperidinyl group of the formula

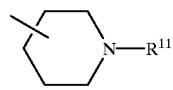

wherein $R^{11}$ represents H, $C_1$–$C_6$ alkyl, haloalkyl or —C(O)—R$^9$ wherein $R^9$ is $C_1$–$C_6$ alkyl, $C_1$–$C_6$ alkoxy or —NH(R$^{10}$) wherein $R^{10}$ is H or alkyl, or the group —C(O)—R$^9$ represents an acyl radical of a naturally occurring amino acid;

$R^6$, $R^7$ and $R^{12}$ are independently selected from H, $C_1$–$C_4$ alkyl, ($C_3$–$C_6$)cycloalkyl, aryl, arylalkyl (i.e., aralkyl), heteroaryl, heteroarylalkyl, heterocycloalkyl, substituted ($C_1$–$C_4$)alkyl, substituted ($C_3$–$C_6$)cycloalkyl, substituted aryl, substituted arylalkyl, substituted heteroaryl, substituted heteroarylalkyl or substituted heterocycloalkyl, wherein said substituted groups have one or more substituents (e.g., 1–3) selected from: $C_1$–$C_4$ alkoxy, aralkyl, heteroarylalkyl, —$NO_2$, $C_3$–$C_{10}$-alkoxyalkoxy (e.g.,—O—($C_1$–$C_4$)alkyl—O—($C_1$–$C_4$)alkyl), ($C_3$–$C_6$) cycloalkyl (e.g., cyclopropyl or cyclohexyl), aryl, —CN, nitrophenyl, methylenedioxyphenyl, heteroaryl, heterocycloalkyl, halo, —OH, —C(O)$R^{14}$, —C(O)$NR^6R^7$, —N($R^6$)C(O)$R^{14}$, —S(O)$_t R^{14}$ (e.g., —S—($C_1$–$C_4$)alkyl and —$SO_2 R^{14}$) or —$NR^{95}R^{15}$; provided that $R^6$, $R^7$ and $R^{12}$ are not —$CH_2$OH or —$CH_2 NR^{95}R^{15}$ when said $R^6$, $R^7$ or $R^{12}$ is directly bonded to a heteroatom, and further provided that $R^6$ is not H for groups 4) and 9), and $R^7$ is not H for group 6);

optionally, when $R^6$ and $R^7$ are bound to the same nitrogen, $R^6$ and $R^7$ together with the nitrogen to which they are bound, form a 5 to 7 membered heterocycloalkyl ring which optionally contains O, $NR^6$, or S(O)$_t$ wherein t is 0, 1 or 2;

optionally, when $R^7$ and $R^{12}$ are bound to the same nitrogen, $R^7$ and $R^{12}$ together with the nitrogen to which they are bound, form a 5 to 7 membered heterocycloalkyl ring which optionally contains O, $NR^6$, or S(O)$_t$ wherein t is 0, 1 or 2;

$R^{95}$ and $R^{15}$ are independently H, $C_1$–$C_4$ alkyl or aralkyl;

$R^{14}$ is $C_1$–$C_4$ alkyl, aryl or arylalkyl;

n=0, 1, 2, 3or 4; and t=0, 1 or 2;

or pharmaceutically acceptable salts thereof.

This invention also provides a method for inhibiting tumor growth by administering an effective amount of the tricyclic compounds, described herein, to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

The tricyclic compounds useful in the methods of this invention inhibit the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

All of the publications cited herein are hereby expressly incorporated in their entirety by reference.

As used herein, the following terms are used as defined below unless otherwise indicated:

"MS" represents Mass Spec;

"MH+" represents the molecular ion plus hydrogen of the molecule in the mass spectrum;

"Bu" represents butyl;

"Et" represents ethyl;

"Tr" represents trityl, (i.e., triphenylmethyl);

"Me" represents methyl;

"Ph" represents phenyl;

"BOC" represents t-butoxycarbonyl;

"FMOC" represents 9-fluorenylmethoxycarbonyl;

"alkyl" (including the alkyl portions of alkoxy, alkylamino and dialkylamino) represents straight and branched carbon chains and contains from one to twenty carbon atoms, preferably one to six carbon atoms; said alkyl group optionally being substitued with one, two or three groups independently selected from hydroxy, alkoxy, halo (e.g., —$CF_3$), amino, alkylamino, dialkylamino, N-acylalkylamino, N-alkyl-N-acylamino, or —S(O)$_m$-alkyl (wherein m is 0, 1 or 2), and wherein the alkyl portion of said optional groups are as defined above;

"alkenyl" represents straight and branched carbon chains having at least one carbon to carbon double bond and containing from 2 to 12 carbon atoms, preferably from 2 to 6 carbon atoms and most preferably from 3 to 6 carbon atoms;

"alkynyl" represents straight and branched carbon chains having at least one carbon to carbon triple bond and containing from 2 to 12 carbon atoms, preferably from 2 to 6 carbon atoms;

"aralkyl" represents an alkyl group, as defined above, wherein one or more hydrogen atoms of the alkyl moiety have been replaced by one or more aryl groups, as defined below (e.g., benzyl and diphenylmethyl);

"aryl" (including the aryl portion of aryloxy and aralkyl) represents a monocyclic, bicyclic or tricyclic carbocyclic group containing from 6 to 15 carbon atoms and comprising at least one aromatic ring, such as phenyl, naphthyl, phenanthryl, tetrahydronaphthyl or indanyl, with all available substitutable carbon atoms of the carbocyclic group being intended as possible points of attachment, said carbocyclic group being optionally substituted with one or more, preferably 1 to 3, substituents, independently selected from: (1) halo, (2) alkyl (e.g., $C_1$ to $C_6$ alkyl), (3) hydroxy, (4) alkoxy (e.g., $C_1$ to $C_6$ alkoxy), (5) —CN, (6) phenyl, (7) phenoxy, (8) —$CF_3$, (9) amino, (10) alkylamino, (11) dialkylamino, (12) aryl, (13) aralkoxy, (14) aryloxy, (15) —$S(O)_m$-aryl (wherein m is 0, 1, or 2), (16) —$COOR^{60}$ ($R^{60}$ is as defined above), (17) —$NO_2$, or (18) substituted $C_1$–$C_6$ alkyl wherein said alkyl group is substituted with 1, 2, or 3 groups independently selected from (a) amino, (b) alkylamino, (c) dialkylamino, (d) aryl, (e) N-acylalkyl-amino, (f) N-alkyl-N-acylamino, (g) N-aralkyl-N-acylamino, (h) hydroxy, (i) alkoxy, 0) halo (e.g., $CF_3$), or (k) heterocycloalkyl, provided that when there are two or more hydroxy, amino, alkylamino or dialkylamino substituents on the substituted $C_1$–$C_6$ alkyl group, the substituents are on different carbon atoms; or alternatively said aryl group may be fused through adjacent atoms to form a fused ring containing up to four carbon and/or heteroatoms (e.g., methylene dioxyphenyl, indanyl, tetralinyl, dihydrobenzofuranyl);

"aralkoxy"—represents an aralkyl group, as defined above, in which the alkyl moiety is covalently bonded to an adjacent structural element through an oxygen atom, for example, benzyloxy;

"aryloxy"—represents an aryl group, as defined above, covalently bonded to an adjacent structural element through an oxygen atom, for example, phenoxy;

"arylthio"—represents an aryl group, as defined above, covalently bonded to an adjacent structural element through a sulfur atom, for example, phenylthio;

"cycloalkyl" represents a saturated or unsaturated nonaromatic carbocyclic ring of from 3 to 8 carbon atoms, preferably 3 to 6 carbon atoms;

"halo" represents fluoro, chloro, bromo and iodo;

"heterocycloalkyl" represents a saturated or unsaturated nonaromatic carbocyclic ring containing from 3 to 15 carbon atoms, preferably from 4 to 6 carbon atoms, and from 1 to 3 heteroatoms selected from O, S, —$SO_2$— or $NR^{95}$ (suitable heterocycloalkyl groups include tetrahydrofuranyl, tetrahydropyranyl, dihydropyranyl, tetrahydrothienyl, piperidinyl, pyrrolidinyl, piperazinyl, dioxanyl, morpholino, diaza-2,2,2-bicyclooctane etc.), wherein any of the available substitutable carbon and nitrogen atoms in the ring are optionally substituted with one, two, three or more groups independently selected from $C_1$–$C_6$ alkyl, aryl, aralkyl, haloalkyl, amino, alkylamino, dialkylamino, —$S(O)_m$-aryl (wherein m is 0, 1 or 2 and aryl is defined above), —$C(O)R^9$ (wherein $R^9$ is defined above) or an acyl radical of a naturally occuring amino acid; and "heteroaryl" (including the heteroaryl portion of heteroarylalkyl) represents a monocyclic, bicyclic or tricyclic group containing from 2 to 14 carbon atoms and comprising one or more, (preferably 1 to 3), heteroatoms selected from O, S or N, said heteroatoms interrupting a carbocyclic ring structure and having a sufficient number of delocalized pi electrons to provide aromatic character, such as triazolyl, pyridyl, imidazolyl, thienyl, furanyl, imidazolyl, quinolyl, isoquinolyl, benzofuranyl, benzopyranyl, benzothienyl, thiazolyl, indolyl, naphthyridinyl, or pyridyl N-oxide, wherein pyridyl N-oxide can be represented as:

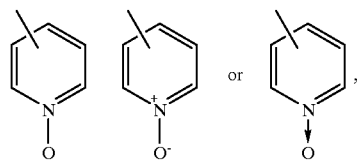

with all available substitutable carbon and heteroatoms of the cyclic group being intended as possible points of attachment, said cyclic group being optionally substituted with 1, 2, 3 or more groups independently selected from halo, alkyl, aryl, aralkyl, heteroaryl, hydroxy, alkoxy, phenoxy, —$NO_2$, —$CF_3$, amino, alkylamino, dialkylamino, and —$COOR^{60}$ wherein $R^{60}$ is as defined above (e.g., benzyl).

As used herein, the term "tertiary amine base" means DMAP, pyridine or a trialkylamine, such as $Et_3N$ or Hünigs base; and "hydride reducing agent" means a metal hydride reagent, such as $NaBH_4$, Red-Al, DIBAL-H, L-Selectride, Vitride, $LiBH_4$, $LiAlH_4$, $LiAl(OtBu)_3H$, $NaCNBH_3$, DMAB, zinc borohydride, calcium borohydride, sodium triacetoxyborohydride, a combination of $LiBH_4$ and $ZnBr_2$, or a combination of $NaBH_4$ and LiCl.

The term "acyl radical of a naturally occurring amino acid" means a group of the formula —C(O)—$R^{29}$, wherein $R^{29}$ is a group of the formula

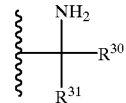

wherein $R^{30}$ and $R^{31}$ are the residual portions of said amino acid. For example $R^{30}$ and $R^{31}$ can be independently selected from H, alkyl or M-substituted alkyl, wherein M is HO—, HS—, $CH_3S$—, —$NH_2$, phenyl, p-hydroxyphenyl, imidazolyl or indolyl, such that HO—C(O)—$R^{29}$ is an amino acid selected from alanine, glycine, valine, leucine, isoleucine, phenylalanine, tryptophan, methionine, serine, threonine, histidine, cysteine or tyrosine.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFM); 1-hydroxybenzotriazole (HOBT); m-chloroperbenzoic acid (MCPBA); triethylamine ($Et_3N$); diethyl ether ($Et_2O$); ethyl chloroformate ($ClCO_2Et$); 1-(3-dimethylaminopropyl)-3-ethyl carbodiimde hydrochloride (DEC); N,N'-carbonyidiimidazole (CDI); 1,8-diaza-bicyclo[5.4.0]undec-7-ene (DBU); [O-(7-azabenzotriazol-1-yl)-1,1,3,3-tetramethyluronium hexafluorophosphate (HATU); tetrabuytlammonium fluoride (TBAF); dicyclohexylcarbodiimide (DCC); N,N-dimethylamino-pyridine (DMAP); diisopropylethylamine (Hünigs base); [2-(t-butoxy-carbonyloxyimino)-2-phenylacetonitrile] (BOC-ON); 9-fluorenylmethyl chloroformate (FMOC-Cl); sodium bis(2-methoxyethoxy)aluminum hydride (Red-Al); diisobutyl-aluminum hydride (DIBAL-H); lithium tri-sec-butylborohydride (L-selectride); dichloromethane (DCM); diisopropylcarbodiimide (DIC); and N,N-dimethylacetamide (DMA).

Lines drawn into the ring systems indicate that the indicated bond may be attached to any of the substitutable ring carbon atoms.

Certain compounds of the invention may exist in different isomeric (e.g., enantiomers, diastereoisomers or geometric isomers) forms. For example, compounds of the formula (1.0) wherein X is CH or N can have a chiral center at C11 of the tricyclic portion of the molecule, which C11 carbon can have the S or R absolute configuration, and various substituent groups, e.g. $R^1$, $R^2$, can also comprise chiral centers. The invention contemplates all such isomers both in pure form and in admixture, including racemic mixtures. In the particular case of compounds of formula (1.0) where $R^2$ is other than H, the carbon atom to which said $R^2$ group is attached can exist in the R or S configuration. While only one configuration is generally shown for such compounds of formula (1.0), the invention contemplates all such isomers both in pure form and in admixture, including racemic mixtures. Enol forms are also included, as are both the E and Z isomers of compounds containing a double bond, (e.g. compounds wherein $R^2$ is an alkenyl group).

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts and quaternary salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Those skilled in the art will appreciate that when x in formula 82.0 is greater than 1 (e.g., 2, 3, 4, 5 or 6) each $R^a$ and each $R^b$ is independently selected for each carbon to which they are bound. Thus, each $R^a$ and $R^b$ on adjacent carbons can be the same or different.

Examples of $R^1$, wherein $R^1$ is a group of formula (82.0), include compounds of group D, wherein D is —C(O)—$CH_2$—$R^5$, —C(O)—O—$R^5$ or —(O)—NH—$R^5$, wherein $R^5$ is pyridyl, pyridyl N-oxide,

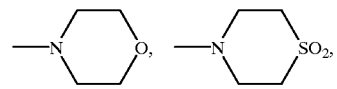

or a piperidinyl group of the formula

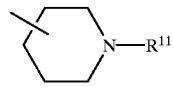

wherein $R^{11}$ represents H, $C_1$–$C_6$ alkyl, haloalkyl or —C(O)—$R^9$ wherein $R^9$ is $C_1$–$C_6$ alkyl, $C_1$–$C_6$ alkoxy or —NH($R^{10}$) wherein $R^{10}$ is H or alkyl, or the group —C(O)—$R^9$ represents an acyl radical of a naturally occurring amino acid.

$R^1$ substituents include those substituents for formula (82.0) wherein:
(a) T is selected from —C(O)—, —$SO_2$, or —C(O)—C(O)—;
(b) x is 0, 1, or 2 (e.g.,0 or 1);
(c) $R^a$ and $R^b$ are independently selected from: (1) H; (2) NH{C(O)}$_z$$R^{60}$ wherein z is 0 or 1 (e.g., z is 1), and $R^{60}$ is alkyl (e.g., methyl); (3) —(CH)$_w$S(O)$_m$$R^{60}$ wherein w is 0, 1, 2 or 3 (e.g., w is 0, 1, or 2, for example w is 2), m is 0, 1 or 2 (e.g., 0 or 2), and $R^{60}$ is alkyl (e.g., methyl); (4) alkyl (e.g., methyl); or (5) $C_1$–$C_6$ alkoxy (e.g., —$OCH_3$); or $R^a$ and $R^b$ taken together represent cycloalkyl (e.g., cyclopentyl or cyclopropyl), or =O; and
(d) $R^{92}$ is selected from (1) H; (2) aryl (e.g., phenyl or naphthyl); (3) substituted aryl, for example, aryl having substituents independently selected from (i) alkoxy (e.g., —$OCH_3$), (ii) methylenedioxy, (iii) aralkoxy (e.g., benzyloxy), (iv) aryloxy (e.g., phenoxy—i.e., $C_6H_5O$—), (v) alkyl (e.g., —$CH(CH_3)_2$), (vi) halo (e.g., Cl), (vii) aryl (e.g., phenyl) or (viii) alkyl substituted with a heterocycloalkyl ring

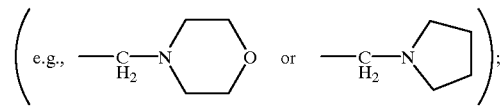

(4) aralkyl (e.g., benzyl and diphenylmethyl); (5) aryloxy (e.g., phenoxy); (6) arylthio (e.g., $C_6H_5S$—); (7) alkyl (e.g., methyl); (8) heteroaryl (e.g., pyridyl N-oxide, indolyl, thienyl, quinolinyl, benzothienyl and pyridyl); (9) substituted heteroaryl, for example, heteroaryl having substituents independently selected from (i) aryl (e.g., phenyl), (ii) alkyl (e.g., methyl), (iii) alkoxy (e.g., methoxy), (iv) amino (e.g., —$NH_2$), or (v) aralkyl (e.g., benzyl); (10) substituted heterocycloalkyl, for example, heterocycloalkyl having substituents independently selected from (i) aryl (e.g., phenyl) or (ii) —S(O)$_m$-aryl wherein (e.g., m is 2 and aryl represents phenyl substituted with methyl); or (11) substituted alkyl, for example, alkyl having substituents independently selected from —S(O)$_m$-alkyl wherein m is 0, 1, or 2 (e.g., ethyl substituted with —$SO_2CH_3$ or —$SCH_3$).

Examples of substituted aryl groups for $R^{92}$ include methoxyphenyl, dimethoxyphenyl (i.e., $(CH_3O)_2C_6H_4$), methylenedioxyphenyl, benzyloxyphenyl, phenoxyphenyl (i.e., $C_6H_5OC_6H_4$), $C_6H_4CH(CH_3)_2$, chlorophenyl, dichlorophenyl, and phenylphenyl (i.e., biphenyl, $C_6H_5C_6H_4$).

Examples of substituted heteroaryls for $R^{92}$ include thiazole substituted with a phenyl group and a methyl group, thiazole substituted with —$NH_2$ and indole substituted at the nitrogen with benzyl.

Examples of substituted heterocycloalkyl groups for $R^{92}$ include the substituent:

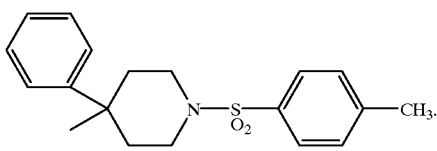

Preferably, $R^1$ is selected from: (1) a group of the formula —C(O)—$CH_2$—$R^5$ wherein $R^5$ is

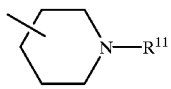

wherein $R^{11}$ is —C(O)—$R^9$, $R^9$ is —NH($R^{10}$) and $R^{10}$ is H, for example, $R^5$ is a group of the formula

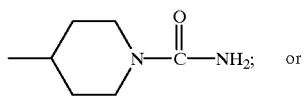

(2) a group of formula (82.0) wherein T is —C(O)—, x is 1 or 2 and $R^{92}$ is aryl (preferably phenyl) or heteroaryl (preferably pyridyl or pyridyl N-oxide, e.g., 3- or 4- pyridyl or 3- or 4- pyridyl N-oxide).

Examples of $R^1$, wherein $R^1$ is a group of formula (82.0), also include groups of the formula:

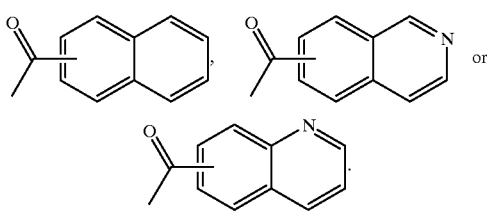

Examples of $R^1$, wherein $R^1$ is a group of formula (82.0), also include groups of the formula:

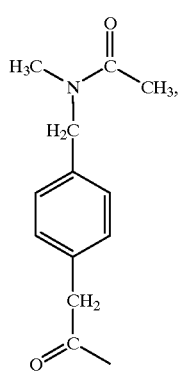
(101.0)

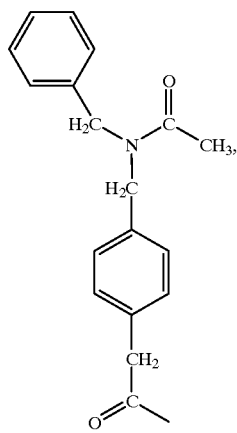
(102.0)

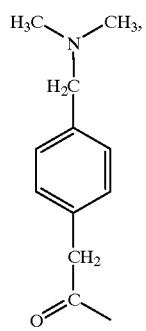
(103.0)

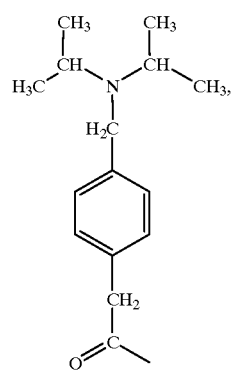
(104.0)

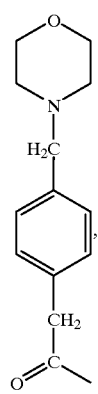
(105.0)

(106.0) 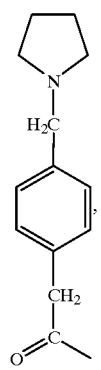
(107.0) 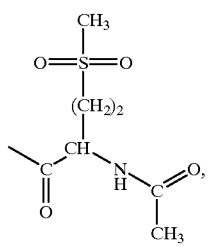
(108.0) 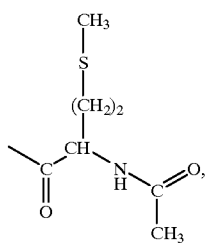
(109.0) 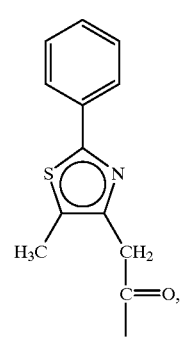
(110.0) 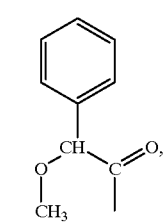
(112.0) 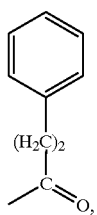
(113.0) 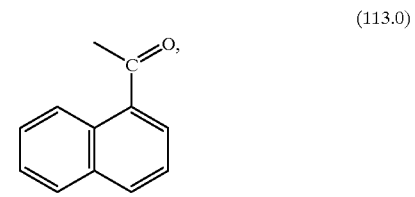
(115.0) 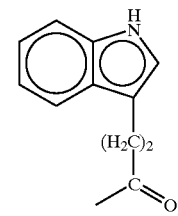
(117.0) 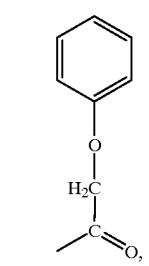
(118.0) 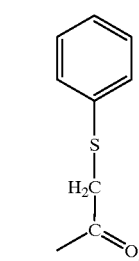
(119.0) 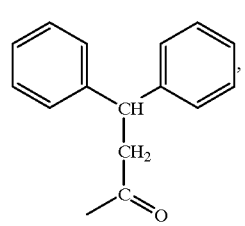

-continued
(120.0)
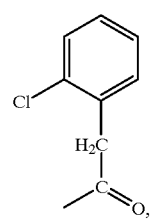
(121.0)
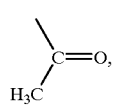
(122.0)
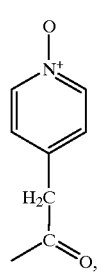
(123.0)
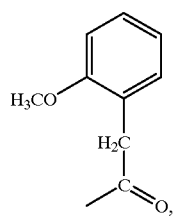
(124.0)
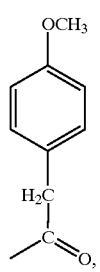
(125.0)
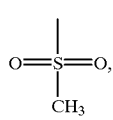
(127.0)
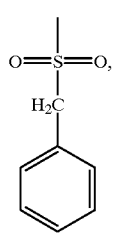
(128.0)
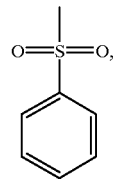
(129.0)
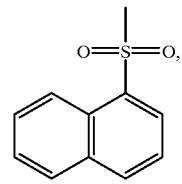
(131.0)
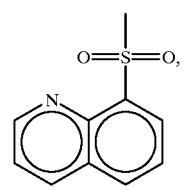
(132.0)
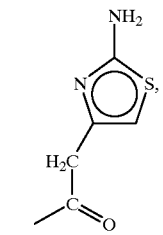
(135.0)
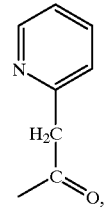
(136.0)
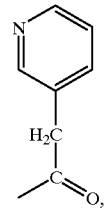
(137.0)
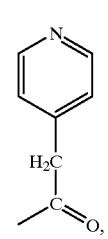

(138.0)
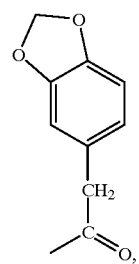
(139.0)
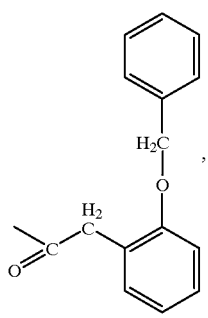
(140.0)
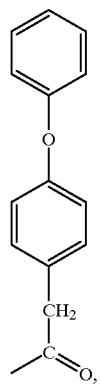
(141.0)
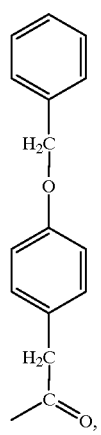
(142.0)
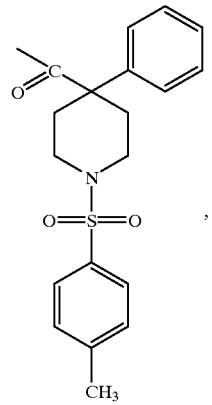
(143.0)
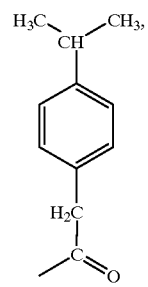
(145.0)
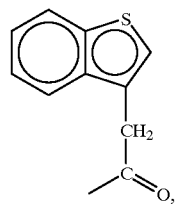
(146.0)
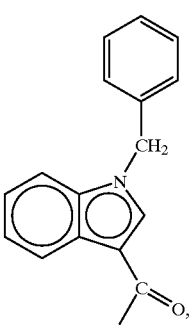
(147.0)
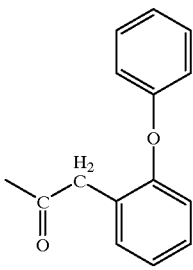

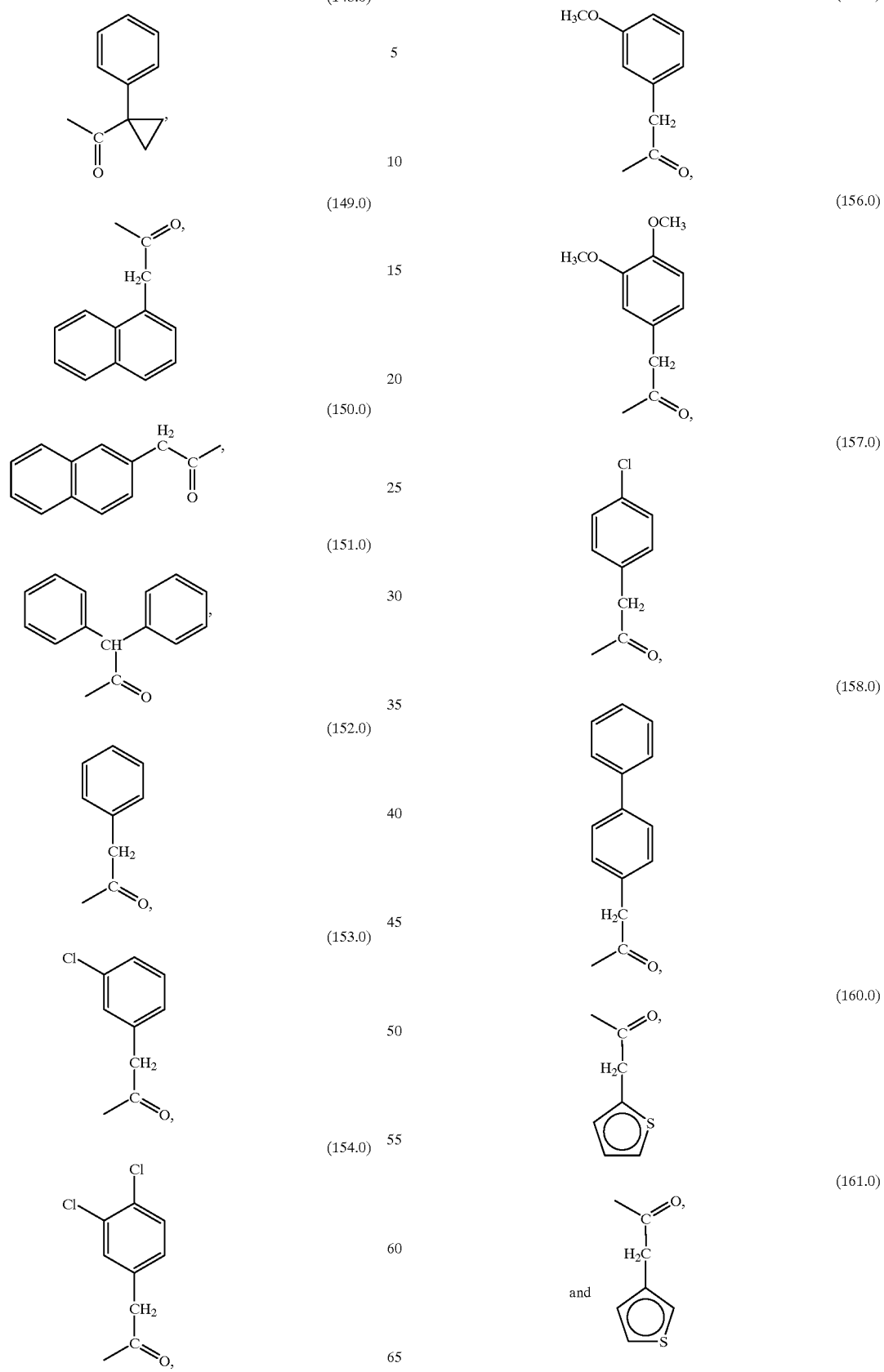

Examples of R¹ also include groups selected from:

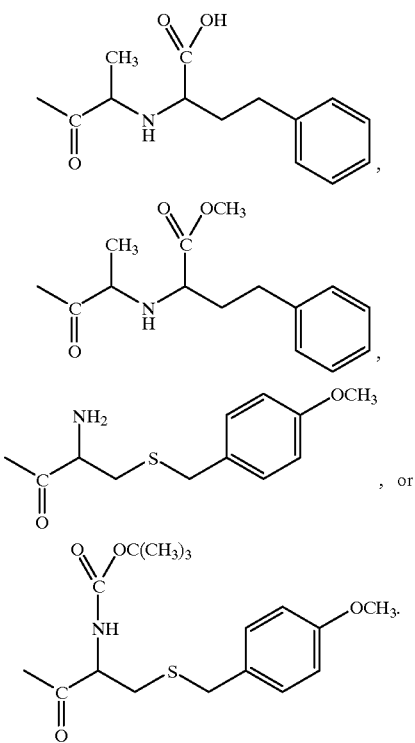, or

Examples of R² groups include: (1) —C(O)NR⁶R⁷ (for example see formula 84.0 below), and (2) substituted alkyl wherein the substituent is —C(O)NR⁶R⁷ (e.g., —CH₂C(O)NR⁶R⁷, for example, see formula 86.0 below). Examples of R⁶ and R⁷ for these groups include: (1) H; (2) substituted alkyl, for example, alkyl having substituents independently selected from (i) —CN, (ii) cycloalkyl (e.g., cyclopropyl and cyclohexyl), (iii) alkoxy (e.g., methoxy), (iv)—S-alkyl (e.g., —SCH₃), (iv) aryl (e.g., phenyl and naphthyl), (v) substituted aryl (e.g., chlorophenyl, nitrophenyl and methoxyphenyl), (vi) heterocycloalkyl (e.g., tetrahydrofuranyl), (vii) methylenedioxyphenyl, (viii) —O—alkyl-O-alkyl (e.g., —O(CH₂)₂OCH₃); (3) alkyl (e.g., methyl, isopropyl, —CH₂CH(CH₃)₂, and n-butyl), (4) cycloalkyl (e.g., cyclopropyl), (5) heteroarylalkyl (e.g., —CH₂-pyridyl, —(CH₂)₃-imidazolyl, —CH₂-thienyl, and —CH₂-furanyl), and (6) aralkyl wherein said aryl group is substituted (e.g., —(CH₂)₂C₆H₄OCH₃ and —(CH₂)₂C₆H₄(OCH₃)₂).

Examples of substituted alkyl groups for the above R⁶ and R⁷ groups include: —(CH₂)₂CN, —CH₂-cyclopropyl, —(CH₂)₂OCH₃, —(CH₂)₃OCH₃, —(CH₂)₂SCH₃, —CH₂CH(C₆H₅)₂, —(CH₂)₂C₆H₅, —(CH₂)₄C₆H₅, —CH₂C₆H₅, —CH₂-naphthyl, —(CH₂)₂C₆H₄Cl, —CH₂C₆H₄Cl, —CH₂-tetrahydrofuranyl, —CH₂-cyclohexyl, —(CH₂)₃O(CH₂)₂OCH₃,

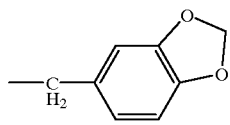

(i.e.,—CH₂-methylenedioxyphenyl), and —CH₂-nitrophenyl.

Preferably, R² is selected from —C(O)NR⁶R⁷ or —CH₂C(O)NR⁶R⁷ wherein, preferably, R⁶ and R⁷ are independently selected from H, alkyl, cycloalkyl, heteroarylalkyl or heteroaryl, and most preferably R⁶ and R⁷ are independently selected from H, alkyl, cycloalkyl or heteroarylalkyl.

Examples of R² include groups having the formula:

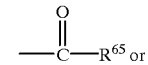 (84.0)

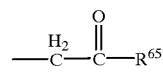 (86.0)

wherein R⁶⁵ in formulas (84.0) and (86.0) are selected from:

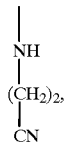 (201.0)

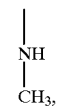 (202.0)

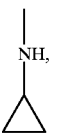 (203.0)

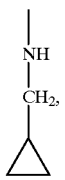 (204.0)

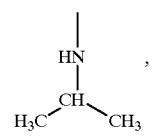 (205.0)

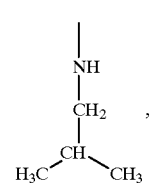 (206.0)

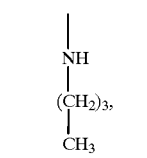 (207.0)

-continued
(208.0) 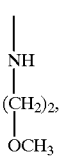
(209.0) 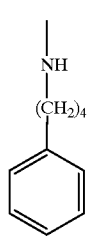
(210.0) 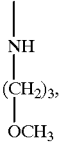
(211.0) 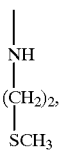
(212.0) 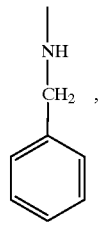
(213.0) 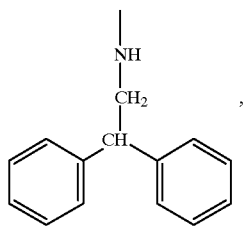
(214.0) 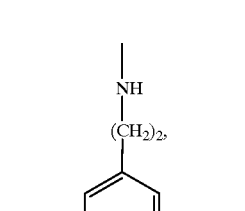
-continued
(215.0) 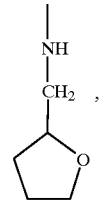
(216.0) 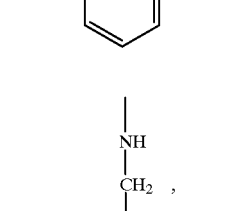
(217.0) 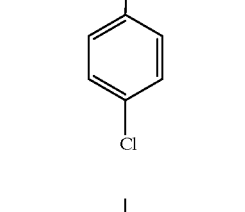
(219.0) 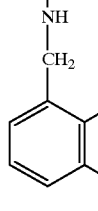
(220.0) 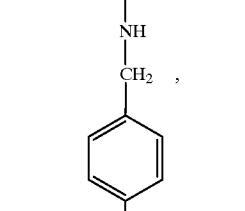
(221.0) 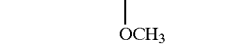

(222.0)
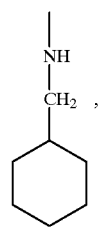
(223.0)
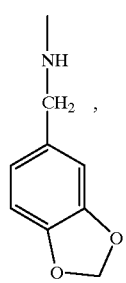
(224.0)
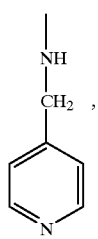
(225.0)
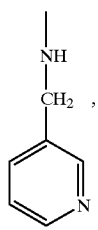
(226.0)
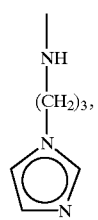
(227.0)
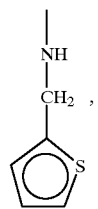
(228.0)
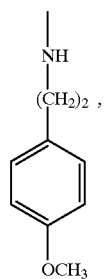
(229.0)
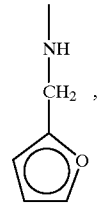
(230.0) , or
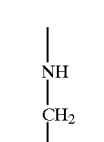
(231.0)
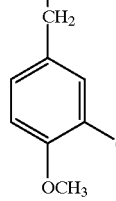
Examples of R² groups also include: (1) alkyl, (2) substituted alkyl, for example, alkyl having substituents independently selected from (i) aryl, (ii) —OR⁶, (iii) —S(O)ₜR⁶, and (iv) —N(R⁶)—C(O)R⁷; and (3) —C(O)OR⁶. Examples of such R² groups include the groups: $CH_3(CH_2)_3-$, $C_6H_5CH_2-$, $CH_3O(CH_2)_2-$, $CH_3S(CH_2)_2-$, $CH_3O(CH_2)_3-$, $n-C_3H_7O(CH_2)_2-$, $CH_3CONH-(CH_2)_4-$, $-CH_2OH$, $-C(O)OC_2H_5$,
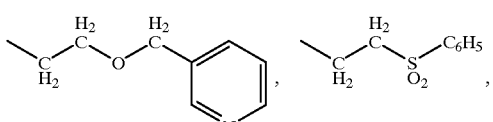

Examples of $R^2$ groups also include

Those skilled in the art will recognize that the disulfide dimers for $R^1$ can be represented by the formulas:

Certain compounds of the formula (1.0) comprise sulfhydryl groups, (i.e., —$CH_2SH$), which sulfhydryl groups are capable of reacting to form disulfide bonds resulting in dimeric compounds. An example of such dimers are disulfides of the formula (Ia). Said sulfhydryl groups can also form disulfides with other thiols such as glutathione. Disulfides including but not limited to disulfides of formula (Ia) are within the scope of the invention and are encompassed by the structure of formula (1.0).

(Ia)

Compounds of the formula (1.0) can generally be prepared from an amine of the formula (2.0) as shown in Reaction Scheme 1.

Reaction Scheme 1

For compounds of the formula (1.0) wherein $R^1$ and the nitrogen atom to which it is attached together comprise an amide, e.g. where $R^1$ is —C(O)—$CH_2$—$R^5$, the amine (2.0) is reacted with a carboxylic acid of the formula $R^{20}$—C(O)—OH, wherein $R^{20}$—C(O)— is $R^1$, in the presence of a coupling agent such as DEC,CDI or DCC. The reaction is typically carried out in a suitable organic solvent such as DMF, THF or $CH_2Cl_2$ at a temperature of −10° to 100° C., preferably at 0° to 50° C., and most preferably at about room temperature. When the coupling agent is DCC or DEC, the reaction is preferably conducted in the presence of HOBT and N-methylmorpholine.

Alternatively, the amine (2.0) can be reacted with a compound of the formula $R^1$-L, wherein $R^1$ is as defined above and L is a leaving group, such as Cl, Br, I, —O—C(O)—$R^{40}$ wherein $R^{40}$ is $C_1$–$C_6$ alkyl or phenyl, or a sulfonate group of the formula —$OSO_2$—$R^{20}$, wherein $R^{20}$ is selected from $C_1$–$C_6$ alkyl, phenyl, $CF_3$, tolyl and p-bromophenyl, to form a compound of the formula (1.0). The reaction is carried out in the presence of a base, preferably a tertiary amine base, such as $Et_3N$, DMAP, pyridine or Hünigs base.

Compounds of Formula 1.0 wherein: $R^1$ is —C(O)—$CH_2$—$R^5$, $R^5$ is a piperidine of the formula:

$R^{11}$ represents —C(O)—$R^9$, $R^9$ is —NH($R^{10}$) and $R^{10}$ is H (i.e., a carboxamide) can be made by reacting a compound of Formula 1.0, wherein $R^1$ is —C(O)—$CH_2$—$R^5$ and $R^5$ is the above described piperidine wherein $R^{11}$ is H, with an excess of urea in water. This reaction can be run with about 4 to about 10 equivalents of urea relative to the unsubstituted piperidine starting reactant. Generally, about 10 equivalents of urea can be used. The reaction is run for about 3 to about 68 hours. Generally, the reaction can be run for about 60 to 70 hours. The reaction is usually run at the reflux temperature of the reaction mixture. This can range from about 98 to about 100° C. The amount of the unsubstituted piperidine starting reactant relative to water may typically vary from about 0.025 g/ml to about 0.6 g/ml, and can generally be about 0.1 g/ml.

For preparing compounds of the formula (1.0) wherein $R^1$ and the nitrogen atom to which it is attached together comprise an amine, e.g. where $R^1$ is a group of the formula

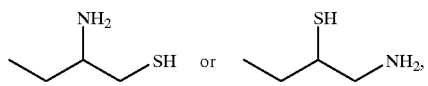

the amine (2.0) is reacted with an aldehyde of the formula $R^{21}$—CHO, wherein $R^{21}$ is selected such that $R^1$ corresponds to $R^{21}$—CH$_2$—, e.g. an aldehyde of the formula

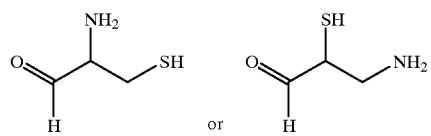

to form an imine of the formula (3.0), wherein $R^{21}$ is as defined above, as shown in Reaction Scheme 2. The —NH$_2$ and —SH groups of such aldehydes are typically protected, e.g. as the N-BOC and S-Tr groups, respectively. The imine (3.0) is reduced under suitable reaction conditions to form a compound of the formula (1.0). Preferably the reduction is carried out using a hydride reducing agent, such as sodium triacetoxyborohydride or NaCNBH$_3$, preferably in the presence of molecular sieves.

Reaction Scheme 2

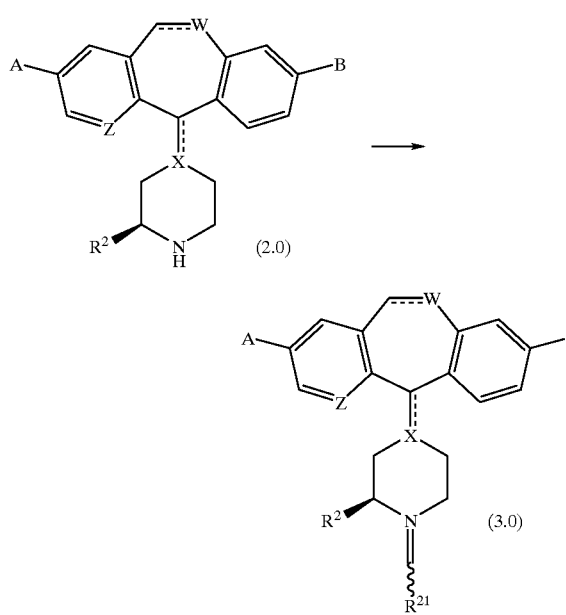

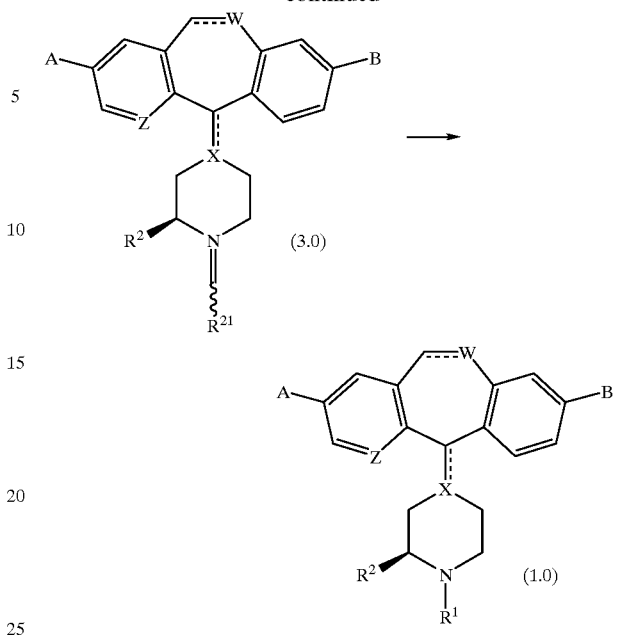

When conducting the reactions described above, where $R^1$ comprises a chemically reactive group, such as amine thiol group, such groups must generally be protected with a suitable protecting group, which can later be removed to complate the synthesis of a compound of formula (1.0). For example, amines can preferably be protected with the BOC protecting group, while thiols can be protected with the trityl (i.e., triphenylmethyl) protecting group. Deprotection, i.e., the removal of these protecting groups is then generally the final step in the synthesis of such compounds of formula (1.0).

For preparing compounds of the formula (1.0) wherein $R^1$ is —C(O)—NH—$R^5$, a compound of the formula (2.0) is reacted with an isocyanate of the formula $R^5$—N=C=O, in a suitable solvent such as DMF, THF or CH$_2$Cl$_2$ using methods well known in the art.

Alternatively, an amine (2.0) is reacted with phosgene to form a chloroformate intermediate of the formula (4.0), as shown in Reaction Scheme 3. The chloroformate (4.0) is generally not isolated and is reacted with an amine of the formula $R^5$—NH$_2$, wherein $R^5$ is as defined above, to form a compound of the formula (1.0), wherein $R^1$ is —C(O)—NH—$R^5$.

Reaction Scheme 3

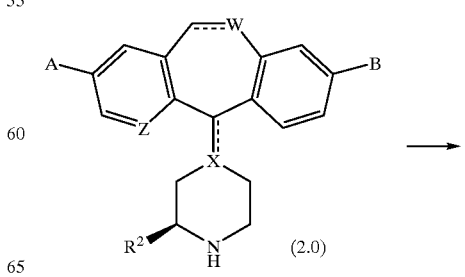

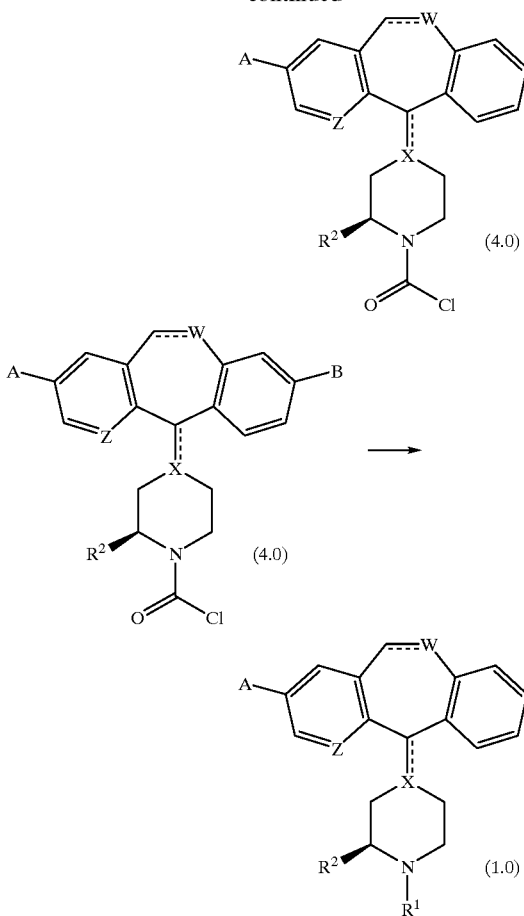

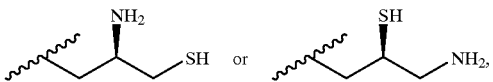

Compounds of the formula (1.0) wherein $R^1$ is —C(O)—O—$R^5$ can be prepared by reacting a compound of the formula (2.0) with a chloroformate of the formula $R^5$—O—C(O)Cl, wherein $R^5$ is as defined above, in the presence of a base, such as a tertiary amine base, to form a compound of formula (1.0). Alternatively, a compound (1.0) wherein $R^1$ is —C(O)—O—$R^5$ can be prepared by reacting a compound of formula (4.0) with an alcohol of the formula $R^5$—OH Certain compounds of formula (1.0) can be converted to other compounds of the formula (1.0) using standard reaction conditions. For example, compounds of the formula (1.0) wherein $R^2$ is —$CO_2H$, (i.e., —C(O)O$R^6$ and $R^6$ is H), can be prepared by ozonolysis of a compound of formula (1.0) wherein $R^2$ is $CH_2$=CH—, followed by oxidation of the resulting aldehyde.

Compounds of the formula (1.0) wherein $R^2$ is —C(O)O$R^6$, where $R^6$ is other than H, can be prepared from a compound of the formula (1.0) wherein $R^2$ is —$CO_2H$ by treating with $SOCl_2$ or oxalyl chloride, then with an alcohol of the formula $R^6OH$, wherein $R^6$ is as defined above. Similarly, compounds of formula (1.0) wherein $R^2$ is —C(O)N$R^6R^7$ can be prepared from a compound of the formula (1.0) wherein $R^2$ is —$CO_2H$ via essentially the same method but substituting an amine of the formula $R^6R^7NH$ for the alcohol $R^6OH$. Alternatively, compounds of formula (1.0) wherein $R^2$ is —C(O)N$R^6R^7$ can be prepared by reacting a compound of the formula (1.0) wherein $R^2$ is —$CO_2H$ with an amine $R^6R^7NH$ in the presence of a coupling agent, such as DCC or DEC.

In an analogous manner, compounds of formula (1.0) wherein $R^2$ is alkyl substituted by a group of the formula —C(O)O$R^6$ or —C(O)N$R^6R^7$ can be prepared via substantially the same procedures as described above to form compounds wherein $R^2$ is —$CO_2H$, —C(O)O$R^6$ or —C(O)N$R^6R^7$, by replacing the compound of formula (1.0) wherein $R^2$ is $CH_2$=CH— with an appropriate alkenyl group, (i.e., a group of the formula —$(CH_2)_p$—CH=$CH_2$, wherein p is 1, 2, 3, 4, etc.).

Compounds of the formula (1.0) wherein $R^2$ contains a substituent of formula —S(O)$_tR^6$, wherein t=1 or 2, can be prepared by oxidation of an analogous compound of the formula (1.0) wherein $R^2$ contains a substituent of formula —S(O)$_tR^6$, wherein t=0, using a suitable oxidizing agent, such as a peracid, preferably MCPBA.

One skilled in the art will recognize that the above transformations may, in certain instances, such as where $R^1$ is a group of the formula require that the oxidation be carried out prior to introduction of the $R^1$ group to formula (1.0).

Amines of the formula (2.0) can be prepared in optically active form using appropriate chiral starting materials or alternatively can be prepared using racemic starting compounds to give a mixture of stereoisomeric compounds which can then be separated by resolution or chiral HPLC to give the desired compound (2.0). For example, compounds (2.0) and (2.10) are stereoisomeric amines which can be separated by classical resolution techniques using a suitable resolving agent, such as a chiral acid. Chiral acid resolving agents are well known in the art and include such compounds as D- or L-malic acid, D- or L-tartaric acid, di-p-toluoyl-D-tartaric acid, di-p-toluoyl-L-tartaric acid, di-benzoyl-D-tartaric acid and di-benzoyl-L-tartaric acid. Alternatively, the stereoisomeric amines (2.0) and (2.10) could be separated using a chiral HPLC column via standard methods.

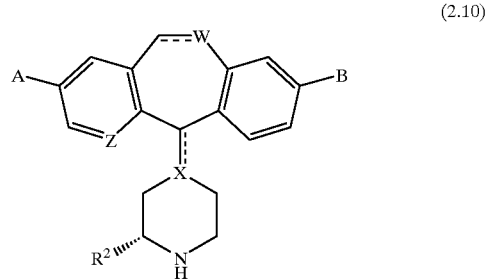

For example, in the case of compounds of the formula (2.0) and (2.10) wherein X is N or CH, at least four stereoisomers of said compounds can exist, i.e., compounds of formula (2.20), (2.21), (2.22) and (2.23).

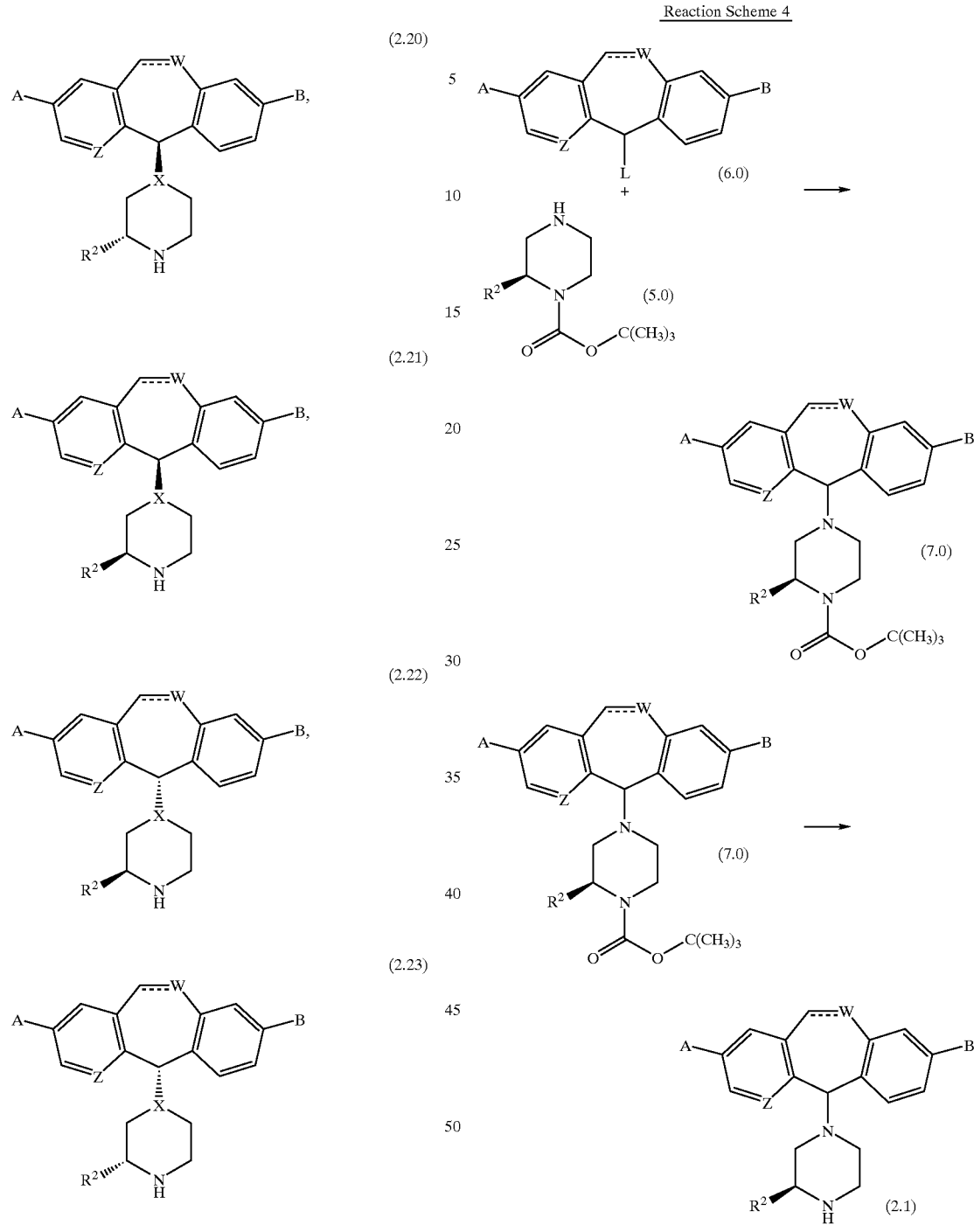

Diastereomers, such as compounds (2.20) and (2.22), or (2.21) and (2.23) can typically be separated using conventional methods, such as chromatography. Resolution methods are required for separation of enantiomers, such as compounds (2.20) and (2.21), or (2.22) and (2.23).

Amines of the formula (2.1), i.e., an amine of the formula (2.0) wherein X is N, can be prepared from a piperazine derivative of the formula (5.0), wherein $R^2$ is as defined above, and a compound of the formula (6.0), wherein L is a leaving group as defined above and A, B, W and Z are as defined above, via the process shown in Reaction Scheme 4.

In the process of Reaction Scheme 4, the piperazine (5.0) is reacted with compound (6.0) in the presence of a base, such as a tertiary amine base, to form a compound of the formula (7.0). Compound (7.0) is then hydrolyzed using a suitable acid, such as TFA, HCl or $H_2SO_4$, in a solvent such as dioxane or $CH_2Cl_2$, to form the amine (2.1).

Amines of the formula (2.2), i.e., an amine of the formula (2.0) wherein X is C or CH, can be prepared by hydrolysis of a carbamate compound of the formula (8.0), wherein $R^{22}$ is $C_1$–$C_6$ alkyl preferably ethyl or t-butyl, and $R^2$, A, B, W and Z are as defined above. The hydrolysis is carried out using a suitable acid, such as HCl, in a solvent such as dioxane.

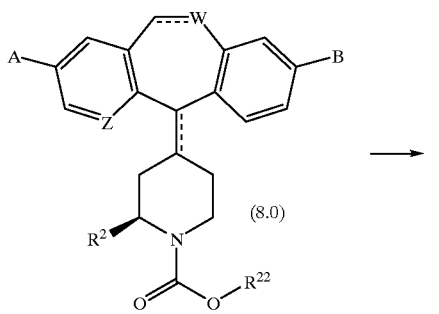

(8.0)

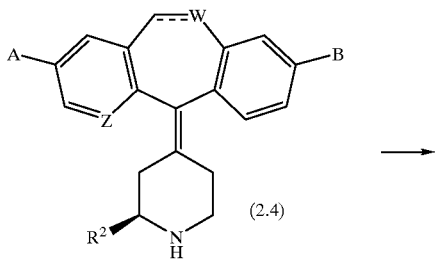

(2.2)

Amines of the formula (2.3), i.e., an amine of the formula (2.0) wherein X is CH, can be prepared by reduction of an amine of the formula (2.4), i.e., an amine of the formula (2.0) wherein X is C. The reduction is typically carried out using a suitable reducing agent, such as DIBAL-H or LiAlH$_4$, in a solvent such as THF or toluene, preferably at a temperature of 30° to 100° C.

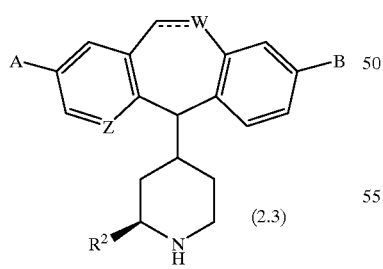

(2.4)

(2.3)

Carbamates of the formula (8.0) can be prepared by reacting a N-methyl compound of the formula (9.0) wherein X is C or CH, and A, B, W and Z are as defined above, with an alkyl chloroformate of the formula R$^{22}$OC(O)Cl, wherein R$^{22}$ is C$_1$–C$_6$ alkyl, preferably ethyl, following substantially the same procedures as described in U.S. Pat. Nos. 4,282,233 and 4,335,036.

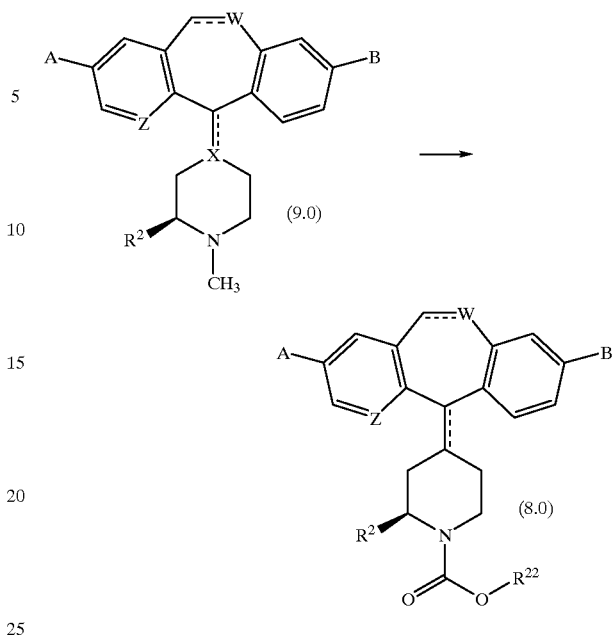

(9.0)

(8.0)

Compounds of the formula (9.1), i.e., a compound of the formula (9.0) wherein X is C, can generally be prepared via methods disclosed in U.S. Pat. No. 3,326,924, and in PCT International Publications WO/92/20681 and WO93/02081.

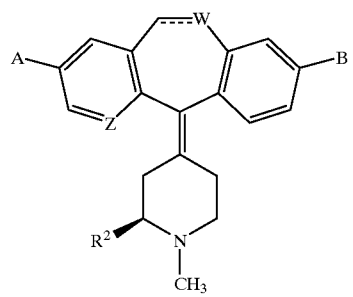

(9.1)

Compounds of the formula (9.1) can be prepared from a Grignard reagent of the formula (12.0) and a ketone of the formula (14.0), wherein A, B, W and Z are as defined above, via the process shown in Reaction Scheme 5.

Reaction Scheme 5

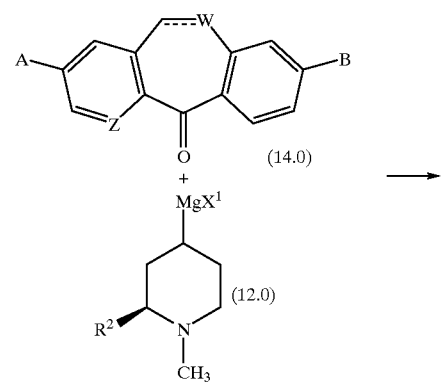

(14.0)

+ MgX$^1$ (12.0)

-continued

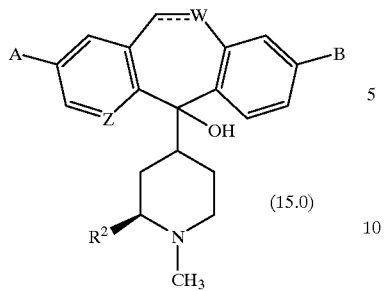

(15.0)

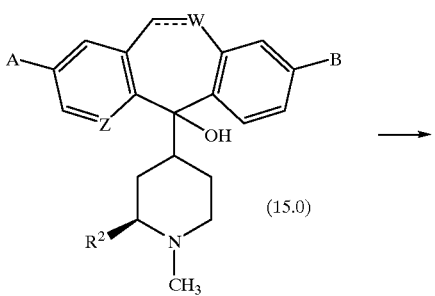

(15.0)

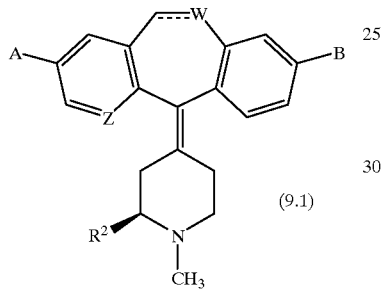

(9.1)

In the process of Reaction Scheme 5, the Grignard reagent (12.0) is reacted with the ketone (14.0) to form a compound of the formula (15.0). The reaction is generally performed under anhydrous conditions in an inert solvent, such as THF, Et$_2$O or toluene, at a temperature of 0° to 75° C., with hydrolysis of the resulting intermediate, typically using an aqueous acid, such as aqueous HCl, to form the alcohol (15.0). Alternatively, another organometallic reagent can be used in place of the Grignard reagent, such as an organolithium reagent, (i.e., a compound of formula (12.0) wherein MgX$^1$ is replaced by Li).

Compound (15.0) is dehydrated, e.g. by treating with an acid, such as H$_2$SO$_4$, to form a compound of the formula (9.1).

Ketones of the formula (14.0) are known or can be prepared by the procedures described in *J. Med. Chem.*, 4238 (1992), U.S. Pat. No. 5,089,496, and in PCT International Publications WO92/20681 and WO93/02081. For example, intramolecular cyclization of a nitrile of formula (11.0), as defined below, using a strong acid, such as CF$_3$SO$_3$H, at a temperature of −15° to 100° C., to form an imine intermediate which is hydrolyzed with water or aqueous acid to form the ketone (14.0).

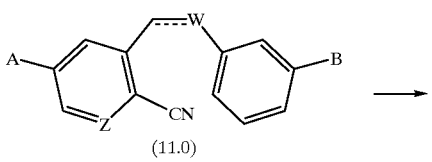

(11.0)

-continued

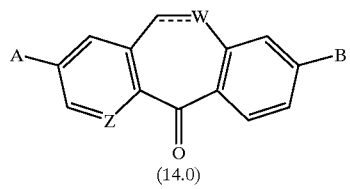

(14.0)

Alternatively, intramolecular Friedel-Crafts acylation of an acid chloride of formula (16.0) may also provide the desired ketone of formula (14.0). The reaction may be carried out under usual Friedel-Crafts conditions in an inert solvent and in the presence of a Lewis acid such as aluminum chloride.

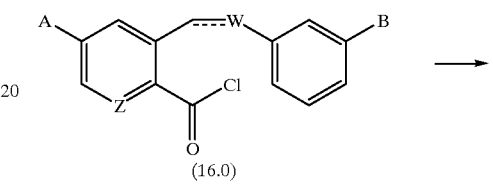

(16.0)

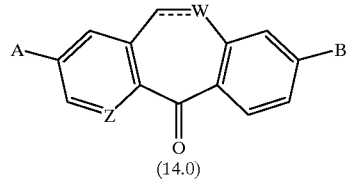

(14.0)

Ketones of the formula (14.1), i.e., a compound of the formula (14.0) wherein W is CH, can be prepared by heating a compound of the formula (14.3), i.e., a compound of formula (14.0) wherein W is CH$_2$, with SeO$_2$ in acetic acid.

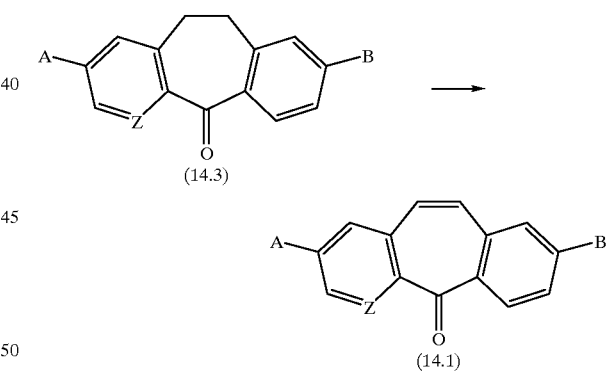

Acid chlorides of formula (16.0) can be obtained by hydrolysis of a compound of formula (11.0) to the corresponding carboxylic acid typically by heating with an aqueous acid (e.g., aqueous HCl), followed by conversion of the acid to the acid chloride of (16.0) under standard conditions well known to those skilled in the art (e.g., by treating with SOCl$_2$ or oxalyl chloride).

Compounds of the formula (11.1), i.e., compounds of the formula (11.0) wherein W is CH$_2$, are known or can generally be prepared by the process shown in Reaction Scheme 6. According to the process of Reaction Scheme 6 a solution of a compound of the formula (17.0), wherein A is as defined above, in t-butanol is heated in the presence of concentrated H$_2$SO$_4$ to form a t-butylamide of the formula (18.0). The t-butylamide (18.0) is reacted with an alkyllithium reagent, such as n-butyllithium, at −100° to 0° C., preferably at −60° to −20° C., then treated with NaBr and a benzyl halide of formula (19.0), wherein $X^1$ is Cl, Br or I, and B is as defined above, to form a compound of the formula (41.0). Compound (41.0) is treated with $POCl_3$ in a suitable solvent, such as toluene at 30° to 120° C., preferably at reflux, to form compound (11.1).

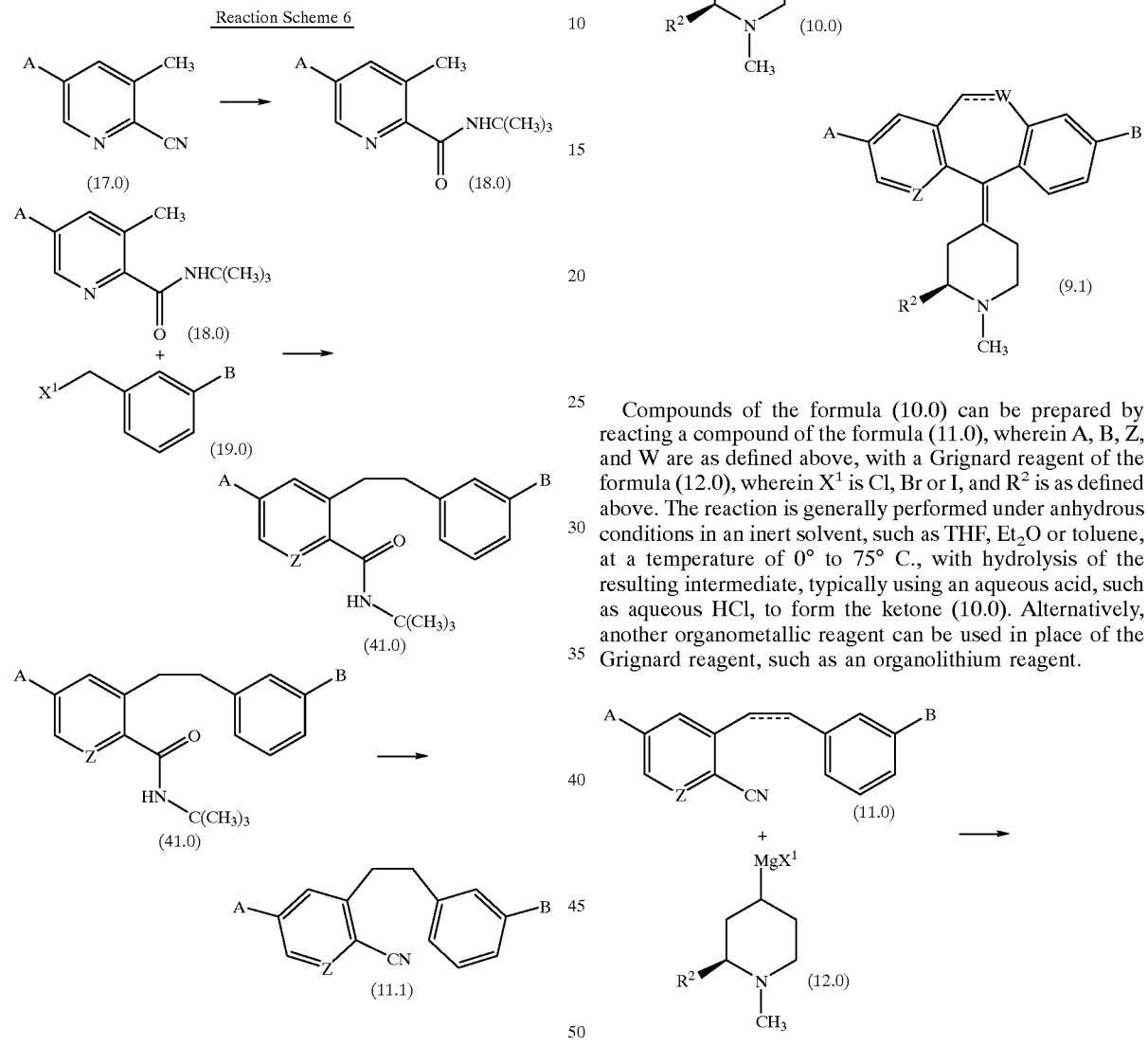

Compounds of the formula (9.1) can also be prepared by cyclizing a ketone of the formula (10.0), wherein $R^2$, A, B, Z and W are as defined above. The cyclization is conducted by treating compound (10.0) with a super acid, such as $HF/BF_3$, $CF_3SO_3H$ or $CH_3SO_3H/BF_3$. The reaction can be performed neat or in the presence of a suitable inert solvent such as $CH_2Cl_2$. Where $HF/BF_3$ is used for cyclization, the reaction is generally carried out at −60° to 10° C., preferably at −50° to 5° C., and the reaction time is controlled to minimize side reactions caused by reaction of HF with the product (9.1). Where the super acid is $CF_3SO_3H$, the reaction is typically carried out at 25° to 150° C., preferably at 40° to 120° C. An excess of super acid is generally used, typically 1.5 equiv. to 30 equiv.

Compounds of the formula (10.0) can be prepared by reacting a compound of the formula (11.0), wherein A, B, Z, and W are as defined above, with a Grignard reagent of the formula (12.0), wherein $X^1$ is Cl, Br or I, and $R^2$ is as defined above. The reaction is generally performed under anhydrous conditions in an inert solvent, such as THF, $Et_2O$ or toluene, at a temperature of 0° to 75° C., with hydrolysis of the resulting intermediate, typically using an aqueous acid, such as aqueous HCl, to form the ketone (10.0). Alternatively, another organometallic reagent can be used in place of the Grignard reagent, such as an organolithium reagent.

The Grignard reagent (12.0) can be prepared from the corresponding halo compound (13.0), wherein $X^1$ is Cl, Br or I, and $R^2$ is as defined above, using Mg metal via standard procedures known in the art. Similarly, the analogous organolithium compounds can be prepared from the halides (13.0) via standard methods, e.g. via transmetallation using an alkyllithium compound, such as t-butyllithium.

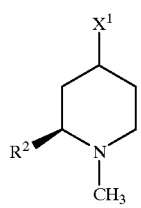

(13.0)

Amines of the formula (2.5), wherein $X^2$ is Br or I, (i.e., amines of the formula (2.0) wherein A is Br or I, and X is CH or C), can be prepared via the process shown in Reaction Scheme 7.

Reaction Scheme 7

Step A:

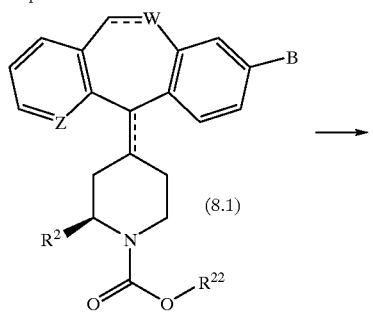

(8.1)

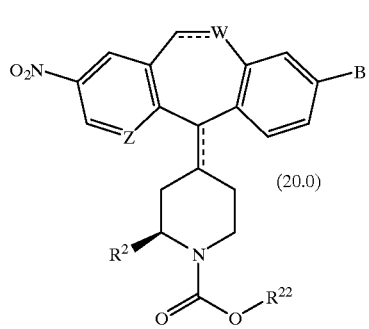

(20.0)

Step B:

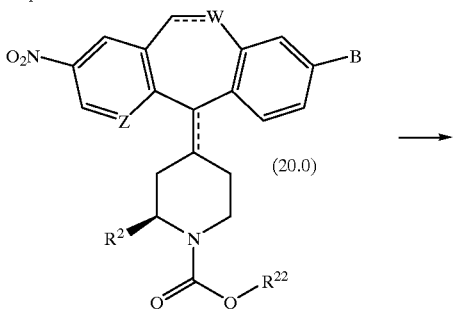

(20.0)

-continued

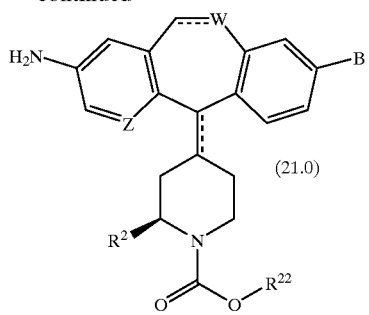

(21.0)

Step C:

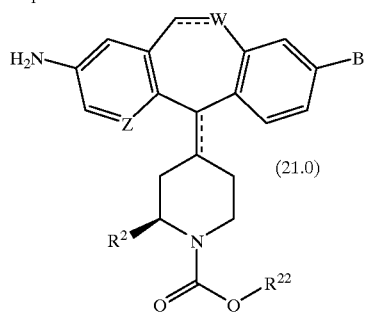

(21.0)

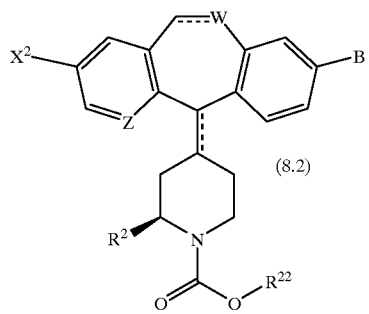

(8.2)

Step D:

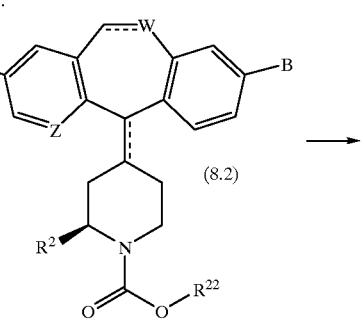

(8.2)

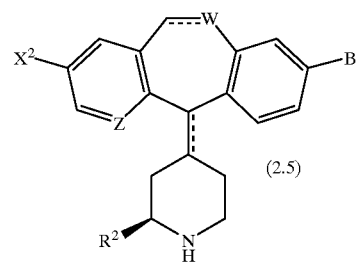

(2.5)

In Step A of Reaction Scheme 7, a compound of the formula (8.1), i.e., a compound of formula (8.0) wherein A is H, is reacted with a tetraalkylammonium nitrate, such as tetrabutylammonium nitrate, and TFAA in a suitable solvent, such as $CH_2Cl_2$, at $-30°$ to $20°$ C., preferably at about $0°$ C., to form a compound of the formula (20.0), wherein $R^{22}$, B, W, Z and $R^2$ are as defined above.

In Step B, compound (20.0) is heated with a suitable reducing agent, such as a combination of Fe and $CaCl_2$, in a polar solvent, such as a $C_1$–$C_4$ alcohol, preferably EtOH, at a temperature of $40°$ to $100°$, preferably at $50°$ to $80°$ C., to form a compound of formula (21.0), wherein $R^{22}$, B, W, Z and $R^2$ are as defined above.

In Step C, compound (21.0) is converted to the halide (8.2), wherein $X^2$ is Br or I, and $R^{22}$, B, W, Z and $R^2$ are as defined above. For forming a compound of formula (8.2) wherein $X^2$ is Br, compound (21.0) is treated with $Br_2$ and HBr at a temperature of $-30°$ to $15°$ C., preferably at $-10°$ to $10°$ C., to form the bromide, (i.e., a compound (8.2) wherein $X^2$ is Br). For preparing a compound of formula (8.2) wherein $X^2$ is I, compound (21.0) is treated with $I_2$ in a suitable solvent, such as benzene, at a temperature of $30°$ to $100°$ C., preferably at $50°$ to $70°$ C., to form the iodide, (i.e., a compound (8.2) wherein $X^2$ is I).

In Step D, the amine (8.2) is hydrolyzed via substantially the same process as described above for compounds (8.0) and (7.0), to give an amine of the formula (2.5).

Compounds of the formula (6.0) can be prepared from ketones of the formula (14.0) by the process shown in Reaction Scheme 8.

Reaction Scheme 8

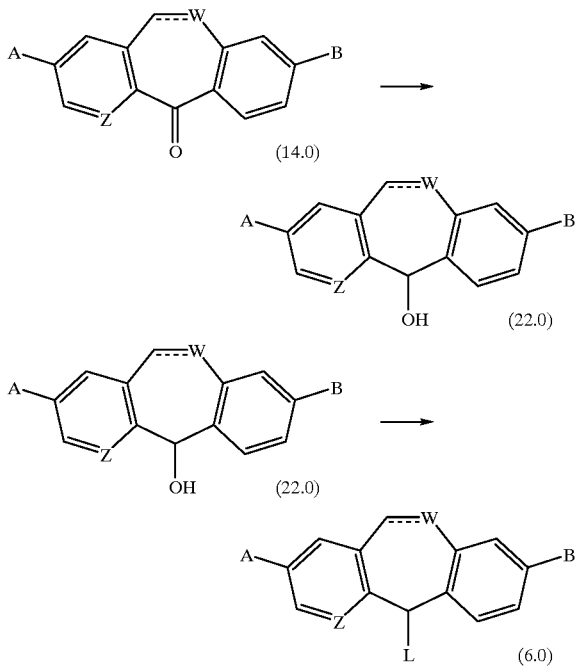

In the process of Reaction Scheme 8, the ketone (14.0) is reduced using a hydride reducing agent, preferably $LiAlH_4$, $NaBH_4$, $LiBH_4$ or $NaCNBH_3$, in a suitable solvent, such as THF, $Et_2O$, or a $C_1$–$C_4$ alcohol, at a temperature of $-80°$ to $80°$ C., preferably at $-40°$ to $60°$ C., with the temperature and solvent used being selected in accordance with the particular reducing agent employed, to form the alcohol (22.0). In general, boron hydrides, such as $NaBH_4$ and $NaCNBH_3$, are used in conjunction with alcohol solvents at a temperature of $0°$ to $50°$ C., while the more reactive aluminum hydrides, such as $LiAlH_4$, are used in solvents such as THF or $Et_2O$ at a temperature of $-40°$ to $60°$ C.

The alcohol (22.0) is converted to a compound of formula (6.0). For preparing compounds of formula (6.0) wherein L is halo, the alcohol (22.0) is reacted with a halogenating agent, such as $PCl_3$, $PCl_5$, $POCl_3$, $SOCl_2$, $SOBr_2$, $I_2$, $PBr_3$, $PBr_5$, or a combination of $Ph_3P$ and either $I_2$ or $Br_2$. For preparing compounds of formula (6.0) wherein L is a group of the formula —OC(O)—$R^{40}$ or —OS(O)$_2R^{22}$, the alcohol (22.0) is reacted with an acid chloride of the formula $R^{40}C(O)Cl$ or an anhydride of the formula $R^{40}C(O)OC(O)R^{40}$, or a sulfonyl chloride of the formula $R^{22}S(O)_2Cl$, respectively, in the presence of a base, preferably a tertiary amine base.

Compounds of the formula (5.0) can be prepared via substantially the same methods described in PCT International Publication WO95/00497.

Reaction Scheme 12 describes the synthesis of 2-substituted piperazines wherein $R^2$ is H, alkyl, alkenyl, or alkynyl, as well as the synthesis of 2-substituted piperazines wherein $R^2$ is alkyl, alkenyl, or alkynyl which are substituted with substituent groups 1), 2), 3), 5), 6) and 4), wherein t=0, as defined above, with the exception that $R^6$ and $R^7$ can not be a group that is substituted with —C(O)$R^{14}$ or —SO$_2R^{14}$.

REACTION SCHEME 12

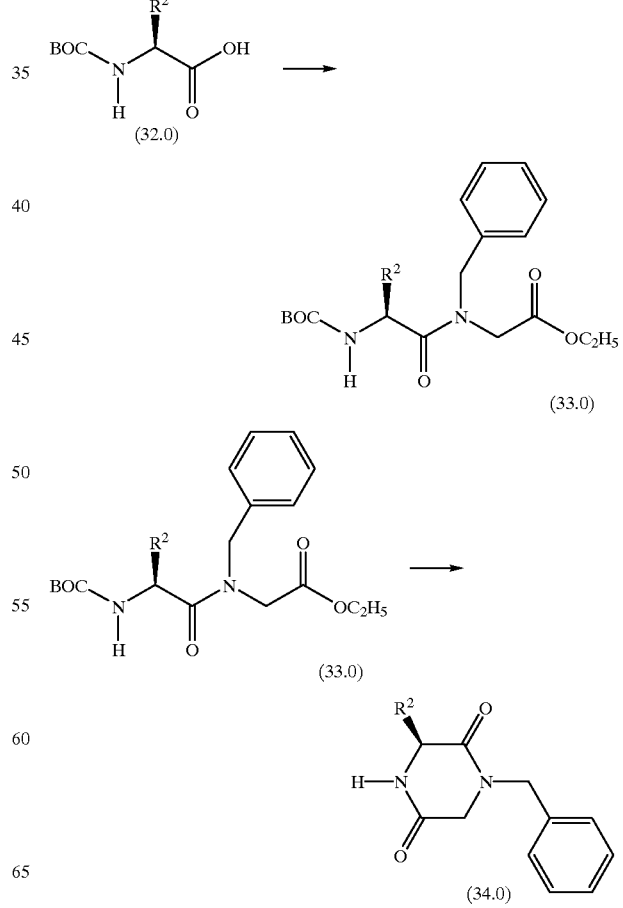

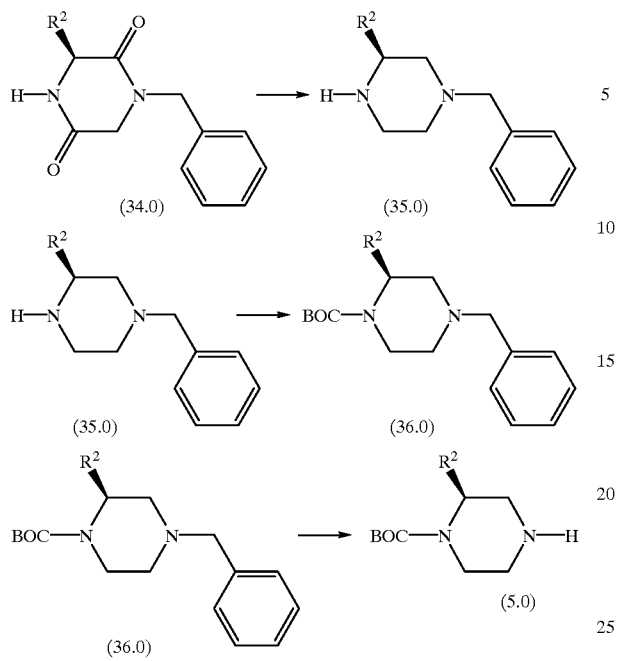

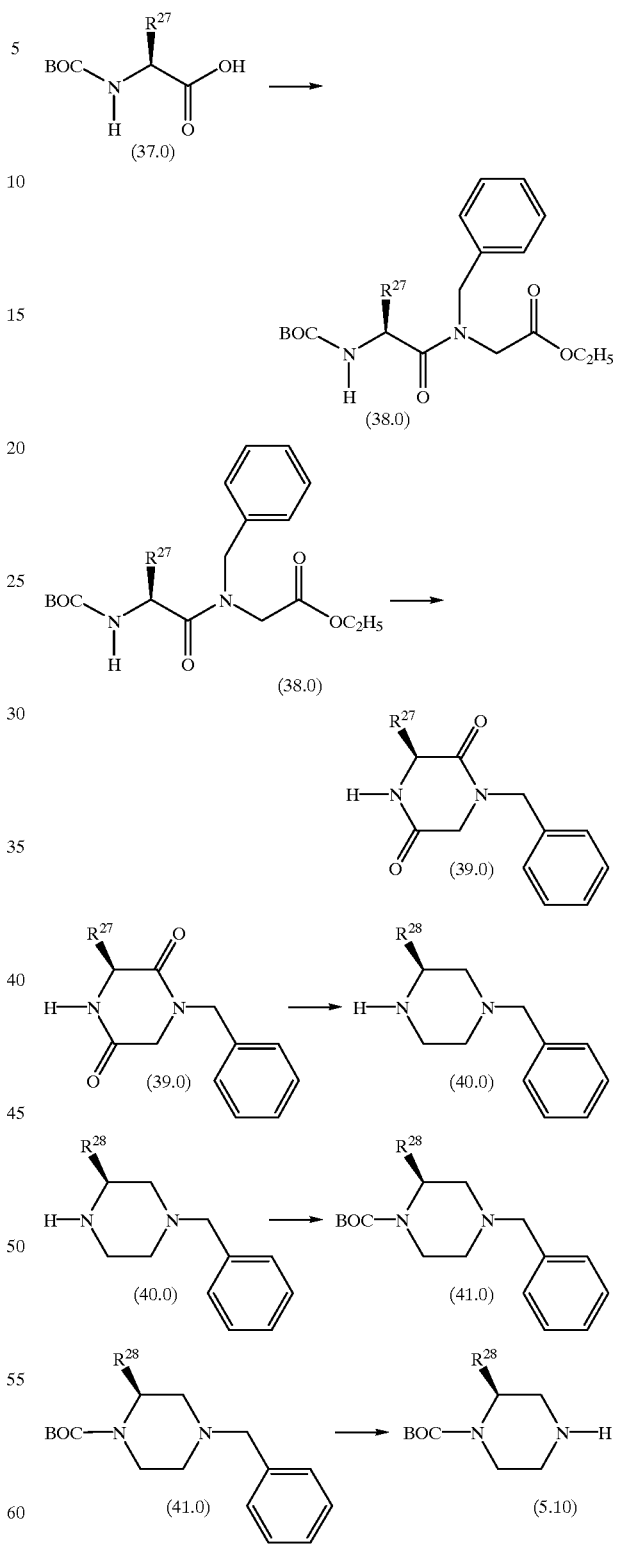

REACTION SCHEME 13

In Sheme 12, the starting BOC-protected amino acids (32.0) are available commercially or can be made by procedures well known in the art. The amino acids (32.0) can be coupled to N-benzylglycine ethyl ester using a coupling agent such as DCC or DEC in a suitable solvent (e.g., DMF, $CHCl_3$ or $CH_2Cl_2$) to produce a compound of Formula (33.0). Generally, this reaction is conducted at 0° to 35° C., preferably at about 25 °C.

The BOC protecting group of compound (33.0) is hydrolyzed via standard methods, such as treatment with an acid, preferably TFA or HCl, in a suitable solvent such as $CHCl_3$ or dioxane at 0° to 50° C., preferably at about 25° C. and the deprotected dipeptide is cyclized by treatment with base to produce the compound of formula (34.0).

Compound (34.0) is reduced using a hydride reducing agent, preferably $LiAlH_4$ in refluxing $Et_2O$ or THF to give a piperazine of formula (35.0). The piperazine (35.0) is protected with a BOC group by procedures well known in the art to give the compound of Formula (36.0).

The N-benzyl group of compound (36.0) is removed by catalytic hydrogenation (e.g., using PdWC and hydrogen gas under pressure of 1 to 100 psi, preferably at about 60 psi, to give the compound of Formula (5.0).

Compounds of Formula 5.0, wherein $R^2$ represents alkyl, alkenyl or alkynyl substituted with substituent groups 1), 3), 5) or 4), wherein t=0, wherein $R^6$ or $R^7$ are substituted with $-C(O)R^{14}$ or $-S(O)_2R^{14}$ are made according to the process shown in Reaction Scheme 13. Compounds of Formula 5.0, wherein $R^2$ represents $-C(O)NR^6R^7$ or $-C(O)OR^6$, or wherein $R^2$ represents alkyl, alkenyl or alkynyl substituted with a group 6), 7), 8), 9), 10), 11), 12), 13) or 4), where t=1 or 2, as defined above, are also made according to the process of Scheme 2.

In Reaction Scheme 13, the starting amino acids of formula (37.0), wherein $R^{27}$ is an alkyl, alkenyl or alkynyl group substituted by an —OH group or a —COOH group (or its corresponding ester) are available commercially or can be made by procedures known in the art. Compound (37.0) is reacted according to the procedures described for the first four steps of Reaction Scheme 12 to produce a compound of Formula (40.0) wherein $R^{28}$ is a hydroxy substituted alkyl, alkenyl or alkynyl group.

Compound (40.0) is then protected with a BOC group and then debenzylated according to the procedures described for steps 5 and 6 of Reaction Scheme 12 to produce a compound of Formula (5.10), i.e., a compound of formula (5.0) wherein $R^2$ is a hydroxy substituted alkyl, alkenyl or alkynyl group.

A compound of the formula (5.10) where $R^{28}$ is —CH$_2$OH can be oxidized to produce the corresponding carboxyl group, i.e., where $R^2$ is —COOH. This carboxyl group can then be esterified to produce compounds wherein $R^2$ is —C(O)OR$^6$, or converted to an amide to produce compounds wherein $R^2$ is —C(O)NR$^6$R$^7$ by procedures well known in the art.

The hydroxy group of $R^{28}$ of a compound of formula (5.10) can be converted to a leaving group, such as chloro, mesyloxy or tosyloxy, by techniques well known in the art. The leaving group can then be displaced by various nucleophiles, to produce other compounds of formula (5.0) For example, reaction with: an organometallic reagent to produce a compound where $R^2$ is substituted by a substituent 1); a thiol to produce a compound where $R^2$ is substituted by 4) where t=0; a sulfenyl reagent to produce a compound where $R^2$ is substituted by 4) where t=1; a sulfinyl reagent to produce a compound where $R^2$ is substituted by 4) where t=2, or by a substituent 10); an amine to produce a compound where $R^2$ is substituted by 5); or an alcohol to produce a compound where $R^2$ is substituted by 3). The hydroxy group on $R^{28}$ of compound (5.10) can also be: acylated, e.g. with a suitable chloroformate compound, to produce a compound (5.0) wherein $R^2$ is substituted by 8) or 9), respectively; or alkylated to produce a compound (5.0) wherein $R^2$ with is substituted by 3). When $R^{28}$ is alkyl having more than one carbon atom, or alkenyl or alkynyl, the hydroxy group can be oxidized, as discussed above, to produce the corresponding carboxyl group (i.e., substituent 13) wherein $R^6$ is H. This carboxyl group can be esterified to produce compounds wherein substituent 13) is —C(O)OR$^6$ wherein $R^6$ is other than H, or converted to amides to produce $R^2$ with a 12) substituent, by procedures well known in the art. When the leaving group is displaced by an amine (e.g., HNR$^6$R$^7$) to produce a substituent 5) as described above, for those substituents wherein at least one of $R^6$ or $R^7$ is H, the resulting amine substituent 5) can subsequently be converted to $R^2$ substituted by 6), 7) or 11) by reacting, with an acyl halide, a carbamyl halide or a sulfonyl halide, respectively, by procedures well known in the art.

Compounds of the formula (5.1), (i.e., racemates of compounds of the formula (5.0) wherein $R^2$ is —C(O)NR$^6$R$^7$), can be prepared from 2-piperazinecarboxylic acid via the process shown in Reaction Scheme 9.

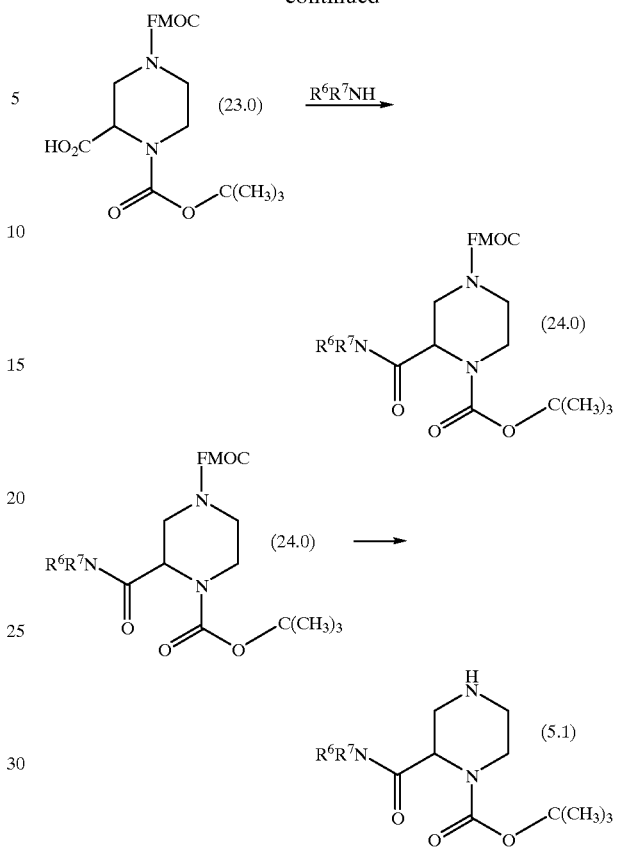

In the process of Reaction Scheme 9, 2-piperazine carboxylic acid is treated with FMOC-Cl in the presence of a hydroxide base, preferably NaOH or KOH, in a suitable solvent, such as a mixture of dioxane and water, then with BOC-ON under substantially the same conditions to form the differentially protected compound (23.0).

Compound (23.0) is reacted with an amine of the formula $R^6R^7NH$, wherein $R^6$ and $R^7$ are as defined above, in the presence of DEC or DCC in a suitable solvent, such as DMF or CH$_2$Cl$_2$.

Compound (24.0) is selectively deprotected by treating with TBAF or piperidine in a suitable solvent, such as DMF, to form a compound of the formula (5.1).

Compounds of the formula (5.2), wherein E is —OR$^6$ or —NR$^6$R$^7$, (i.e., racemates of compounds of the formula (5.0) wherein $R^2$ is a methyl group substituted by a group of the formula —C(O)OR$^6$ or —C(O)NR$^6$R$^7$), can be prepared via the process shown in Reaction Scheme 10.

Reaction Scheme 9

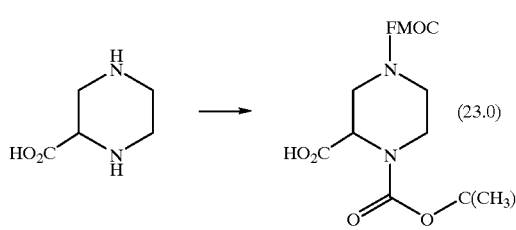

Reaction Scheme 10

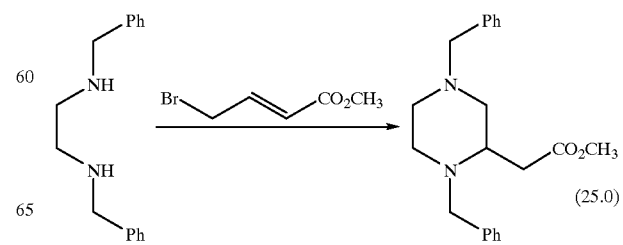

-continued

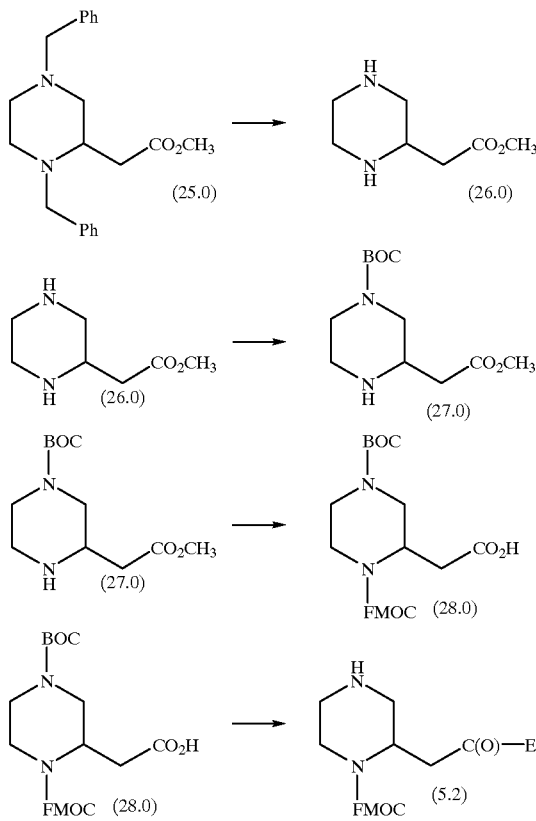

In the process of Reaction Scheme 10, N,N'-dibenzylethylenediamine is reacted with methyl 4-bromocrotonate and a tertiary amine base, such as Et$_3$N, in a suitable solvent, such as toluene, to form the N,N'-dibenzylpiperazine derivative (25.0).

Compound (25.0) is hydrogenated over a catalyst, such as Pd/C, to form piperazine derivative (26.0). The 4-amino group of compound (26.0) is then protected with a suitable amine protecting group, such as a BOC group to form compound (27.0).

Compound (27.0) is hydrolyzed using a hydroxide base, such as NaOH or KOH, and the free amino group is protected as the FMOC derivative using FMOC-Cl to form compound (28.0).

Compound (28.0) is reacted with an amine of the formula R$^6$R$^7$NH using a coupling agent, such as DEC, in a suitable solvent, such as CH$_2$Cl$_2$ or DMF, then deprotected using TBAF in DMF to form a compound of the formula (5.2), wherein E is —NR$^6$R$^7$. Alternatively, compound (28.0) is esterified by reacting with cyanuric fluoride in the presence of a tertiary amine base to form an acid fluoride which is reacted with an alcohol of the formula R$^6$OH, then deprotected by treating with TBAF or piperidine in DMF to form a compound of the formula (5.2) wherein E is —OR$^6$.

Halide compounds of the formula (13.0) can be prepared as the racemates (13.1), wherein X$^1$ and R$^2$ are as defined above, [except for compounds where R$^2$ is alkyl, alkenyl or alkynyl substituted by a substituent selected from 6), 7), 8), 9), 10), 11), 12), 13) or 4), wherein t=1 or 2], via the process shown in Reaction Scheme 11.

Reaction Scheme 11

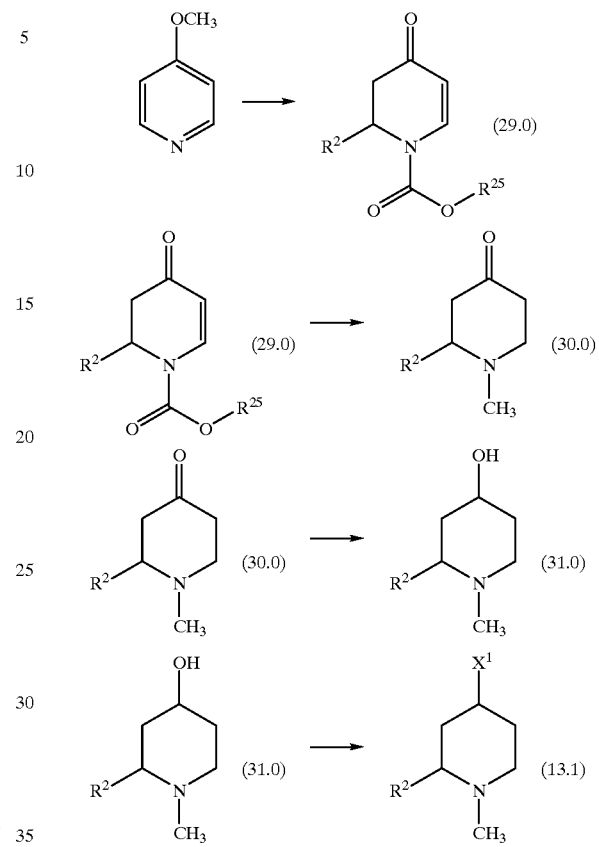

In the process of Reaction Scheme 11, 4-methoxypyridine is reacted with a Grignard reagent of the formula R$^2$MgX$^1$, wherein R$^2$ and X$^1$ are as defined above, or alternatively with an organolithium compound of the formula R$^2$Li, wherein R$^2$ is as defined above, and with a chloroformate of the formula R$^{25}$OC(O)Cl, wherein R$^{25}$ is phenyl or benzyl, to form a compound of the formula (29.0), wherein R$^2$ and R$^{25}$ are as defined above. The reactions are carried out via substantially the same procedures as described in Comins, et al., Tet. Lett., 27, (38) 4549–4552 (1986).

Compound (29.0) is converted to a compound of the formula (30.0). For compounds of the formula (29.0) wherein R$^{25}$ is benzyl, this transformation comprises hydrogenation of compound (29.0) using a suitable catalyst, such as Pd/C, followed by N-methylation using a suitable methylating agent, such as methyl iodide, in the presence of a base, such as NaH, to form the compound (30.0). Compounds of the formula (29.0) wherein R$^{25}$ is phenyl, are converted by hydrolysis of the phenylcarbamate using either aqueous acid or base to form the free amine, which is methylated, e.g. using methyl iodide and NaH, then reduced, e.g. by hydrogenation using a suitable catalyst, such as Pd/C, to form the compound (30.0).

Compound (30.0) is reduced using a hydride reducing agent, such as NaBH$_4$ or NaCNBH$_3$, to form the alcohol (31.0). The alcohol (31.0) is then converted to the halide (13.1) by treating with a halogenating agent, such as PCl$_3$, PCl$_5$, POCl$_3$, SOCl$_2$, SOBr$_2$, I$_2$, PBr$_3$, PBr$_5$, or a combination of Ph$_3$P and either I$_2$ or Br$_2$.

Optically active compounds of the formula (13.0) can be prepared via substantially the same process as described above for compounds of the formula (13.1) by carrying out a resolution step at a suitable intermediate in the process. For example, resolution of a compound of the formula (30.0) using an suitable resolving agent, such as a chiral acid, would give compounds of the formula (31.1) and (31.2), wherein $R^2$ is as defined above. The compound (31.1) could then be carried through the remaining steps of Reaction Scheme 11 to form a compound of the formula (13.0).

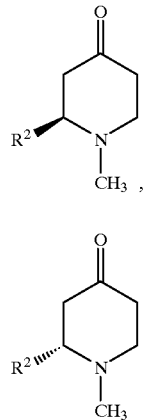

Compounds of the formula (17.0) and (19.0) are known in the art or can readily be prepared by standard methods.

An alternative method for preparing compounds of the formula (1.1), i.e., compounds of formula (1.0) wherein X is N, is shown in Reaction Scheme 14.

Reaction Scheme 14

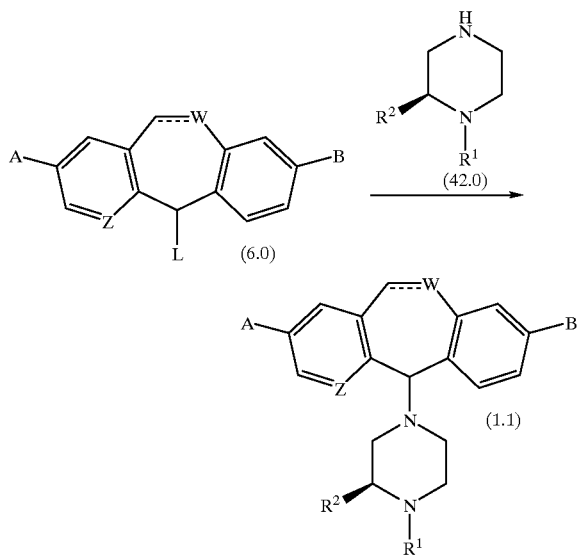

In Reaction Scheme 14, a compound of the formula (6.0) is reacted with a compound of formula (42.0), wherein $R^1$ and $R^2$ are as defined above for compound (1.0), in a suitable solvent, such as THF, in the presence of a base, such as a tertiary amine base or DBU, with DBU being preferred, to form a compound of formula (1.1).

Compounds of formula (42.0) are prepared as shown in Reaction Scheme 15.

Reaction Scheme 15

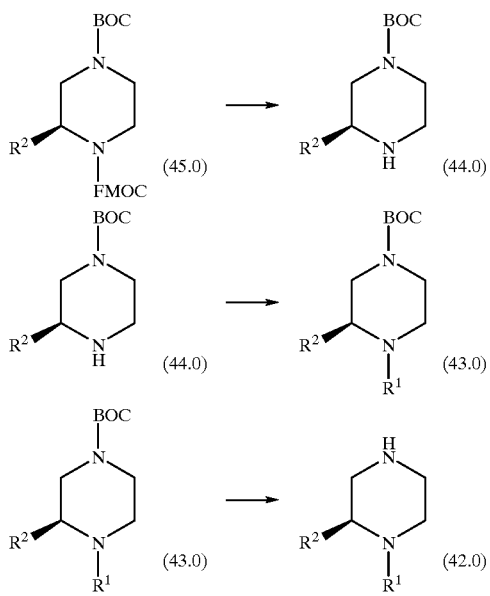

In Reaction Scheme 15, compound (45.0), wherein $R^2$ is as defined above for compound (1.0), the FMOC protecting group is selectively deprotected, e.g. by reacting with TBAF or piperidine in a suitable solvent, such as DMF, to form a compound of formula (44.0), which is then converted to a compound of formula (43.0) via substantially the same methods as described above for conversion of compounds of formula (2.0) into compounds of formula (1.0). Compound (43.0) is then deprotected, e.g. by reacting with an acid, such as TFA, in a suitable solvent, such as $CH_2Cl_2$, to form a compound of the formula (42.0).

Compounds of the formula (45.0) can be prepared via substantially the same procedures as described above for preparation of compounds of the formula (24.0), (28.0), by switching the order in which the protecting groups BOC and FMOC are applied, or by similar procedures as those described above for preparing compounds of formula (5.0) by adding additional protection/deprotection steps as necessary.

An encoded combinatorial library of compounds of formula (1.0), wherein X is N and $R^2$ has a suitable functional group, can be prepared using combinatorial methods on a solid phase as described in WO 94/08051 (published Apr. 14, 1994), and can be prepared as described in Reaction Scheme 16 below.

Reaction Scheme 16

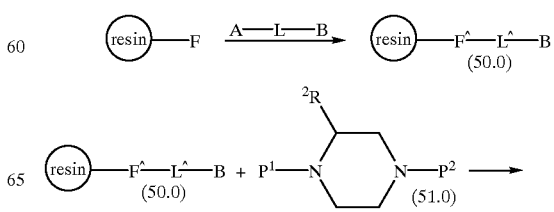

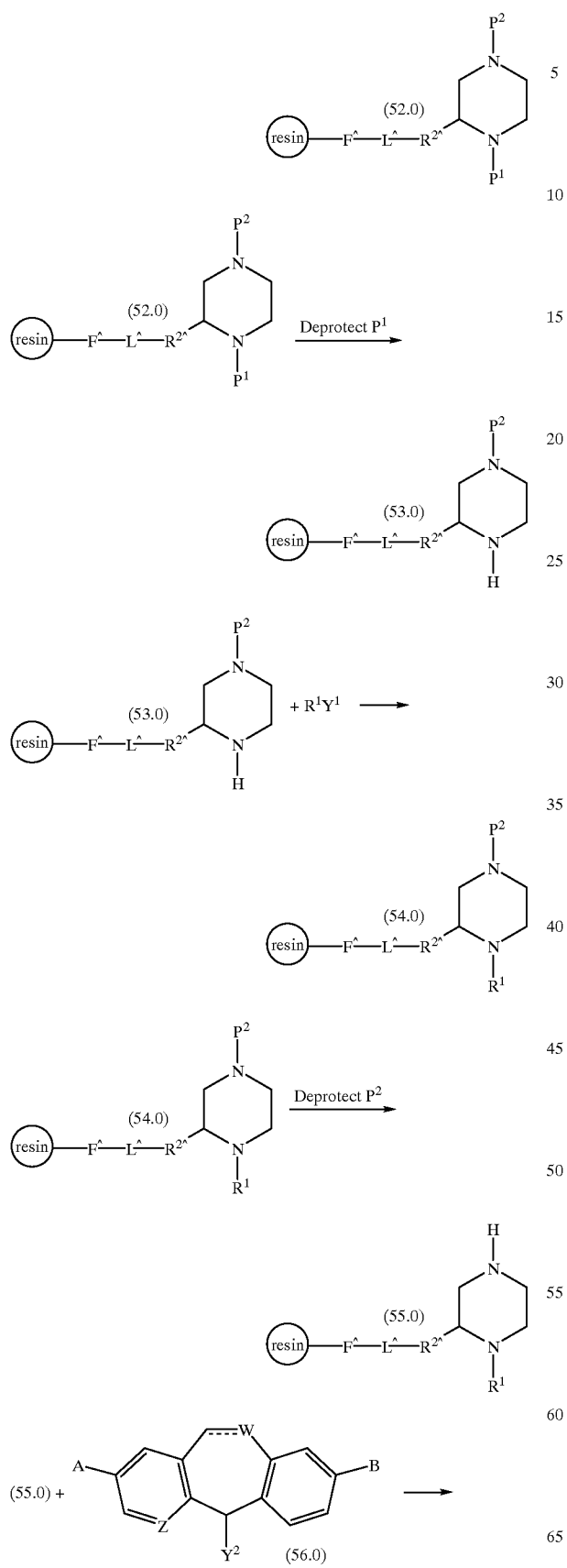
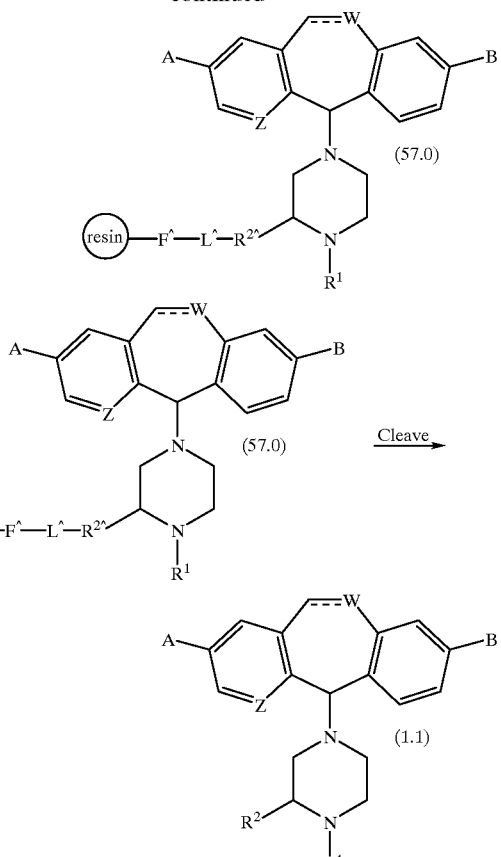

In Scheme 16, a resin, e.g. (resin)-F, is selected which contains a functional group, (-F), which can couple, or form a covalent bond with a suitable linker (A-L-B). Suitable functional (-F) groups include primary and secondary amines, hydroxy, thiol, carboxylic acid, halide and the like. The linker (A-L-B) can be any compound having (a) a complementary functional "A-" group (e.g. amine, hydroxy, thiol, carboxylic acid, halide and the like) which can couple, or form a covalent bond with (resin)-F; (b) a functional "-B" group (e.g. hydroxy, primary or secondary amine, thiol, carboxylic acid and the like) capable of forming a covalent bond with a suitable functional group in $R^2$ of a substituted, N-protected piperazine (51.0), such as an amide or carboxylic acid group in $R^2$; and (c) an organic or inorganic moiety "L" capable of having bound to it functional groups "A" and "B". Representative linkers include, but are not limited to 4-(bromomethyl)-3-nitrobenzoic acid and 4-(hydroxymethyl)phenol. The linker can be coupled to (resin)-F in a suitable solvent (e.g. DCM or methanol), optionally in the presence of a catalyst suitable for the particular coupling reaction.

Reagents and reaction conditions for protecting and deprotecting compounds is well known, as described, for example, in T. W. Greene and P. Wuts, Protective Groups in Organic Synthesis, 2nd Ed., Wiley Interscience, N.Y. 1991, 473 pages. In addition to having a suitable functional group in its $R^2$ group, piperazine (51.0) has protecting groups, $P^1$ and $P^2$ orthogonal to each other and to the linker. Suitable protecting groups include but are not limited to BOC, FMOC, CBZ, allyloxycarbonyl (ALLOC), benzyl, o-nitrophenyl and the like. The resin/linker (50.0) can be coupled to N-protected piperazine (51.0) in the presence of a suitable solvent, optionally in the presence of a catalyst suitable for the particular coupling reaction to give the coupled piperazine (52.0). The "^" in moieties such as $R^{2^}$, $F^$ and $L^$ indicate that at least one functional group in that moiety is covalently bonded to another functional group.

Protecting group P¹ can be removed by treatment with a suitable deprotecting agent or process, including but not limited to TFA, piperidine, hydrogenolysis, photolysis and the like to give partially deprotected piperazine (53.0). Piperazine (53.0) can then be reacted with compound R¹Y¹, wherein R¹ is as defined before and Y¹ is a suitable leaving group, in a suitable solvent, optionally in the presence of a catalyst suitable for the particular reaction, to give partially protected piperazine (54.0). Compound (54.0) can be deprotected as described above to give deprotected compound (55.0). Compound (55.0) can be alkylated with compound (56.0), wherein A, B, W and Z are as defined for formula 1.0, and Y² is a suitable leaving group, to give compound (57.0).

Compound (1.1) can be prepared by cleaving the coupling between the linker and R²^ using a suitable reagent or process suitable for the particular bond coupling,.e.g. photolysis, acidolysis, hydrolysis and the like.

In the above processes, it is sometimes desirable and/or necessary to protect certain R¹ and R² groups during the reactions. Conventional protecting groups are operable as described in Greene, T. W., "protective Groups In Organic Synthesis," John Wiley & Sons, New York, 1981. For example, see the groups listed in Table 1 on page 60 of WO 95/10516 (published Apr. 20, 1995).

Compounds useful in this invention may be prepared by the methods disclosed in WO 95/10516, and by the methods described in the examples below. The following preparative examples should not be construed as limiting the scope of the disclosure. Alternative mechanistic pathways and analogous structures within the scope of the invention may be apparent to those skilled in the art.

PREPARATIVE EXAMPLE 1

Step A:

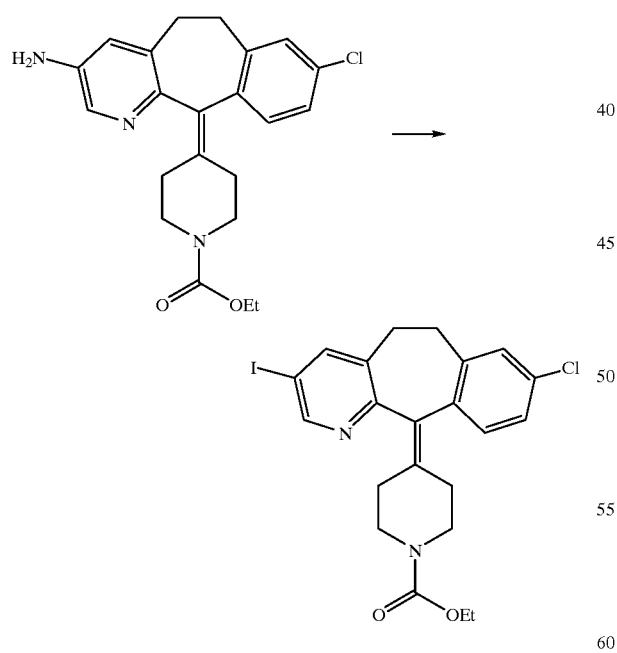

Combine 6 g (15.11 mmol) of the title compound of Preparative Example 47B, of WO 95/10516, and benzene, and add 2.3 g (9.06 mmol) of iodine. Heat the mixture at reflux for 3 hours, cool, then dilute with 50 mL of CH₂Cl₂. Wash the organic phase with 5% NaHSO₃(aqueous) (3×80 mL), then with 1M NaOH (aqueous) (2×80 mL), and dry over MgSO₄. Concentrate to a residue chromatograph (silica gel, 30% EtOAc/hexanes), to give 3.2 g (42% yield) of the product iodo compound. MS, MH+=509

Step B:

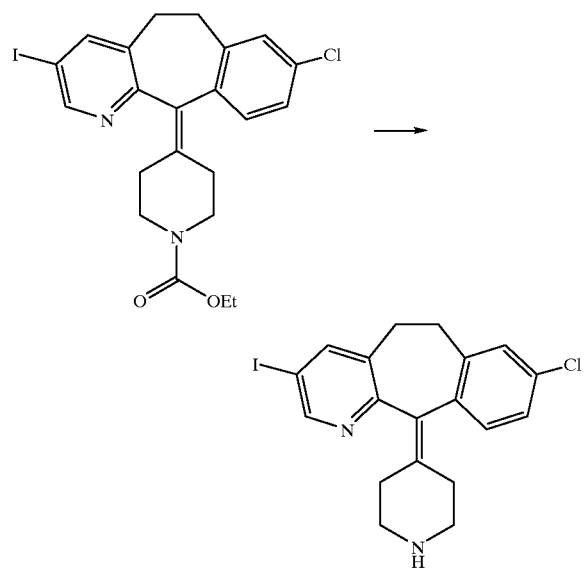

The product of Step A is hydrolyzed via substantially the same procedure as described in Example 358, Step A, of WO 95/10516, to give the iodoamine product in 89% yield.

PREPARATIVE EXAMPLE 2

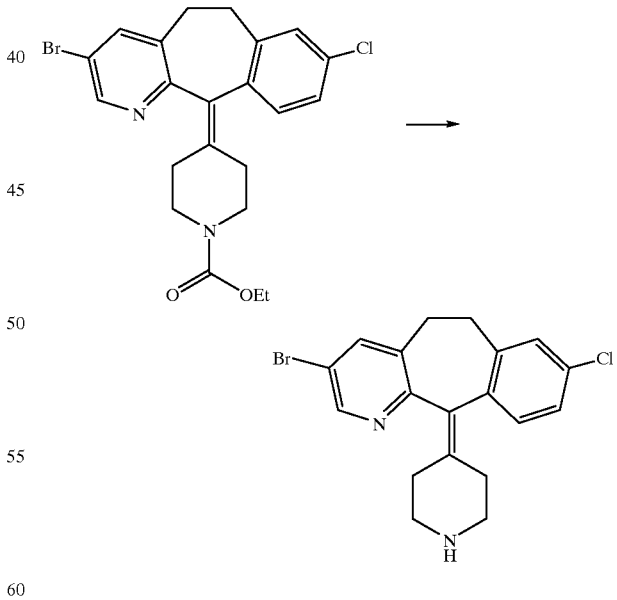

The product of Preparative Example 47, Step C, of WO 95/10516, (2.42 g) is hydrolyzed via substantially the same procedure as described in Example 358, Step A, of WO 95/10516, to give 1.39 g (69% yield) of the bromoamine product.

PREPARATIVE EXAMPLE 3

Step A:

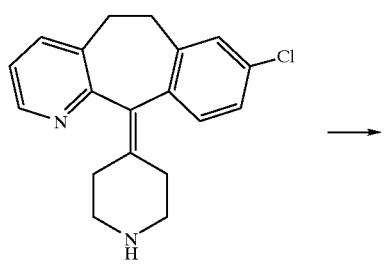
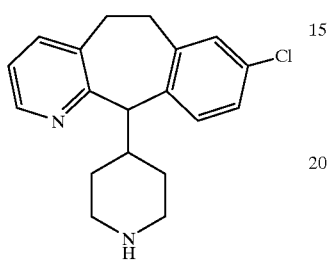

Combine 82.0 g (0.26 mole) of the product of Preparative Example 1, Step G, of WO 95/10516, and 1 L of toluene, then add 20.06 g (0.53 mole) of LiAlH$_4$ and heat the reaction mixture at reflux overnight. Cool the mixture to room temperature and add ~1 L of Et$_2$O, followed by dropwise addition of saturated Na$_2$SO$_4$ (aqueous) until a precipitate forms. Filter and stir the filtrate over MgSO$_4$ for 30 minutes, then concentrate in vacuo to give the product compound in 83% yield. Mass Spec.: MH$^+$=313

PREPARATIVE EXAMPLE 4

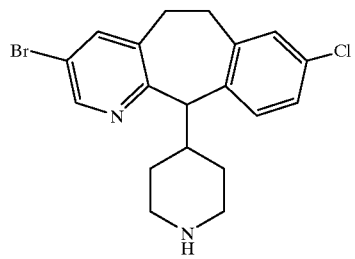

Step A:

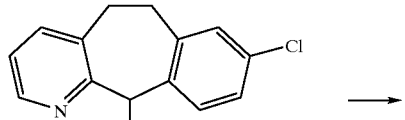

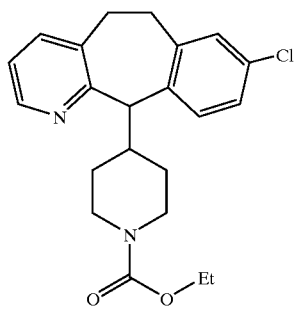

Combine 24.32 g (74.9 mmol) of the Product from Preparative Example 3, Step A, 500 mL of toluene, 83 mL of Et$_3$N and 65.9 mL of ethyl 5 chloroformate and heat the mixture at reflux overnight. Cool to 25° C., pour into 200 mL of water and extract with EtOAc. Dry the extract over MgSO$_4$, concentrate in vacuo to a residue and chromatograph (silica gel, 50% EtOAc/hexane) to give 15 g of the product compound. MS: MH$^+$=385.

Step B:

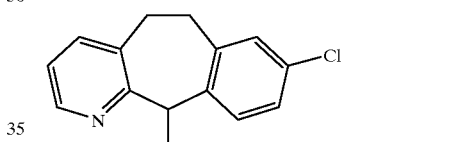
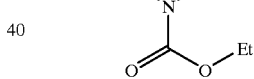

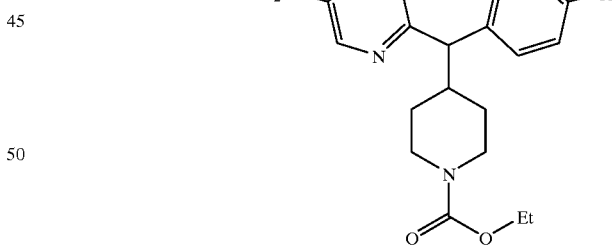

Dissolve 3.2 g (10.51 mmol) of tetra-n-butylammonium nitrate in 25 mL of CH$_2$Cl$_2$ and add 2.2 g (10.51 mmol, 1.5 mL) of TFAA. Cool to 0° C. and add the mixture (via cannula) to a solution of 3.68 g (9.56 mmol) of the product of Step A in 50 mL of CH$_2$Cl$_2$ at 0° C., then stir at 0° C. for 3 hours. Allow the mixture to warm to 25° C. while stirring overnight, then extract with saturated NaHCO$_3$ (aqueous) and dry over MgSO$_4$. Concentrate in vacuo to a residue and chromatograph (silica gel, 30% EtOAc/hexane) to give 1.2 g of the product compound. MS: MH$^+$=430.

Step C:

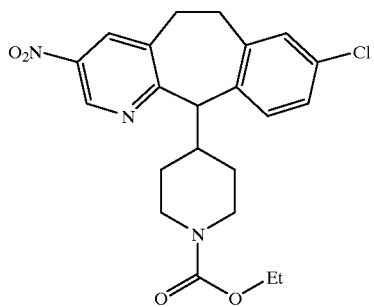

Combine 2.0 g (4.7 mmol) of the Product of Step B and 150 mL of 85% EtOH (aqueous), add 2.4 g (42 mmol) of Fe filings and 0.24 g (2.1 mmol) of $CaCl_2$, and heat at reflux for 16 hours. Filter the hot mixture through a bed of celite®, wash the celite® with hot EtOH. Concentrate the filtrate in vacuo to give a 100% yield of the product compound. MS: $MH^+=400$.

Step D:

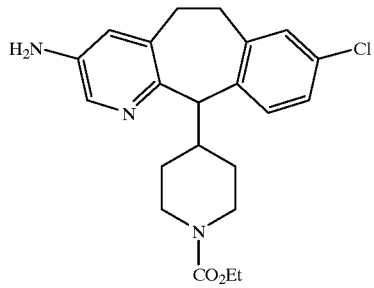

Combine 2.0 g (5.2 mmol) of the Product of Step C and 20 mL of 48% HBr, cool the mixture to −5° C. Stir the mixture at −5° C. for 15 minutes and slowly add a solution of 1.07 g (15.5 mmol) of $NaNO_2$ in 10 mL of water. Stir for 45 minutes, then quench with 50% NaOH (aqueous) to pH ~10. Extract with EtOAc, dry the combined extracts over $MgSO_4$ and concentrate in vacuo to give the product compound. MS: $MH^+=465$ Step E:

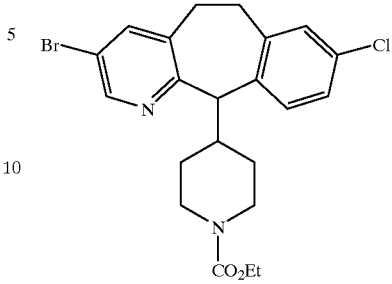

Hydrolyze 4.0 g of the Product of Step D via substantially the same process as described for Example 358, Step A, of WO 95/10516, to give 1.39 g of the product compound. MS: $MH^+=392$

PREPARATIVE EXAMPLE 5

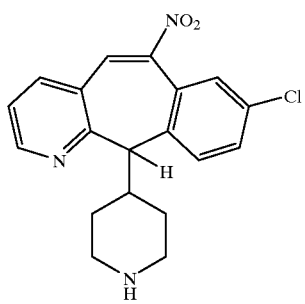

Step A:

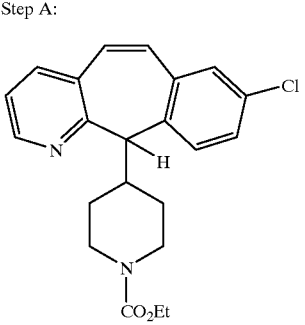

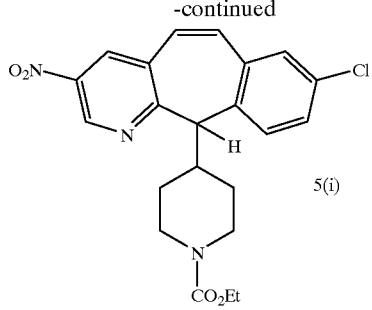

5(i)

+

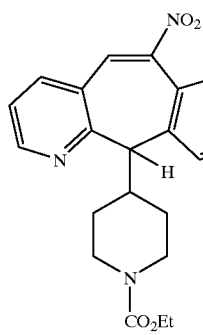

5(ii)

Combine 14.95 g (39 mmol) of the Product of Preparative Example 34A, of WO 95/10516, and 150 mL of $CH_2Cl_2$, then add 13.07 g (42.9 mmol) of $(n\text{-Bu})_4NNO_3$ and cool the mixture to 0° C. Slowly add (dropwise) a solution of 6.09 mL (42.9 mmol) of TFAA in 20 mL of $CH_2Cl_2$ over 1.5 hours. Keep the mixture at 0° C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 5(i) and 5(ii), respectively. MS (5(i)): $MH^+=428.2$; MS (5(ii)): $MH^+=428.3$ Step B:

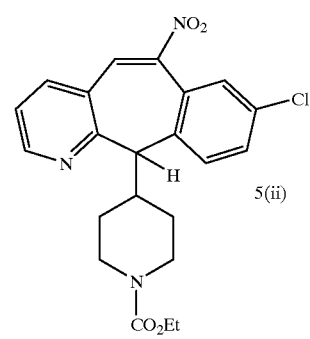

5(ii)

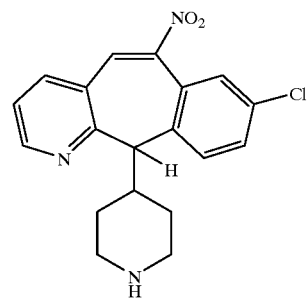

The compound 5(ii) from Step A (0.20 g) is hydrolyzed via substantially the same procedure as described for Example 358, Step A, of WO 95/10516, to give 0.16 9 of the product compound.

Using the starting compound indicated and substantially the same procedure as described in Preparative Example 5, Step B, the following product compounds are prepared:

| Starting Compound | Compound | Analytical Data |
|---|---|---|
| Preparative Example 5, Step A, compound 5(i) | Preparative Example 5A | — |
| Preparative Example 6, Step B, compound 6(i) | Preparative Example 5C | MS: $MH^+= 466.9$ |

PREPARATIVE EXAMPLE 6

Step A:

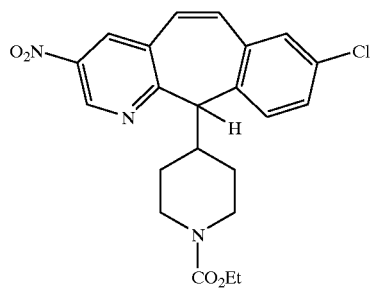

→

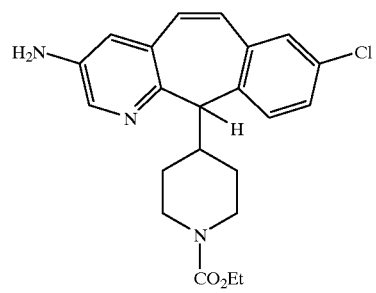

Combine 22.0 g (51.4 mmol) of the product 5(i) from Preparation 5, Step A, 150 mL of 85% EtOH (aqueous), 25.85 g (0.463 mole) of Fe powder and 2.42 g (21.8 mmol) of $CaCl_2$, and heat at reflux overnight. Add 12.4 g (0.222 mole) of Fe powder and 1.2 9 (10.8 mmol) of $CaCl_2$ and heat at reflux for 2 hours. Add another 12.4 g (0.222 mole) of Fe powder and 1.2 g (10.8 mmol) of $CaCl_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, $MeOH/CH_2Cl_2$ gradient) to give 16.47 g of the product compound.

Step B:

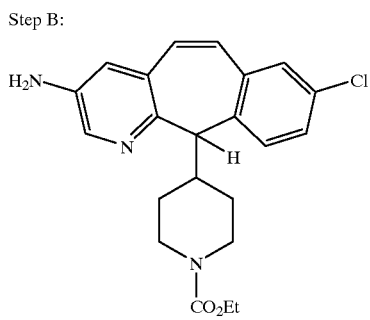

→

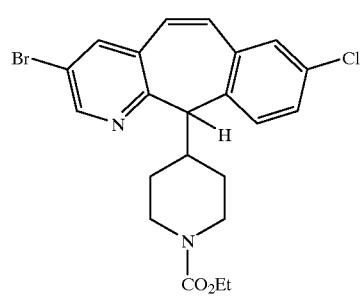

6(i)

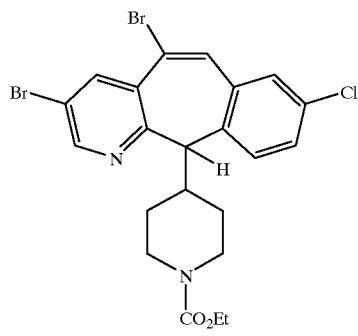

6(ii)

Combine 16.47 g (41.4 mmol) of the product compound from Preparative Example 6, Step A, and 150 mL of 48% HBr (aqueous) and cool to −3° C. Slowly add (dropwise) 18 mL of bromine, then slowly add (dropwise) a solution of 8.55 g (0.124 mole) of $NaNO_3$ in 85 mL of water. Stir for 45 minutes at −3° to 0° C., then adjust to pH=10 by adding 50% NaOH (aqueous). Extract with EtOAc, wash the extracts with brine and dry the extracts over $Na_2SO_4$. Concentrate to a residue and chromatograph (silica gel, EtOAc/hexane gradient) to give 10.6 g and 3.28 g of the two product compounds 6(i) and 6(ii), respectively. MS (6(i)): $MH^+$= 461.2; MS (6(ii)): $MH^+$=539

PREPARATIVE EXAMPLE 7

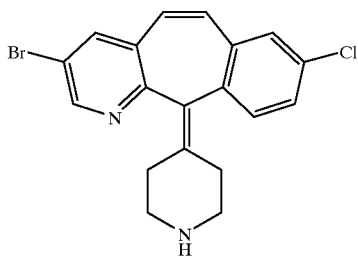

Step A:

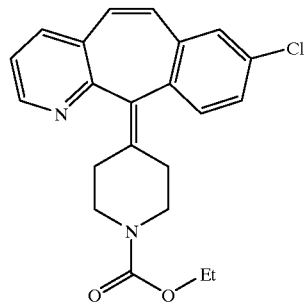

→

-continued

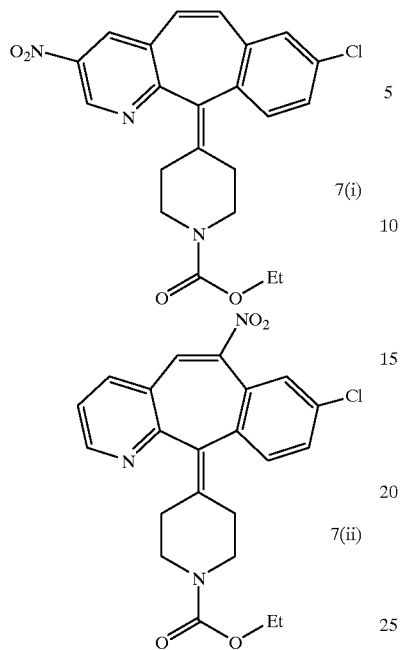

7(i)

7(ii)

Combine 1.07 g (3.52 mmol) of tetrabutylammonium nitrate, 4 mL of anhydrous $CH_2Cl_2$ and 0.743 g (3.52 mmol) of TFAA, and add the resulting mixture to a solution of 1.22 g (3.20 mmol) of the title compound of Preparative Example 37, of WO 95/10516, in 8 mL of anhydrous $CH_2Cl_2$ at room temperature. Stir at room temperature overnight, then wash with 20 mL of saturated $NaHCO_3$ (aqueous) and 20 mL of brine, and dry over $MgSO_4$. Concentrate in vacuo and chromatograph the resulting residue (silica gel, EtOAc/hexane) to give 0.216 g of the product compound 7(i) and 0.27 g of the product compound 7(ii). MS: (7(i)) $MH^+$=426, m.p. (7(i)) 97.5°–99.2° C.

Step B:

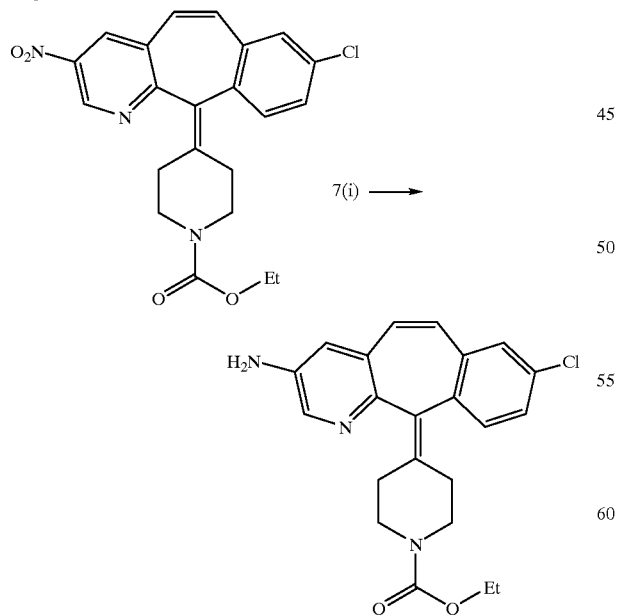

Reduce the product 7(i) from Step A via essentially the same procedure as described in Preparative Example 47, Step B, of WO 95/10516, to give the product compound. MS: $MH^+$=396

Step C:

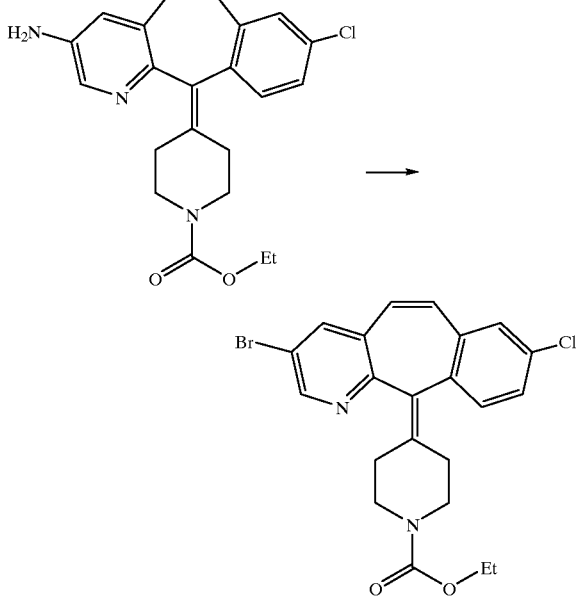

React the product from Step B with HBr and $Br_2$ via essentially the same procedure as described in Preparative Example 47, Step C, of WO 95/10516, to give the product compound. MS: $MH^+$ 32 459

Step D:

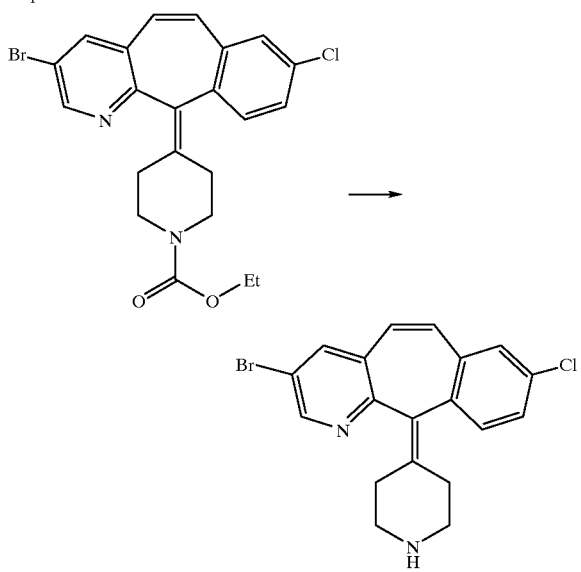

Hydrolyze 0.83 g of the product from Step C by combining the product with anhydrous EtOH and concentrated HCl and stirring at reflux. Cool the reaction mixture to about 0° C. and basify by adding KOH. Extract with $CH_2Cl_2$, dry the extract over $MgSO_4$, and concentrate in vacuo to give 0.56 g of the product compound. MS: $MH^+$=387

PREPARATIVE EXAMPLE 8

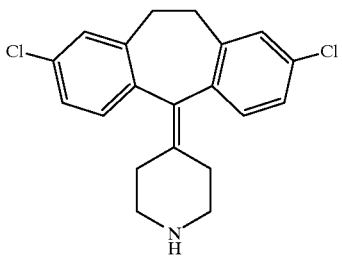

Step A:

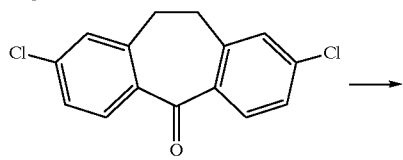

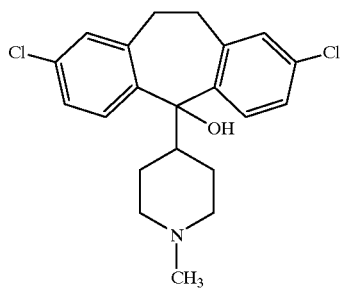

Combine 7.3 g (26.4 mmol) of the starting ketone (see *J. Med. Chem.*, 4238 (1992)) and 230 mL of THF and cool to 0° C. Add a solution of 32.2 mmol of N-methyl-piperidine-4-magnesium bromide in 26 mL of THF and stir at 0°–5° C. for 4 hours. Add 400 mL of EtOAc, wash with saturated NH$_4$Cl (aqueous), and dry over MgSO$_4$. Concentrate in vacuo to a residue, add ~200 mL of CH$_2$Cl$_2$ and stir for 0.5 hours. Filter to collect the resulting solid and concentrate the filtrate to a volume of ~100 mL and let sit at 5° C. for 18 hours. Filter and combine the solids to obtain a total of 7 g (19.4 mmol) of the product compound. m.p.=153.70°–158° C.; MS: (Cl) MH$^+$=376

Step B:

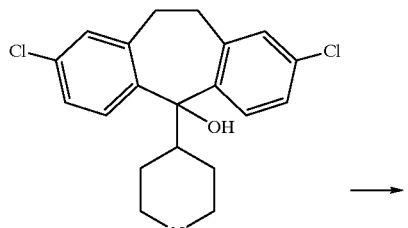

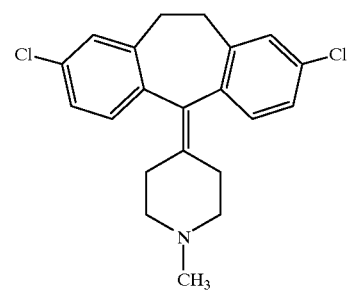

Combine 5 g of the product from Step A and 30 mL of TFA at ambient temperature and stir for 1 hour. Concentrate in vacuo to a residue, dissolve the residue in CH$_2$Cl$_2$ and wash with a saturated NaHCO$_3$ (aqueous). Concentrate in vacuo to give 4.64 g of the product compound. m.p.= 136.7°–138° C.; MS: (FAB) MH$^+$=358.1

Step C:

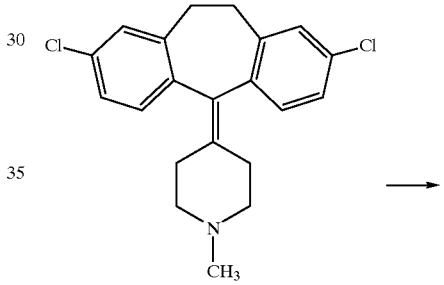

Combine 0.6 g (1.75 mmol) of the product of Step B and 25 mL of toluene, add 0.73 mL (5.27 mmol) of Et$_3$N and 1.34 mL (14 mmol) of ClCO$_2$Et, and heat to 80° C. for 2 hours. Add 0.7 mL more of ClCO$_2$Et, heat for 1 more hour, then cool to 25° C. and concentrate in vacuo to a residue. Dissolve the residue in EtOAc and wash with 1N NaOH (aqueous) followed by brine. Dry over MgSO$_4$, concentrate in vacuo to a residue and chromatograph (silica gel, 10% EtOAc/hexanes) to give 0.55 g of the product compound. MS: (FAB) MH$^+$=416.2

Step D:

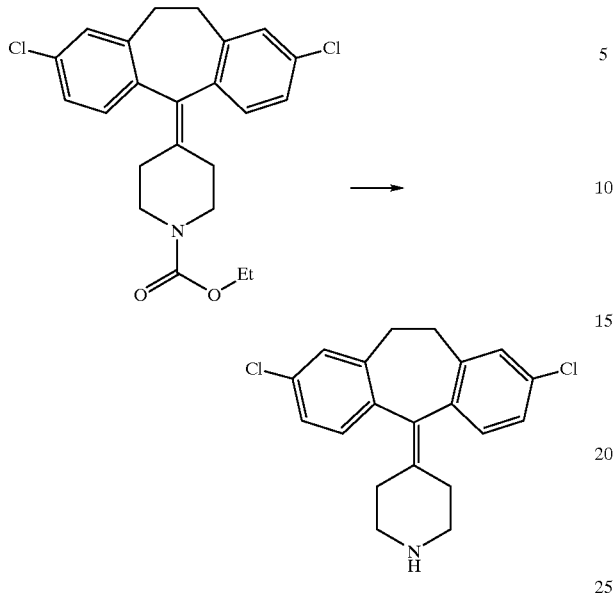

Dissolve 5 g (12.5 mmol) of the product of Step C in 30% HBr in HOAc and heat at 40° C. for 24 hours, then cautiously add the mixture to cold 25 % NaOH (aqueous). Extract with $CH_2Cl_2$ (3×100 mL), concentrate the extracts to a residue and chromatograph (silica gel, 5% to 30 % MeOH/$CH_2Cl_2$) to give 2.18 g of the product compound. m.p.=159.5°–160.8° C.; MS: (FAB) $MH^+$=344.1

PREPARATIVE EXAMPLE 9

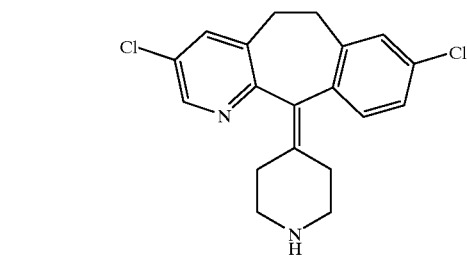

Step A:

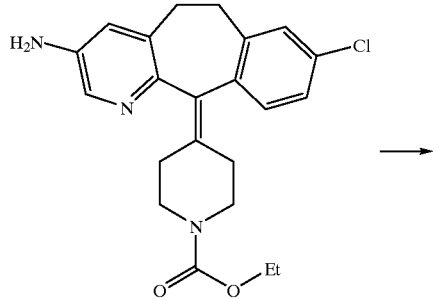

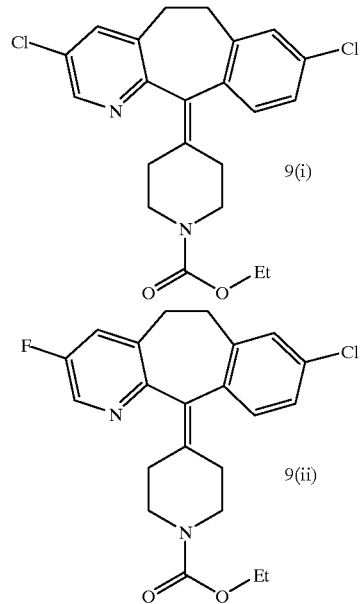

Combine 16.25 g (40.83 mmol) of the product of Preparative Example 47, Step B, of WO 95/10516, and a slurry of 7.14 g (61.11 mmol) of $NOBF_4$ in 100 mL of $CH_2Cl_2$ and stir the mixture for 3 hours. Add 100 mL of o-dichlorobenzene and heat for 5 hours, distilling the $CH_2Cl_2$ from the mixture. Concentrate in vacuo to a residue, add 200 mL of $CH_2Cl_2$ and wash with water (2×200 mL). Dry over $MgSO_4$, concentrate in vacuo to a residue, and chromatograph (silica gel, 20% EtOAc/hexane) to give 4.1 g of product compound 9(i) and 4.01 g of Product compound 9(ii). MS (9(i)): $MH^+$=418, MS (9(ii)): $MH^+$=401

Step B:

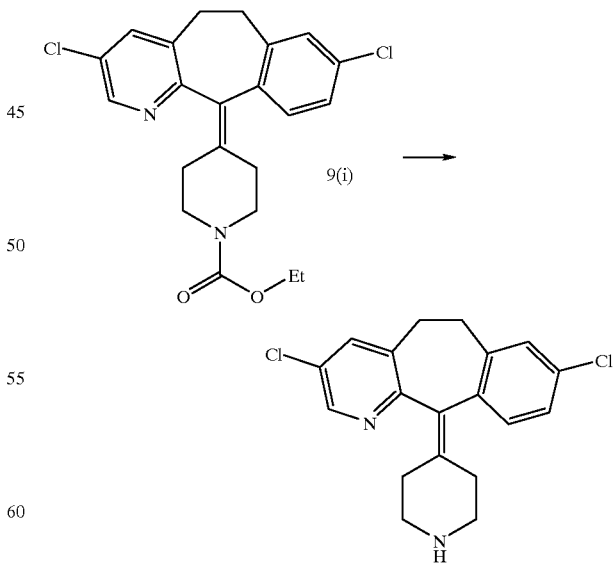

Hydrolyze the product 9 (i) from Step A via essentially the same process as described for Example 358, Step A, of WO 95/10516, to give the product compound. MS: $MH^+$=346

PREPARATIVE EXAMPLE 10

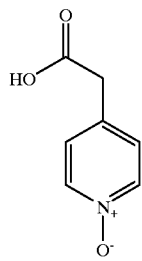

Step A:

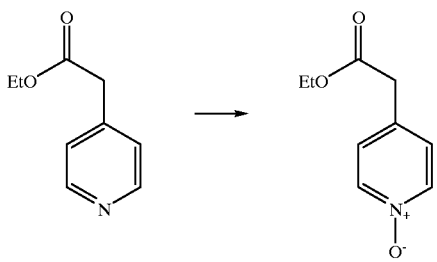

Combine 10 g (60.5 mmol) of ethyl 4-pyridylacetate and 120 mL of dry $CH_2Cl_2$ at −20° C., add 10.45 g (60.5 mmol) of MCPBA and stir at −20° C. for 1 hour and then at 25° C. for 67 hours. Add an additional 3.48 g (20.2 mmoles) of MCPBA and stir at 25° C. for 24 hours. Dilute with $CH_2Cl_2$ and wash with saturated $NaHCO_3$ (aqueous) and then water. Dry over $MgSO_4$, concentrate in vacuo to a residue, and chromatograph (silica gel, 2%–5.5% (10% $NH_4OH$ in MeOH)/$CH_2Cl_2$) to give 8.12 g of the product compound. MS: $MH^+$=182.15

Step B:

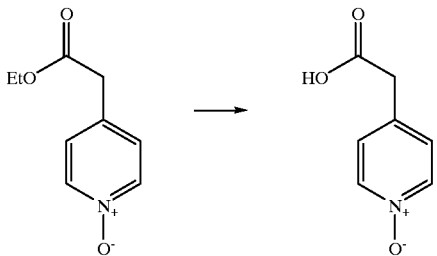

Combine 3.5 g (19.3 mmol) of the product of Step A, 17.5 mL of EtOH and 96.6 mL of 10% NaOH (aqueous) and heat the mixture at 67° C. for 2 hours. Add 2 N HCl (aqueous) to adjust to pH=2.37 and concentrate in vacuo to a residue. Add 200 mL of dry EtOH, filter through celite® and wash the filter cake with dry EtOH (2×50 ml). Concentrate the combined filtrates in vacuo to give 2.43 g of the title compound.

PREPARATIVE EXAMPLE 11

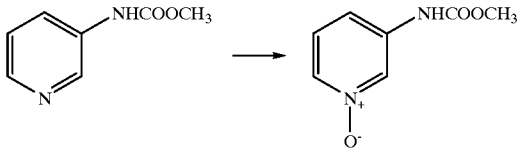

Combine 10 g (65.7 mmol) of 3-methoxycarbonyl- aminopyridine and 150 mL of $CH_2Cl_2$, cool to 0° C. and slowly add (dropwise) a solution of 13.61 g (78.84 mmol) of MCPBA in 120 mL of $CH_2Cl_2$ at 0° C. over a period of 1 hour. Stir the mixture at 25° C. for 5 days, then wash with saturated $NaHCO_3$ (aqueous), then water and dry over $MgSO_4$. Concentrate in vacuo to a residue and chromatograph (silica gel, 2%–5% (10% $NH_4OH$ in MeOH)/$CH_2Cl_2$) to give the product compound. MS: $MH^+$=169

PREPARATIVE EXAMPLE 12

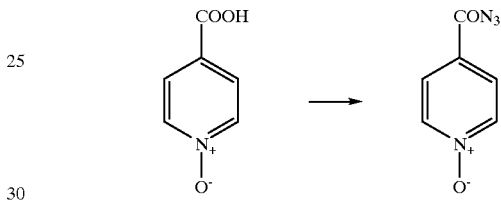

Combine 5 g (36.0 mmol) of isonicotinic acid 1-N-oxide and 150 mL of anhydrous DMF, add 5.5 mL (39.6 mmol) of $Et_3N$ and stir at 0° C. for 0.5 hours. Slowly add (dropwise) 8.5 mL (39.6 mmol) of diphenylphosphoryl azide at 0° C. over 10 minutes, stir at 0° C. for 1 hour and then at 25° C. for 24 hours (as generally described in Pavia, et al., *Journal of Medicinal Chemistry*, 33, 854–861 (1990). Concentrate in vacuo to a residue and chromatograph (silica gel, 0.5%–1% MeOH/$CH_2Cl_2$) to give 5.9 g of the product compound.

Using nicotinic acid 1-N-oxide and substantially the same procedure as described for Preparative Example 12 the following compound was prepared:

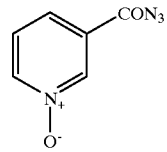

PREPARATIVE EXAMPLE 13

Step A:

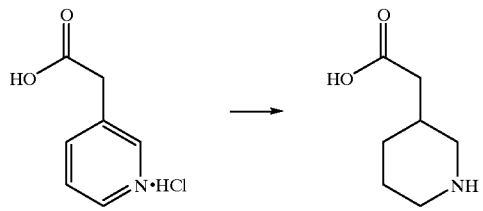

Hydrogenate 25 g (144 mmol) of 3-pyridylacetic acid hydrochloride for 144 hours using the procedure described in Preparative Example 15, of WO 95/10516, to give 20 g of the product compound. MS: MH⁺=144.

Step B:

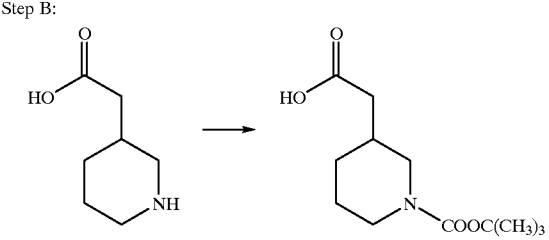

React 12 g (83.8 mmol) of the product of Step B for 148 hours using the procedure described in Preparative Example 13, Step B, of WO 95/10516, to give 17.5 g of the product compound. MS: MH⁺=244.25

PREPARATIVE EXAMPLE 14

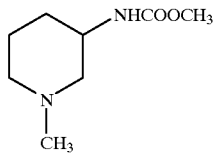

Combine 25 g (164.4 mmol) of methyl 3-pyridylcarbamate and 163.3 mL of 1 N HCl (aqueous), stir until all of the solid dissolves, then hydrogenate over 10% Pd/C at 25° C. at 55 psi for 220 hours. Filter, wash the solids with water and treat the combined filtrates with 150 mL of BioRad AG1X8 ion exchange resin (OH⁻). Filter, wash the resin with water and concentrate the filtrate to a volume of 100 mL. Add 16.43 mL (197.3 mmol) of 37% formalin and hydrogenate over 10% Pd/C at 25° C. at 55 psi for 89 hours. Filter, wash the solids with water and concentrate in vacuo to give 24.3 g of the title compound. MS: MH⁺=173.2

PREPARATIVE EXAMPLE 15

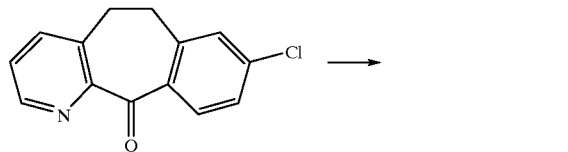

Cool 50.0 g (20.5 mmol) of 8-chloro-5,6-dihydro-11H-benzo[5,6]cyclohepta[1,2-b]pyridin-11-one to 0° C., slowly add 75 mL (93.69 mmol) of sulfur monochloride over 20 minutes, then slowly add 25 mL (48.59 mmol) of Br₂ over 15 minutes. Heat at 95° C. for 20 hour, add 12.5 mL (24.3 mmol) of Br₂ and heat for a another 24 hours. Cool the mixture, and slowly add to a mixture of CH₂Cl₂ and 1N NaOH (aqueous) at 0° C. Wash the organic phase with water, dry over MgSO₄ and concentrate in vacuo to a residue. Chromatograph the residue (silica gel, 500 mL CH₂Cl₂ then 0.2%–5% (10% NH₄OH in MeOH)/CH₂Cl₂), then chromatograph again (silica gel, 3%–8.5% EtOAc/hexane) to give 8.66 g of the product compound. MS: MH⁺=322

PREPARATIVE EXAMPLE 16

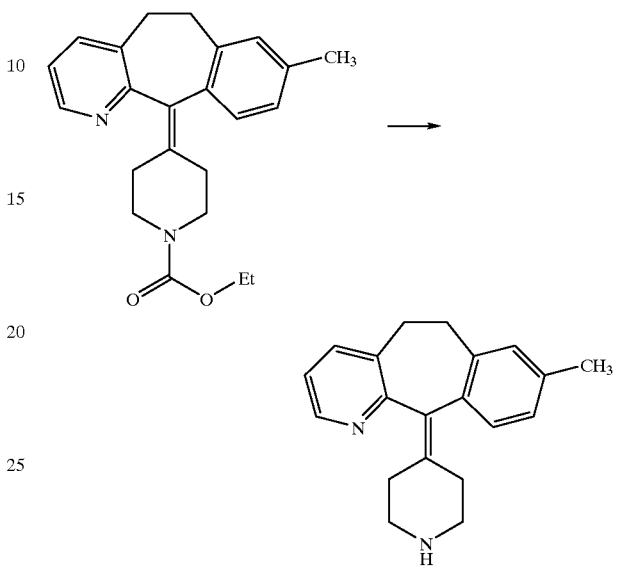

Dissolve 0.16 g (0.46 mmol) of 4-(8-methyl-5,6-dihydro-11H-benzo[5,6]cyclohepta[1,2-b]pyridin-11-ylidine)-1-ethoxycarbonylpiperidine, in 2 mL EtOH and add 4 mL of 12 N HCl. Heat the solution for 3 hours at 85° C., then cool to 25° C. Adjust to pH=10 with 50% NaOH (aqueous) and extract several times with 50 mL of EtOAc. Combine the organic layers, dry them over MgSO₄, and concentrate in vacuo to give the product compound.

PREPARATIVE EXAMPLE 17

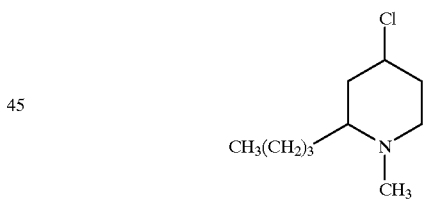

STEP A:

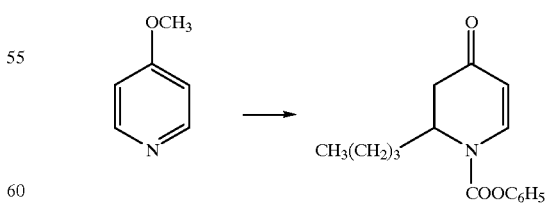

4-Methoxypyridine is reacted with n-butyl Grignard and phenylchloroformate via substantially the same procedure as described in Comins, et al., Tet. Lett., 27, (38) 4549–4552 (1986), to form the desired unsaturated ketopiperidine product.

STEP B:

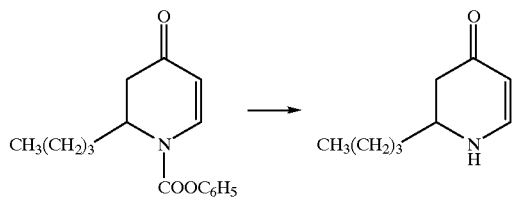

The product of Step A is hydrolyzed via substantially the same procedure as described in Preparative Example 34C, of WO 95/10516, to give the amine product.

STEP C:

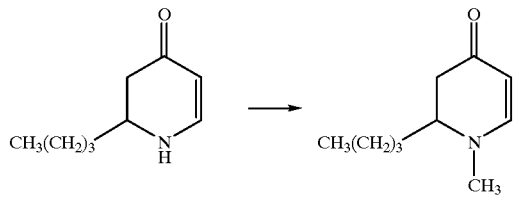

The product of step B is methylated by reacting with methyl iodide and NaH at room temperature to form the N-methyl product.

STEP D:

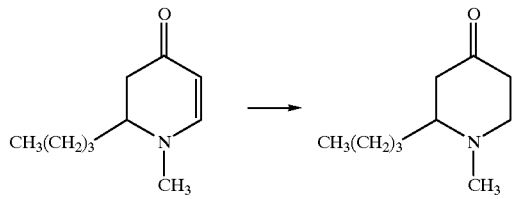

The product of Step C is hydrogenated using 10% Pd/C to form the product compound.

STEP E:

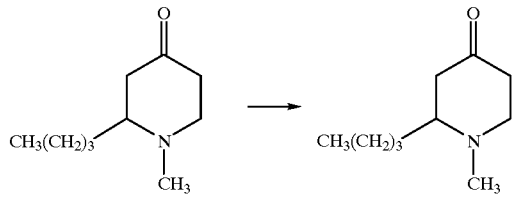

The product of Step D is reacted with NaBH$_4$ in EtOH at room temperature to form the alcohol product.

STEP F:

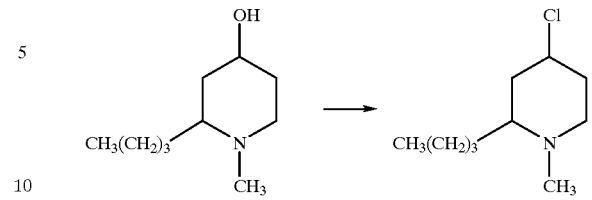

The product of Step E is treated with an excess SOCl$_2$ in pyridine to give the 4-chloropiperidine.

Following substantially the same procedure as described in Preparative Example 17, Steps A–F, and using the appropriate Grignard reagent in place of n-butyl Grignard, the following compounds can also be prepared:

| Preparative Example No. | $R^{26}$ |
|---|---|
| 18 | $C_6H_5CH_2$— |
| 19 | $CH_3OCH_2CH_2$— |
| 20 | $CH_3O(CH_2)_3$— |
| 21 | n-$C_3H_7OCH_2CH_2$— |
| 22 | $CH_3SCH_2CH_2$— |
| 23 | ▷—OCH$_2$CH$_2$— |
| 24 | (3-pyridyl)CH$_2$OCH$_2$CH$_2$— |
| 25 | $C_6H_5SO_2CH_2CH_2$— |
| 26 | ▷—CH$_2$SO$_2$CH$_2$CH$_2$— |
| 27 | $CH_3CONH(CH_2)_4$— |

EXAMPLE 1

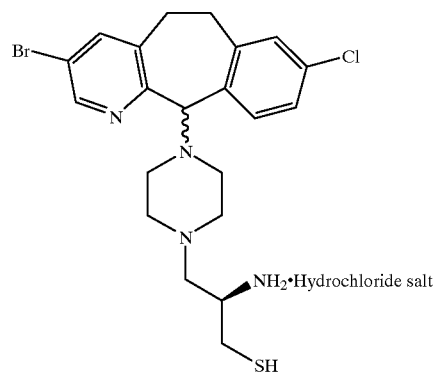

STEP A:

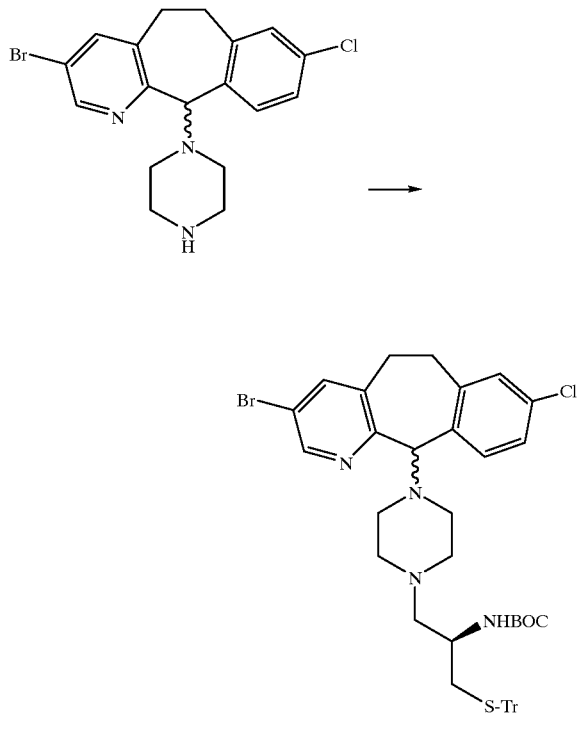

STEP B:

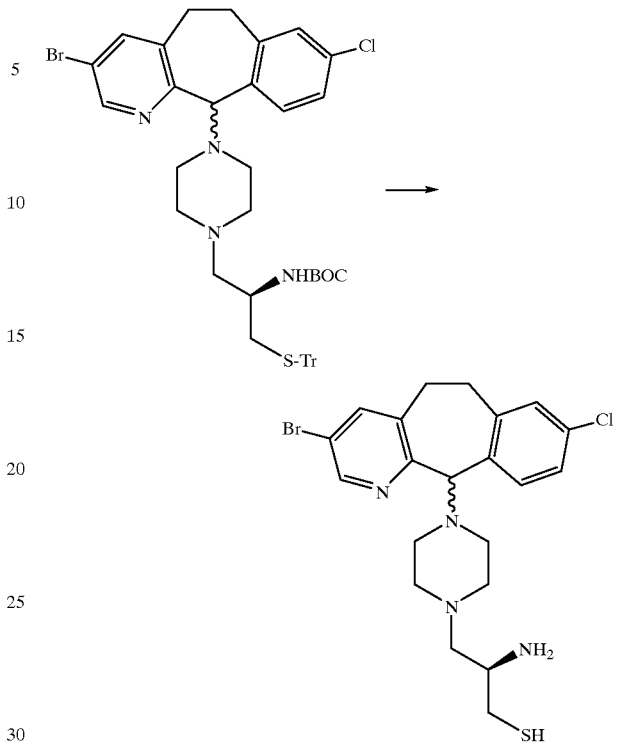

The title compound from Preparative Example 40, of WO 95/10516, (1 equivalent) (1.0 g.) in dry methylene chloride (11.85 ml.) was treated with trifluoroacetic acid (30.5 equivalents) (5.92 ml.) and the solution was stirred at 25° C. for 0.5 h. The mixture was evaporated to dryness and then reevaporated to dryness to give the trifluoroacetic acid salt. The latter was dissolverd in dry DMF (15ml.) and triethylamine was added dropwise until the pH reached 6.2. Sodium triacetoxyborohydride (1.81 equivalents) (0.98 g.) and crushed, activated 4 Angstrom molecular sieves (1.48 g.) were added and the mixture was stirred under argon at 0° C. A solution of 2(R)-N-tert-butoxycarbonylamino-3-triphenylmethyl-propanal (0.91 equivalents) (1.037 g.) in dry DMF (8 ml.) was added dropwise over 40 min. The mixture was allowed to warm to room temperature over a period of 2 h. The mixture was filtered and evaporated to dryness and the residue was taken up in ethyl acetate and washed with saturated aqueous sodium bicarbonate. The organic layer was dried over magnesium sulfate, filtered and evaporated to dryness. The residue was chromatographed on a silica gel column using 0.5–4%(10% concentrated ammonium hydroxide in methanol)-methylene chloride as the eluant to give a diastereomeric mixture of isomer A and isomer B. Yield: 0.9073 g., MH$^+$825.2.

The N-formyl derivative of the starting reactant was also isolated (Yield: 0.4945 g). Use of dichloroethane as the solvent in the above reaction instead of DMF avoids the formation of the N-formyl derivative.

The mixture of diastereoisomers A and B (0.683 g.) was separated on a silica gel column using 5% acetone in methylene chloride as the eluant to give pure samples of isomer A (89.2 mg.) and isomerB (66.4 mg.) together with an overlapping mixture of both isomers (384.1 mg.).

By essentially the same procedure as described in Example 21 Step B, the title compound (Isomers A and B) from Step A above (1 equivalent) (1.024 g.) was reacted with triethylsilane (0.089 ml.) and trifluoroacetic acid (1.043 ml.) in methylene chloride (10.24 ml.) to give the title compound as the hydrochloride salt. Yield: 0.5303 g.; MH$^+$ 483.0. PMR data (D$_2$O): aromatic proton signals at: 7.28, 7.37 (2H), 8.23, 8.68.

EXAMPLE 2

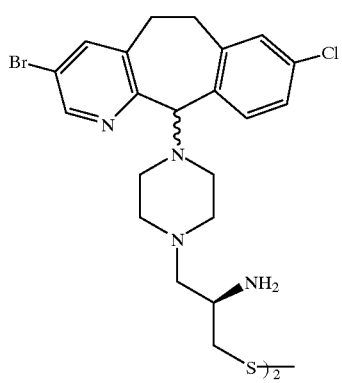

The title compound from Example 1B (as the free base) is dissolved in MeOH containing iodine and stirred at 25° C. for 30 mins. the solution is evaporated to dryness and the CH$_2$Cl$_2$ is taken up in CH$_2$Cl$_2$ and washed in saturated aqueous NaHCO$_3$ and then brine. The CH$_2$Cl$_2$ layer is dried over MgSO$_4$ filtered and evaporated to dryness to give the title compound. The title compound is purified on a silica gel column using 3% (10% concentrated NH$_4$OH in MeOH)—CH$_2$Cl$_2$ to give the title compound.

EXAMPLE 3

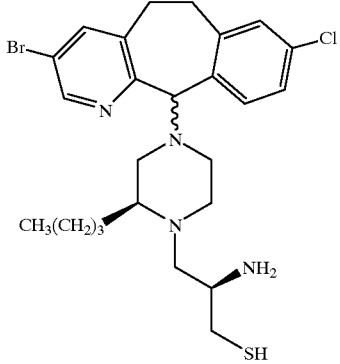

STEP A:

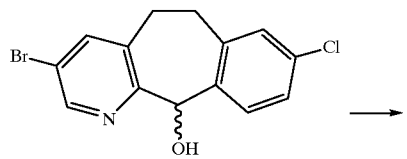

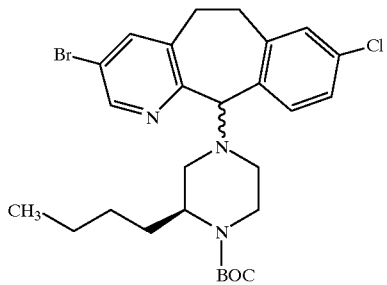

The 11-hydroxy intermediate (1 equivalent) (1 g.) prepared in Preparative Example 40, of WO 95/10516 was reacted as described in Preparative Example 7B, of WO 95/10516, to give the 11-chloro intermediate. The latter was reacted with 1-tert-butoxycarbonyl-2(S)-n-butylpiperazine (1.1 equivalents) (1.1314 g.), prepared as described in Example 3C of PCT International Publication WO95/00497, by essentially the same procedure as described in Preparative Example 7C, of WO 95/10516, to give the title compound. Yield: 1.7862 g.; MH$^+$ 550.

STEP B:

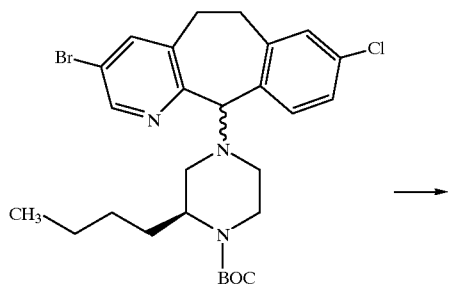

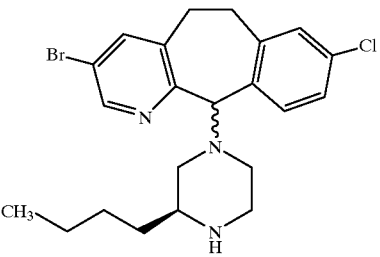

The title compound from Step A above (1.6406 g.) in methanol (1 6.4 ml.) was treated with 10% (v/v) concentrated sulfuric acid in dioxane (41 ml.) and the mixture was stirred at 25° C. for 4 h. The solution was neutralized with BioRad AG1X8 (OH$^-$) resin and filtered. The resin was washed with methanol and methylene chloride and the combined filtrates were evaporated to dryness. The residue was chromatographed on a silica gel column using 1% (10% concentrated ammonium hydroxide in methanol)-methylene chloride as the eluant to give the title compound. Yield: 1.2451 g., MH$^+$ 450.

STEP C:

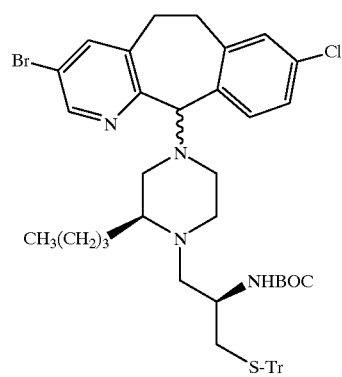

The title compound from step B is reacted as described in Example 1A above to give the title compound. The latter is purified on a silica gel column using 0.5%–1% (10% concentrated NH$_4$OH in MeOH) —CH$_2$Cl$_2$ to give the title compound.

STEP D:

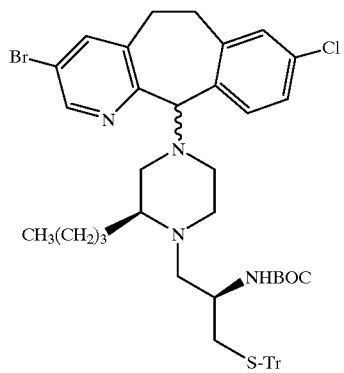

The title compound from Step C above is reacted as described in Example 1B above to give the title compound as its HCl salt.

EXAMPLES 4–8

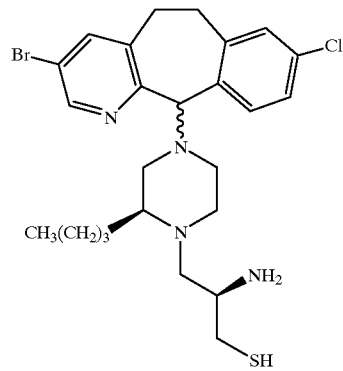

The title compound from Example 13A of WO 95/00497 is reacted with benzyloxycarbonyl chloride under standard conditions known to one skilled in the art, to give the N-Cbz protected alcohol shown above. After purification in the usual way the latter may be reacted with a variety of reagents shown in Column 1 of Table 1 to give the corresponding N-Cbz protected intermediates where R is as defined in Column 2 of Table 1. After purification in the usual way the latter may be deprotected using mild catalytic hydrogenation procedures known in the art, to give after suitable purification, the final desired intermediates shown in Column 2 of Table 1.

TABLE 1

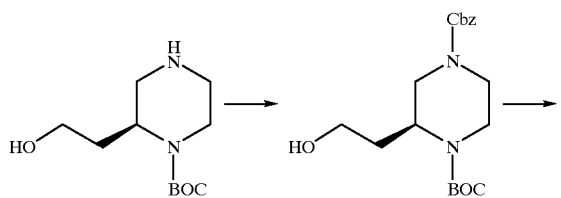

| Column 1 | Column 2 |
|---|---|
| (pyridyl-CH₂Cl) and NaH | R= (pyridyl-CH₂O—) Prepared as described in Example 14A of WO 95/00497. Example 4. |
| $C_6H_5SSC_6H_5$ + (n-Bu)$_3$P | R = (PhSO₂—) Prepared as described in Example 20B and 20C of WO 95/00497. Example 5. |
| (i) CH₂=CHOCH₃ + Hg(OAc)₂ + CH₃COOH (ii) CH₂I₂ + Et₂Zn | R = (cyclopropyl-O—) Prepared as described in Examples 26A and 26B of WO95/00497. Example 6 |
| (i) EtOCON=NCOOEt + (C₆H₅)₃P + CH₃COSH (ii) NH₃ + CH₃OH + (cyclopropyl-CH₂Br) (iii) Mg monoperphthalic acid + CH₃OH | R= (cyclopropyl-CH₂SO₂—) Prepared as described in Examples 29A, 29B and 29C of WO95/00497. Example 7 |
| n-C₃H₇I + NaH | R = n-C₃H₇O— Prepared as described in Example 13C of WO 95/00497. Example 8 |

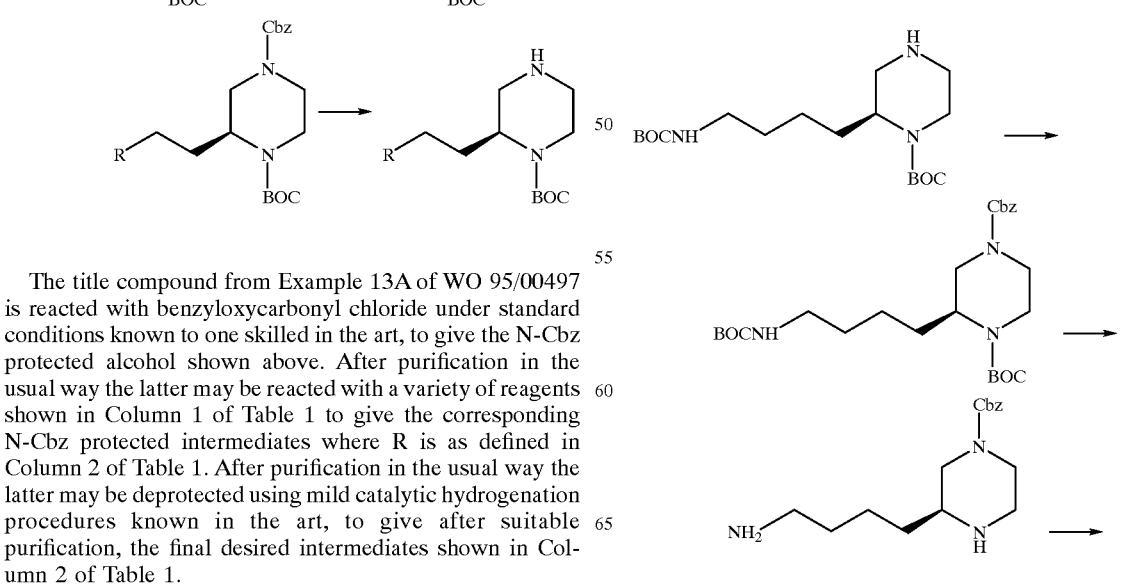

-continued

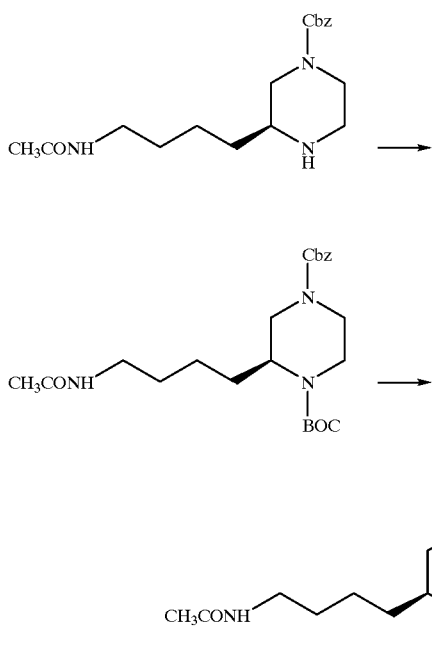

The title compound from Example 27D of WO 95/00497 is converted by the scheme shown above, using standard procedures known to one skilled in the art, into 1-BOC-2(S)-(4-acetylaminobutyl)piperazine. piperazine.

EXAMPLES 10–19

By essentially the same procedures as set forth in Example 3 above but using the compounds set forth in Column 1, Table 2 (below), in place of 1-BOC-2(S)-n-butylpiperazine, one can obtain compounds of the formula:

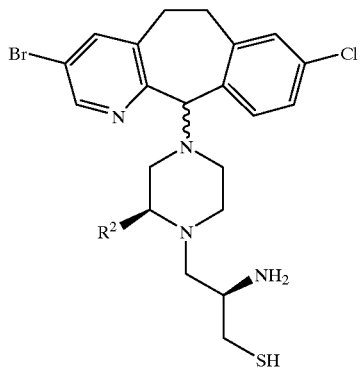

wherein $R^2$ is as listed in Column 2, Table 2

TABLE 2

| Column 1 | Column 2 |
|---|---|
| ![structure] C₆H₅CH₂—piperazine—BOC<br>Prepared as described in Example 6C of WO 95/00497. | $R^2 = C_6H_5CH_2-$<br>Example 10 |
| ![structure] CH₃OCH₂CH₂—piperazine—BOC<br>Prepared as described in Example 7D of WO 95/00497. | $R^2 = CH_3OCH_2CH_2-$<br>Example 11 |
| ![structure] CH₃SCH₂CH₂—piperazine—BOC<br>Prepared as described in Example 8C of WO 95/00497. | $R^2 = CH_3SCH_2CH_2-$<br>Example 12 |

TABLE 2-continued

| Column 1 | Column 2 |
|---|---|
| 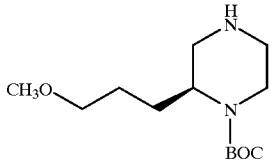<br>Prepared as describe in Example 18D of WO 95/00497 | $R^2 = CH_3O(CH_2)_3—$<br>Example 13 |
| 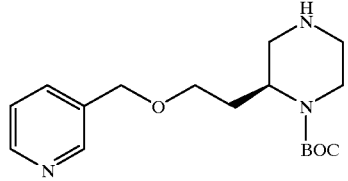<br>Prepared as described in Example 4 above | $R^2 =$ <br>Example 14 |
| 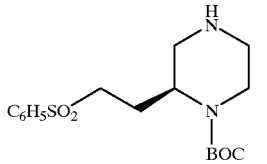<br>Prepared as described in Example 5 above | $R^2 =$ $C_6H_5SO_2$⌒⌒<br>Example 15 |
| 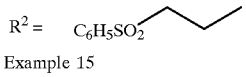<br>Prepared as described in Example 6 above | $R^2=$ 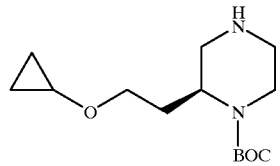<br>Example 16 |
| 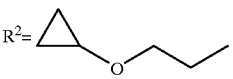<br>Prepared as described in Example 7 above | $R^2=$ 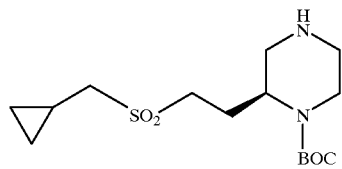<br>Example 17 |
| 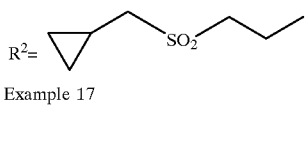<br>Prepared as described in Example 8 above | $R^2 = n\text{-}C_3H_7O(CH_2)_2—$<br>Example 18 |

TABLE 2-continued

| Column 1 | Column 2 |
|---|---|
| 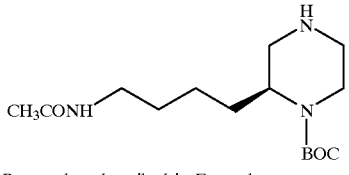 | R² = CH₃CONH(CH₂)₄— Example 19 |

Prepared as described in Example 9 above

EXAMPLE 20

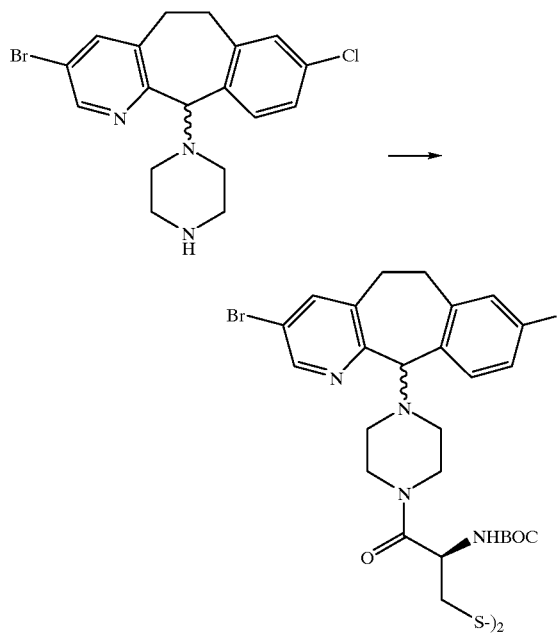

STEP A:

The title compound from Preparative Example 40, of WO 95/10516, (1 equivalent) (1 g), N,N'-bis-BOC-L-cystine (0.45 equivalents) (0.501 g), DEC (0.9 equivalent) (0.4366 g), HOBT (0.9 equivalent) (0.3078 9) and N-methylmorpholine (0.9 equivalent) (0.2304 g) were dissolved in anhydrous DMF (25 mL) and the mixture was stirred at 25° C. under argon for 68 hours. The mixture was evaporated to dryness and taken up in $CH_2Cl_2$ and washed with saturated aqueous $NaHCO_3$ and then water. The $CH_2Cl_2$ layer was dried over $MgSO_4$ filtered, and evaporated to dryness. The residue was chromatographed on a silica gel column (60×2.5 cm) using 0.5%–1% (10% concentrated $NH_4OH$ in MeOH) —$CH_2Cl_2$ to give the title compound. Yield: 1.09 g. $MH^+$ 1189.7.

STEP B:

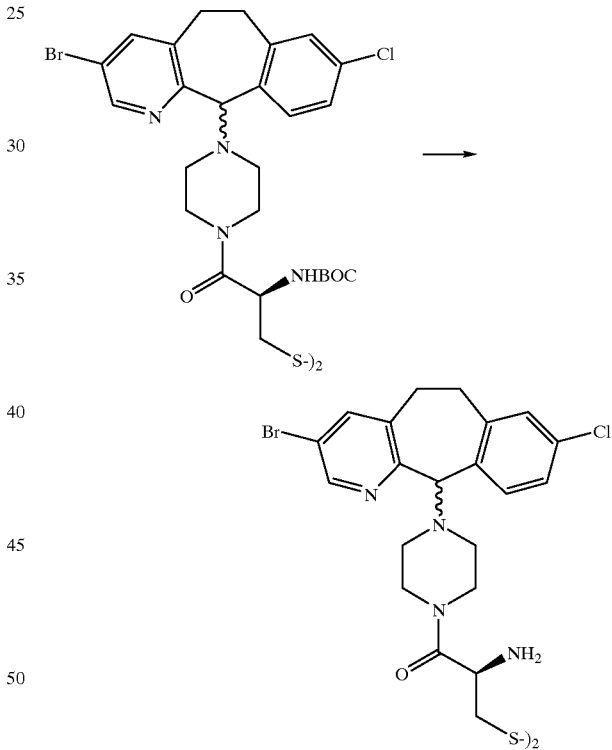

The title compound from Step A above (1 equivalent) (0.944 g) was added to MeOH (10 mL). A 10% (v/v) concentrated $H_2SO_4$ in dioxane solution (20 mL) was added and the solution was stirred at 25° C. under argon for 2 hours. The mixture was neutralized with BioRad AG 1X8 (OH⁻) resin. The resin was filtered off and washed with MeOH and $CH_2Cl_2$. The combined filtrates were evaporated to dryness and the residue was chromatographed on a silica gel column (110×2.5 cm) using: 5% (10% concentrated $NH_4OH$ in MeOH)—$CH_2Cl_2$ to give the title compound. Yield: 0.6879 g, $MH^+$ 989.

CMR data ($\delta_c$ ($CDCl_3$)) for the product of Step B was: (1) tricyclic: (a) $CH_2$: 31.3, 31.4, (b) CH: 147.9, 142.1, 133.3, 127.1, 131.4, 79.71 and (c) C: 120.9, 141.7, 135.0, 136.1, 137.6, 156.3; (2) piperazine: (a) $CH_2$: 46.2, 52.6, 52.0, 43.0; and (3) Piperazine N-substituent: (a) $CH_2$: 45.0, (b) CH: 51.0, and 0: 172.2.

STEP C:

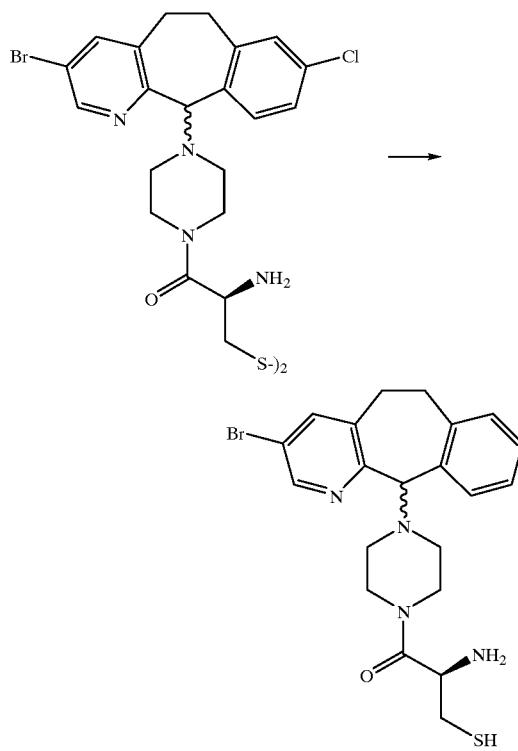

The title compound from Step B above is dissolved in a mixture of anhydrous MeOH and THF and $NaBH_4$ is added the mixture is stirred under argon at 25° C. for 2 hours. The solution is evaporated to dryness and the residue is taken up in $CH_2Cl_2$ and washed with water. The $CH_2Cl_2$ layer is dried over $MgSO_4$, filtered and evaporated to dryness to give a residue which is purified by substantially the same procedure as described for Example 1E of WO95/00497 to give the title compound as its HCl salt.

Alternatively, zinc dust and 1.0N HCl may be used in place of $NaBH_4$ to effect the above reduction.

EXAMPLE 21

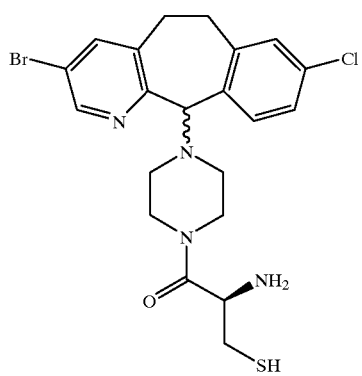

STEP A:

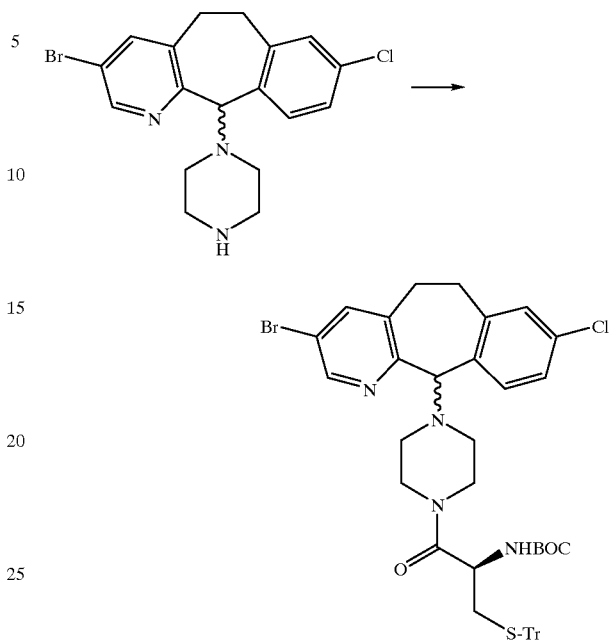

The title compound from Preparative Example 40, of WO 95/10516, (1 equivalent) (1 g), N-BOC-S-trityl-L-cysteine (1.34 equivalents) (1.584 g) DEC (1.34 equivalents) (1.5 g), HOBT (1.34 equivalents) (0.4618 g), and N-methylmorpholine (1.34 equivalents) (0.1048 g) (0.114 mL) were dissolved in anhydrous DMF (25 mL) and the mixture was stirred under argon at 25° C. for 68 hours. The solution was evaporated to dryness and the residue was taken up in $CH_2Cl_2$ and washed with saturated aqueous $NaHCO_3$ and then water. The $CH_2Cl_2$ layer was dried over $MgSO_4$, filtered and evaporated to dryness and the residue was chromatographed on a silica gel column (60×2.5 cm) using 0.5% (10% concentrated $NH_4OH$ in MeOH)—$CH_2Cl_2$ to give the title compound. Yield: 2.04 g, $MH^+$ 837.6.

STEP B:

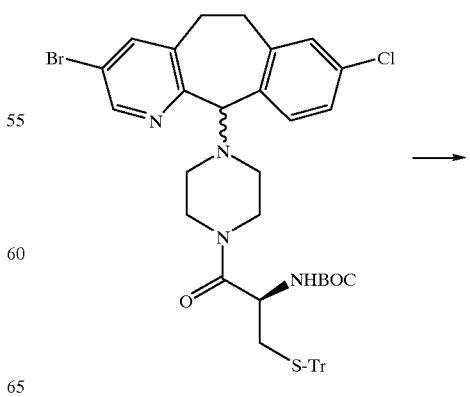

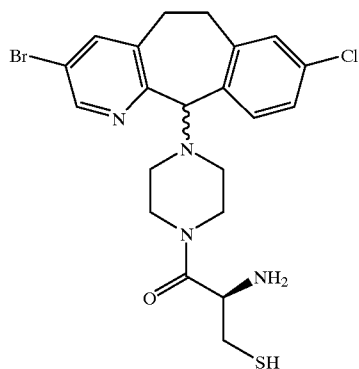

The title compound from Step A above (1 equivalent) (0.5 g.) was dissolved in dry methylene chloride (5 ml.) and triethylsilane (4.07 equivalents) (282.1 mg.) (0.388 ml.) was added under an argon atmosphere. Trifluoroacetic acid (2.5 ml.) was added and the solution was stirred at 25° C. for 1 h. The solution was evaporated to dryness and the residue was partitioned between water and hexane. The aqueous layer was separated and passed over BioRad AG3X4(Cl⁻) resin (100 ml.) and the resin was washed with water. The combined eluates and wash were lyophilized to give the title compound as the hydrochloride salt. Yield: 306.9 mg., MH⁺ 497.2. The method described above is essentially the same as described for Example 1E of WO95/00497. H¹ NMR (D₂O): Aromatic proton signals at: 7.00 (2H), 7.17, 7.50, 8.21.

STEP C:

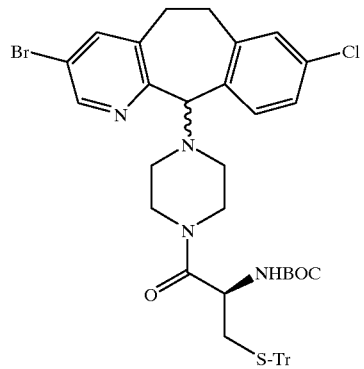

The title compound from Step A above (1 equivalent) (30 mg) was dissolved in dry CH₂Cl₂ (1 mL) and triethylsilane (4 equivalents) (16.93 mg) (0.0233 mL) was added followed by TFA (1 ml). The mixture was stirred at 25° C. under argon for 1 hour and then neutralized with BioRad AG1X8 (OH⁻) resin. The resin was filtered off and washed with MeOH and CH₂Cl₂. The combined filtrates were evaporated to dryness to give the title compound.

STEP D:

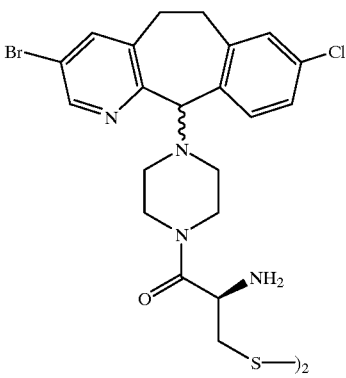 

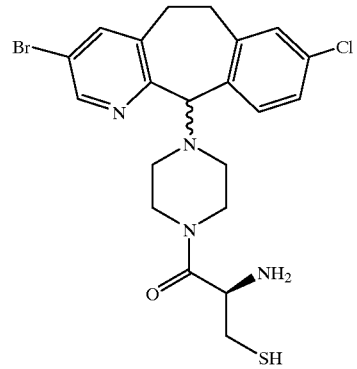

The title compound from Step B above is reduced as described in Example 20 Step C above to give the title compound.

STEP E

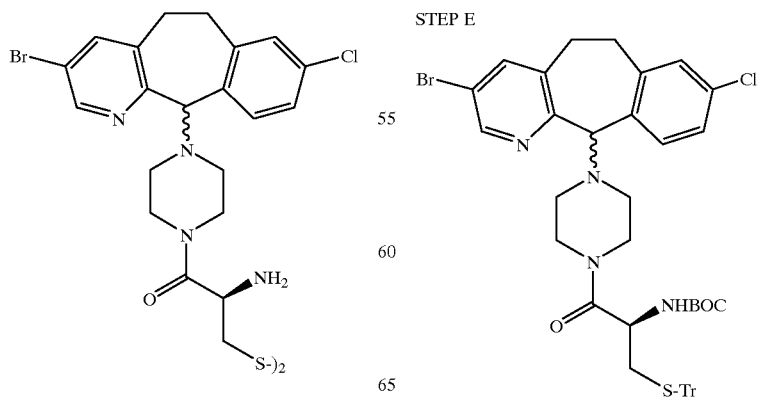 

-continued

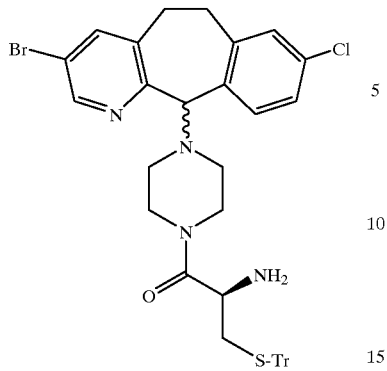

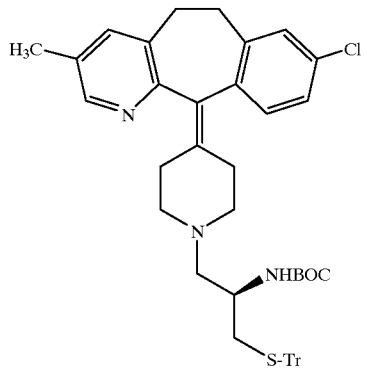

The title compound from step A above (1 equivalent) (1.2 g.) was added to methanol (10 ml.) and a solution of 10% concentrated sulfuric acid in dioxane (v/v) (30 ml.) was added. The mixture was stirred at 25° C. under argon for 2 h. The mixture was diluted with methylene chloride and methanol and neutralized with BioRad AG1X8 (OH⁻) resin. The resin was filtered off and washed with methanol followed by methylene chloride. The combined filtrates were evaporated to dryness to give a solid residue that was chromatographed on a silica gel column using 2% (10% concentrated ammonium hydroxide in methanol)-methylene chloride as the eluant to give the title compound. Yield: 1.0 g., MH⁺ 739.2.

The title compound from Preparative Example 3E, of WO 95/10516, is reacted under the same conditions described in Example 1A above to give the title compound, which is purified in the usual way.

STEP B

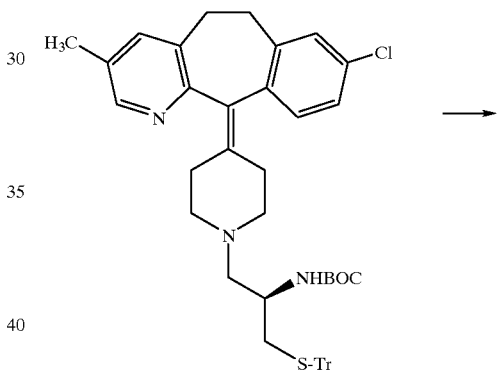

EXAMPLE 22

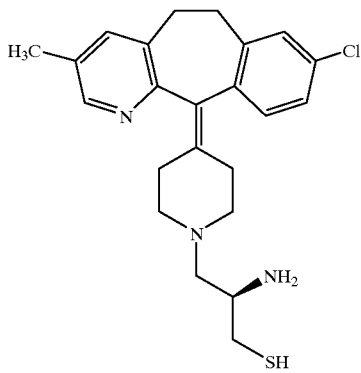

STEP A

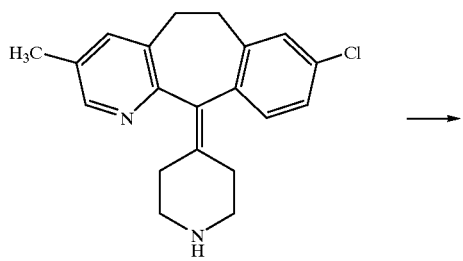

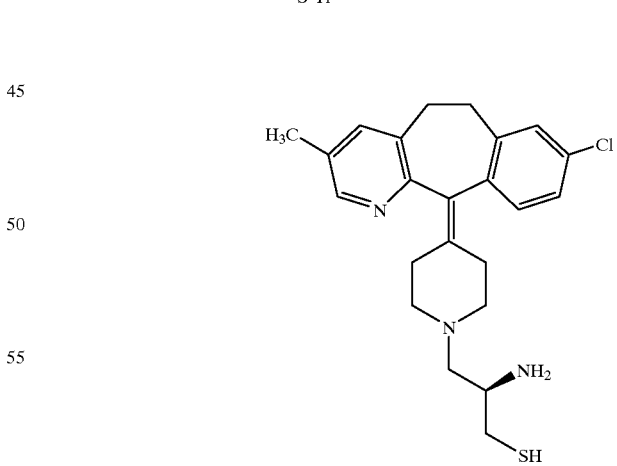

The title compound from Step A above is deprotected under similar conditions to those described in Example 1B above to give the title compound.

EXAMPLE 24

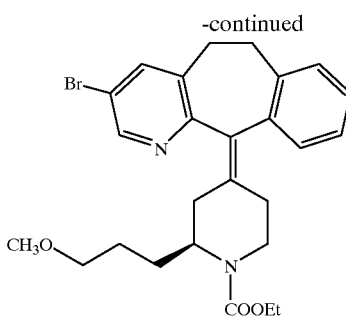

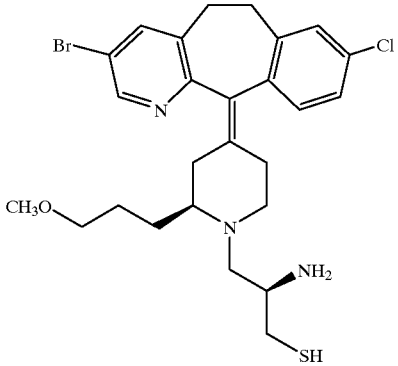

STEP A

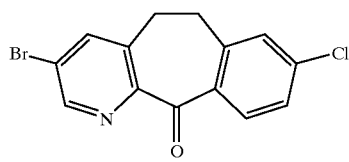

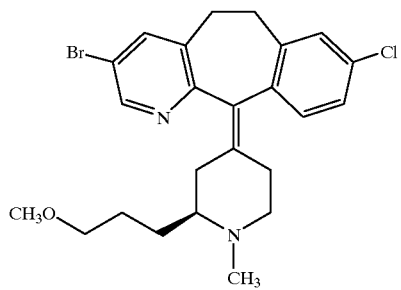

The title compound from Preparative Example 20A, of WO 95/10516, is reacted with a substituted Grignard reagent from Example 23 above under essentially the same conditions as described in Preparative Examples 2D and 2E, of WO 95/10516, to give the title compound.

STEP B:

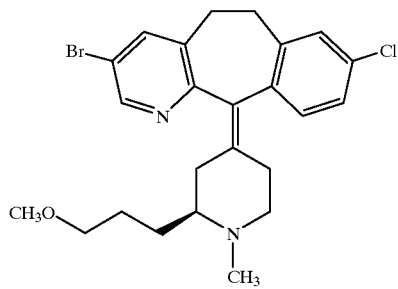

The title compound from Step A above is reacted under essentially the same conditions as described in Preparative Examples 1F and 1G, of WO 95/10516, to give the title compound.

STEP C:

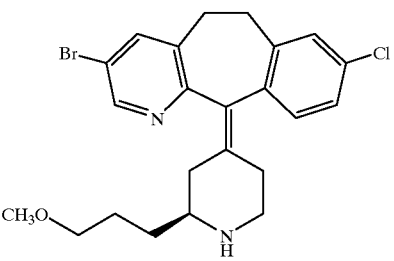

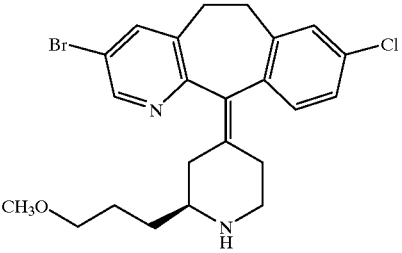

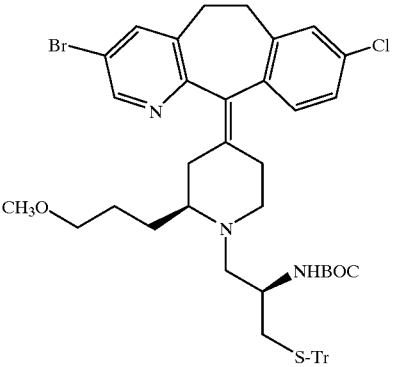

The title compound from Step B above is reacted as described in Example 1A above to afford the title compound.

STEP D:

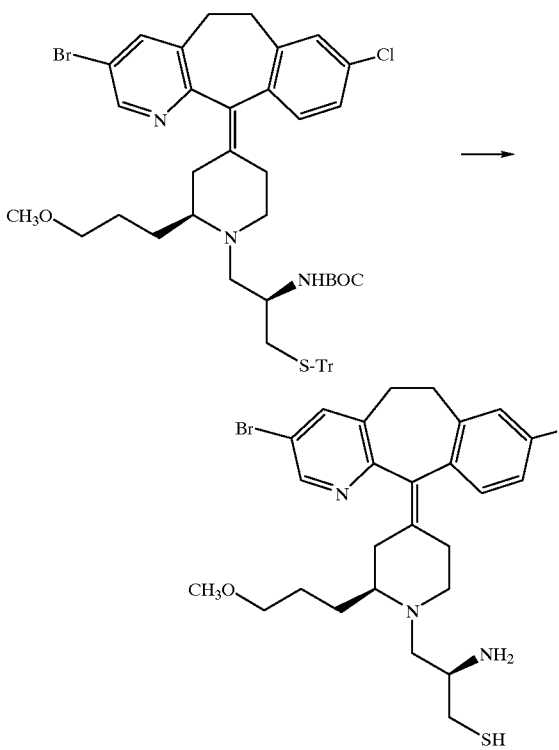

The title compound from Step C above is reacted as described in Example 1B above to give the title compound.

EXAMPLE 25

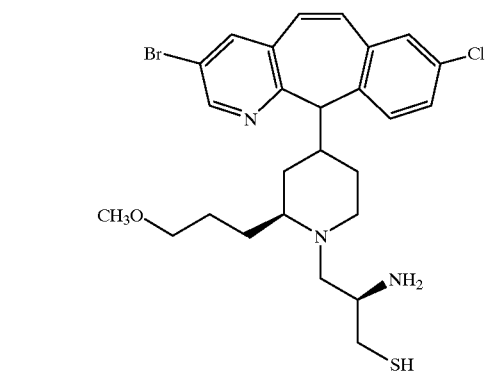

STEP A:

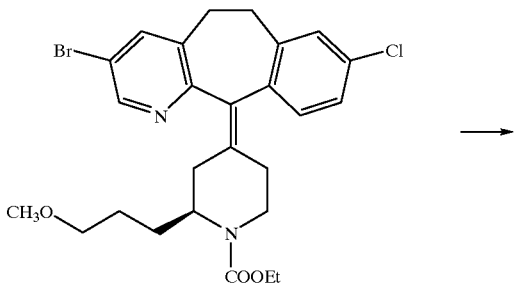

-continued

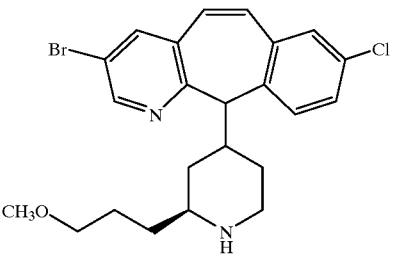

The title compound from Example 24B above is reacted with $CF_3SO_3H$ as described in Preparative Example 34A, of WO 95/10516, to afford the title compound.

STEP B:

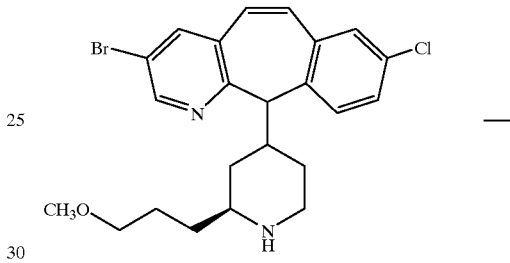

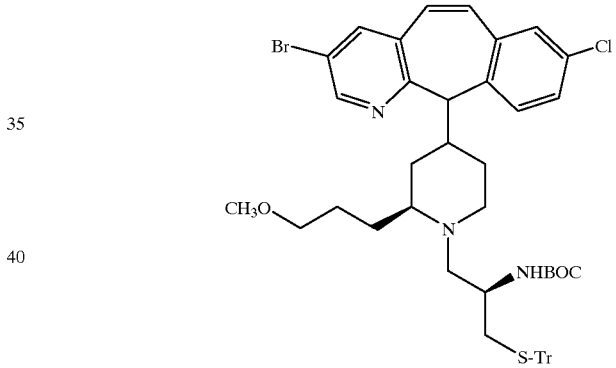

The title compound from Step A above is reacted as described in Example 1A above to give the title compound.

STEP C:

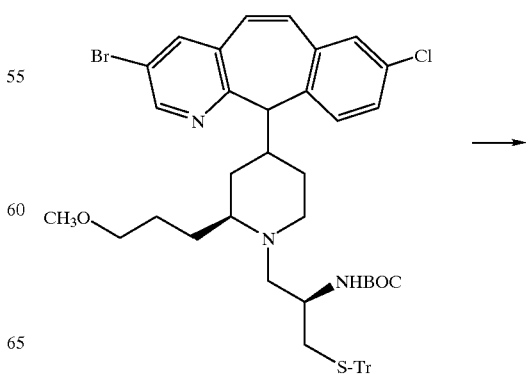

-continued

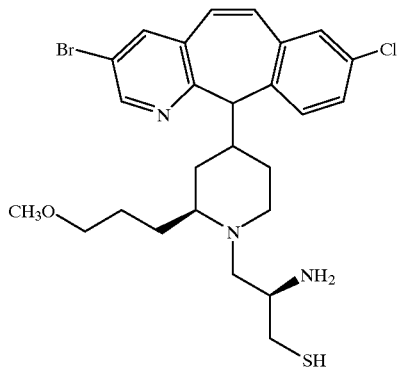

The title compound from Step B above is reacted as described in Example 1B above to give the title compound.

EXAMPLE 26

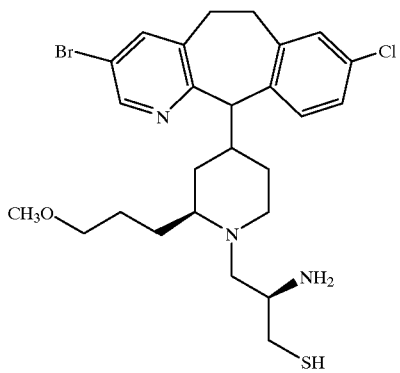

STEP A

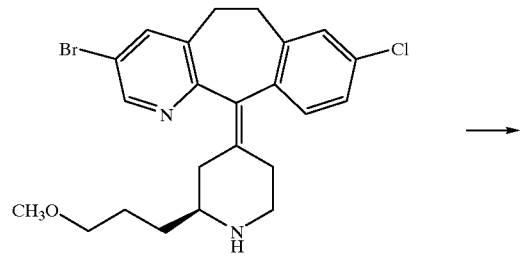

The title compound from Example 24B above is reacted with either LiAlH$_4$ in refluxing toluene, or preferably with DIBAL-H in refluxing toluene to give the title compound.

STEP B:

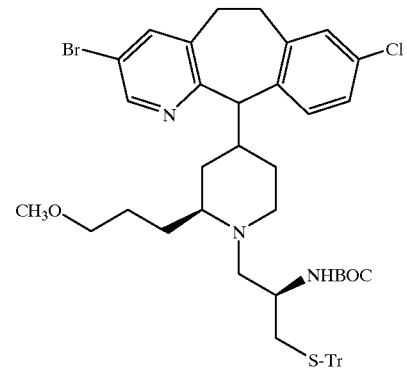

The title compound from Step A above is reacted as described in Example 1A above to give the title compound.

STEP C:

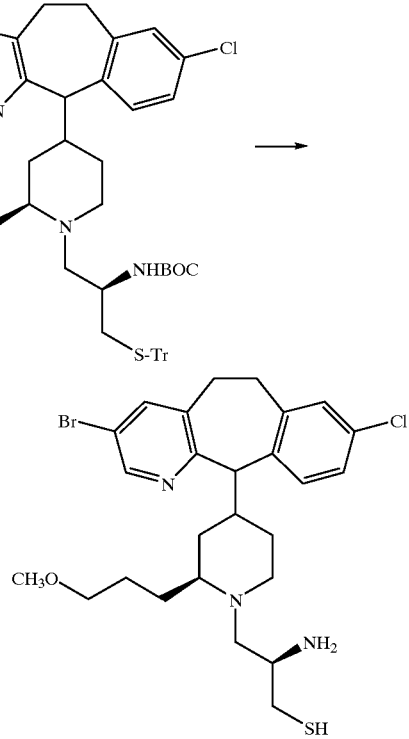

The title compound from Step B above is reacted as described in Example 1B above to afford the title compound.

EXAMPLE 27

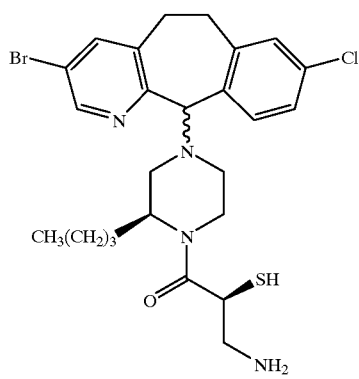

STEP A

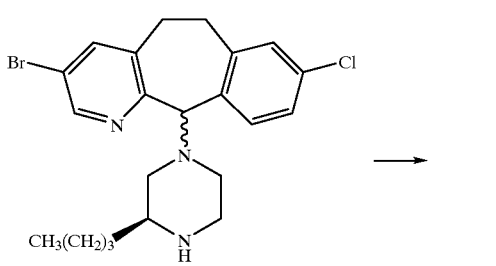

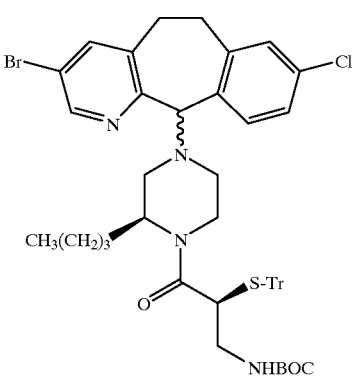

The title compound from Example 3B above is reacted with 2-S-trityl-3-N-BOC-iso-cysteine under essentially the same conditions as described in Example 21A above to give the title compound. The protected iso-cysteine is prepared by methods known to one skilled in the art from iso-cysteine (Gustavson, et al., *Syn. Comm.*, 21, (2) 265–270 (1991)).

STEP B

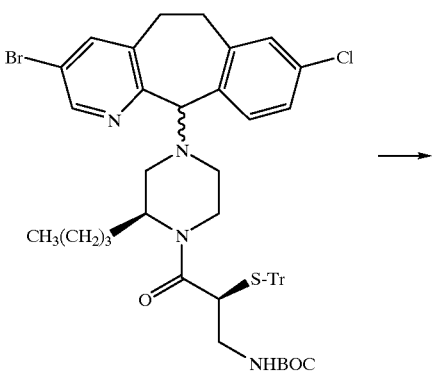

-continued

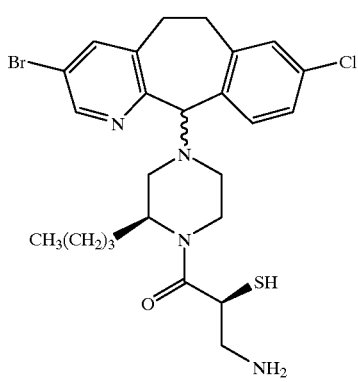

The title compound from Step A above is reacted as described in Example 1B above to give the title compound.

EXAMPLE 28

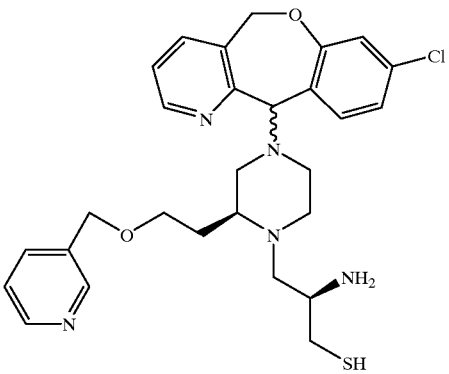

STEP A:

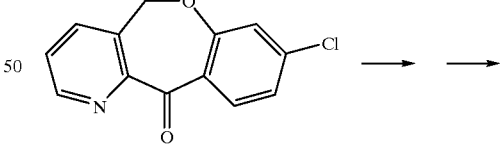

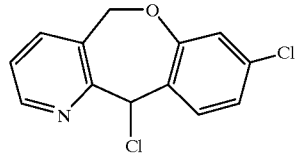

The title compound from Preparative Example 4 of WO89/10369 is converted into the title compound by methods similar to those described in WO89/10369.

STEP B:

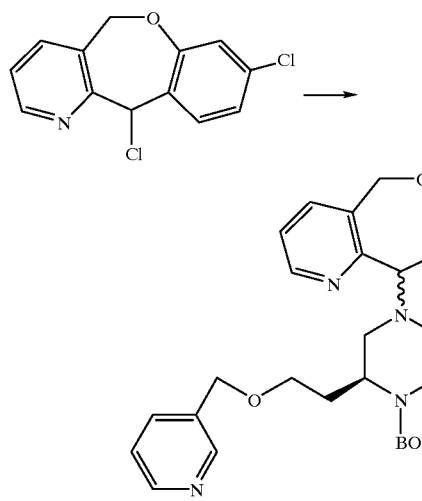

The title compound from Step A above is reacted with the substituted piperidine from Example 4 above under similar conditions to those described in WO89/10369 to give the title compound.

STEP C:

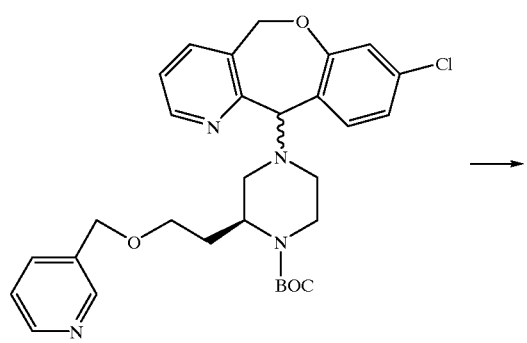

The title compound from Step B above is reacted as described in Example 3B above to give the title compound.

STEP D:

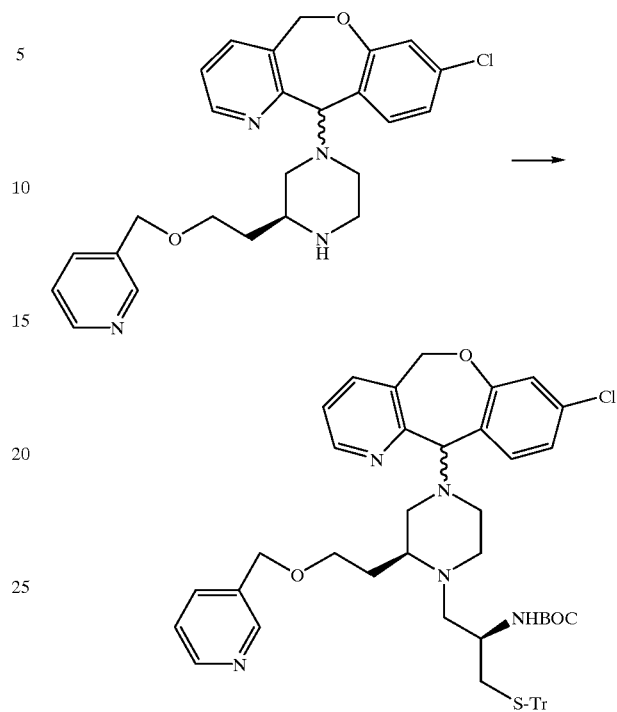

The title compound from Step C above is reacted as described in Example 1A above to give the title compound.

STEP E:

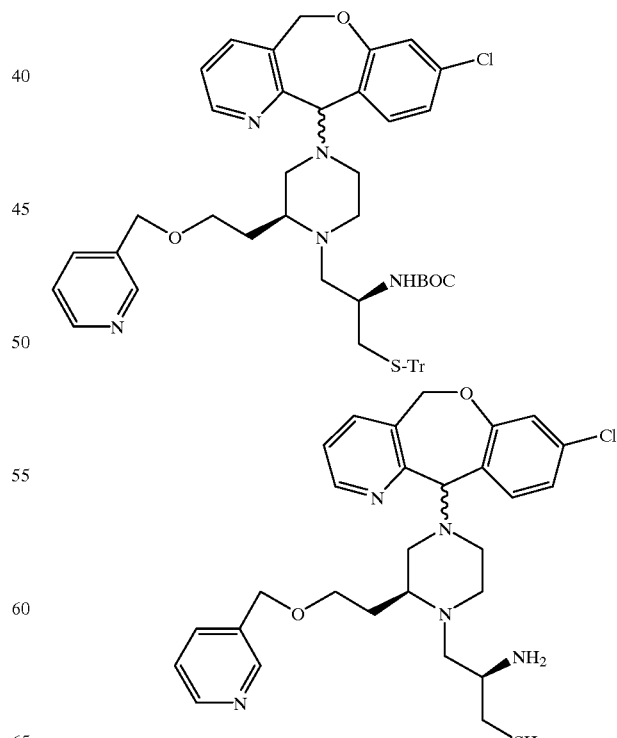

The title compound from Step D above is reacted as described in Example 1B above to give the title compound.

EXAMPLE 29

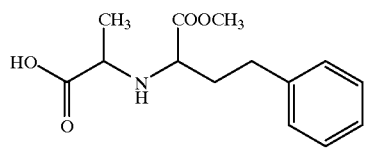

(prepared as described in U.S. Pat. No. 4,470,972 and E. M. Smith, et al., *J. Med. Chem.*, 32, 1600 (1989)), under similar conditions to those described in Example 20A to give the title compound.

STEP B:

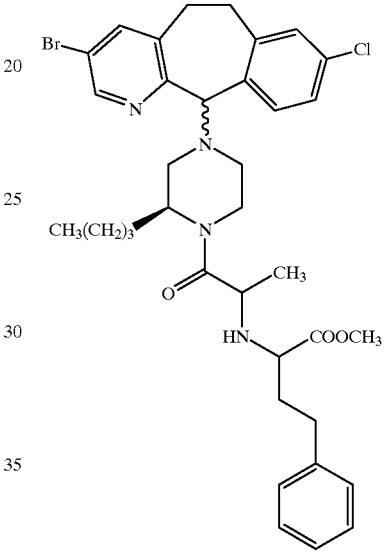

STEP A:

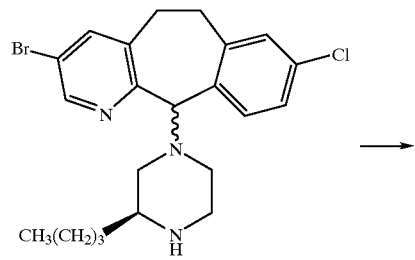

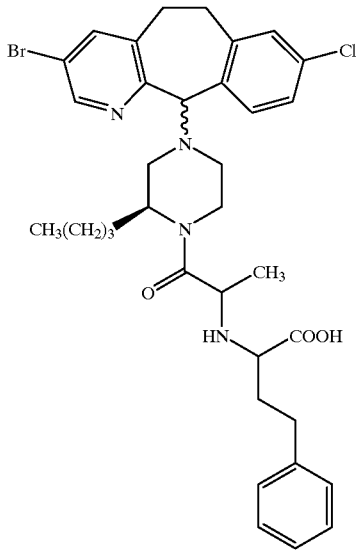

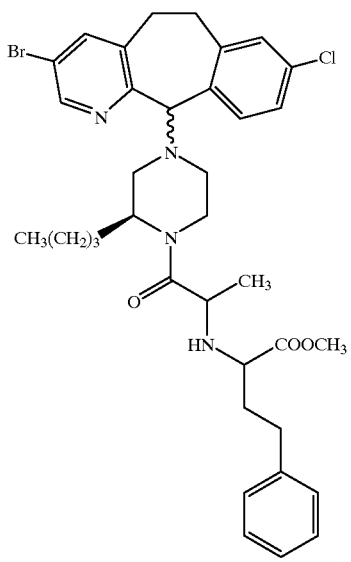

The title compound from Example 3B above is reacted with the acid,

The title compound from Step A above is reacted with base to afford the title compound.

EXAMPLE 30

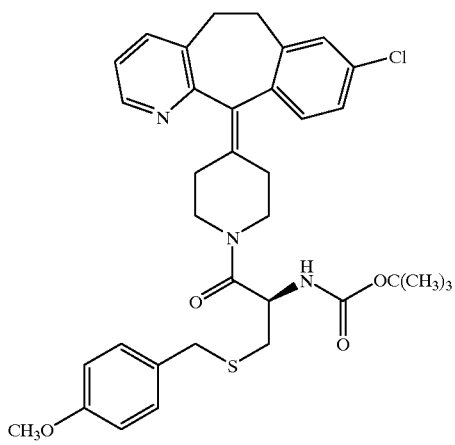

Combine 0.5 g of the product of Preparative Example 1, Step G, of WO 95/10516, 0.54 g of N-BOC-S-(p-methoxybenzyl)-L-cysteine, 0.321 g of DEC, 0.226 g of HOBT, 0.176 g of N-methylmorpholine and 15 mL of DMF at 0° C., then stir the mixture for 3 days at room temperature. Concentrate in vacuo to a residue which is dissolved in $CH_2Cl_2$ and washed successively with saturated $NaHCO_3$ (aqueous) and brine. Dry the organic solution over $Na_2SO_4$ and concentrate in vacuo to a residue. Chromatographed (silica gel, 98% $CH_2Cl_2$/MeOH+$NH_4OH$) to give the product compound. MS: $MH^+$=634.

EXAMPLE 31

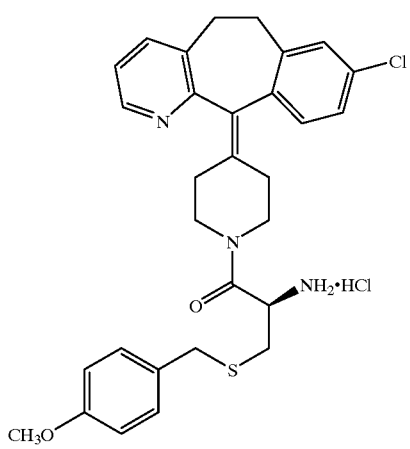

Combine 0.1 g of the product of Example 30, 4 mL of THF and 2 mL of 4N HCl in dioxane and stir the mixture for overnight at room temperature. Concentrate in vacuo to give 0.06 g of the product compound. MS: $MH^+$=534.

EXAMPLE 32

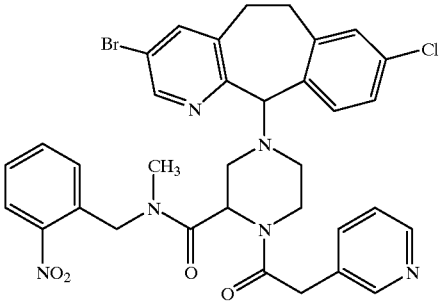

STEP A:

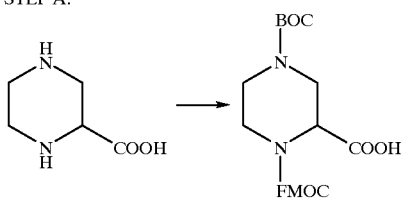

Dissolve 5.25 g (25.85 mmol) of 2-piperazine carboxylic acid.2HCl in 160 mL of 1:1 dioxane/$H_2O$, and adjust the pH to 11 with 50% NaOH (aq.). Slowly add (in portions) a solution of 7.21 g (29.28 mmol) of BOC-ON in 40 mL of 1:1 dioxane/$H_2O$ while maintaining the pH at 11 with 50% NaOH (aq.) during the addition. Stir at room temperature for 5 hours, then cool to 0° C. and adjust to pH 9.5 with 50% NaOH(aq.). Slowly add (in portions) a solution of 7.34 g (28.37 mmol) of FMOC-Cl in 40 mL of dioxane, maintaining a pH of 9.5 during the addition with 50% NaOH (aq.). Warm the mixture to room temperature and stir for 20 hours. Wash with $Et_2O$ (3×150 mL), adjust to pH=2–3 with 6N HCl (aq), and extract with toluene (3×150 mL). Dry the combined extracts over $Na_2SO_4$ and concentrate in vacuo to a volume of 150 mL. Chill at −20° C. overnight, filter to collect the resulting solids, wash with hexane and dry the solids in vacuo to give 5.4 g of the product compound.

STEP B:

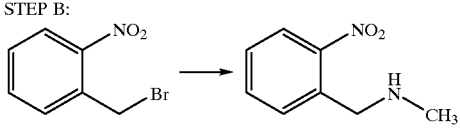

Slowly add 2.0 g (9.26 mmol) of 2-nitrobenzylbromide to 37 mL of a 2 M solution of $CH_3NH_2$ in THF, then stir at room temperature for 16 hours. Dilute with 200 mL of EtOAc, wash with water (3×60 mL), then dry the organic phase over $Na_2SO_4$ and concentrate in vacuo to give 1.53 g of the product compound.

STEP C:

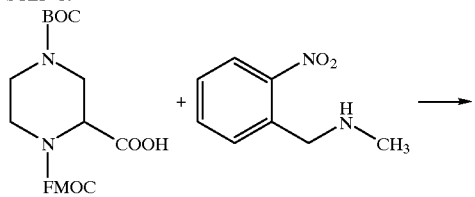

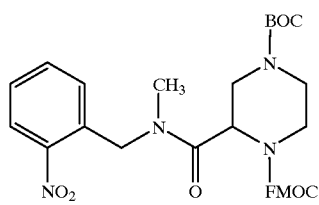

Combine 2.74 g (6.05 mmol) of the product of Step A, 4.22 mL of Hünigs base, 2.76 g (7.26 mmol) of HATU, and a solution of 1.00 g (6.05 mmol) of the Product of Step B in 25 mL of $CH_2Cl_2$, and stir at room temperature for 16 hours. Dilute with 75 mL of EtOAc wash successively with 10% HCl (aqueous) (2×40 mL), saturated $NaHCO_3$ (aqueous) (2×40 mL) and 40 mL of brine. Dry the organic phase over $MgSO_4$ concentrate in vacuo to a residue and chromatograph (silica gel, 2% MeOH/$CH_2Cl_2$) to give 2.71 g of the product compound.

STEP D:

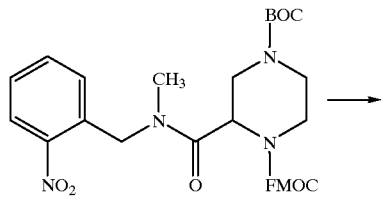

Combine 1.00 g (1.67 mmol) of the Product of Step C, 8 mL of DMF and 0.18 mL (1.83 mmol) of piperidine, and stir at room temperature for 4 hours. Concentrate in vacuo to a residue and chromatograph (silica gel, 4% MeOH/$CH_2Cl_2$) to give 0.34 g of the product compound.

STEP E:

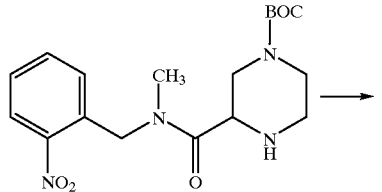

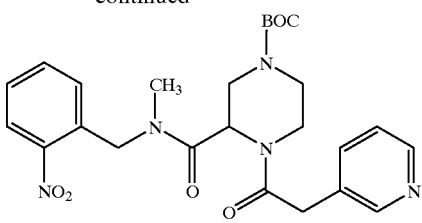

Combine 0.30 g (0.789 mmol) of the Product of Step D and 8 mL of $CH_2Cl_2$, then add 0.164 g (0.947 mmol) of 3-pyridylacetic acid.HCl, 0.116 g (0.947 mmol) of DMAP and 0.195 g (0.947 mmol) of DCC, and stir at room temperature for 16 hours. Chromatograph (silica gel, 4% MeOH/$CH_2Cl_2$) to give 0.37 g of the Product compound.

STEP F:

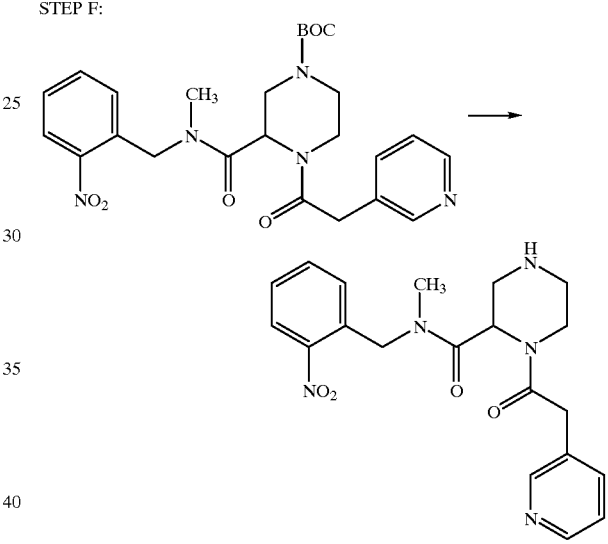

Add 0.5 mL of TFA to a solution of 0.25 g (0.502 mmol) of the Product of Step E in 5 mL of $CH_2Cl_2$, and stir at room temperature for 4 hours. Concentrate in vacuo to a residue, add 60 mL of EtOAc and wash successively with saturated $K_2CO_3$ (aqueous) (2×20 mL) and 30 mL of brine. Dry the organic phase over $Na_2SO_4$ and concentrate in vacuo to give 0.170 g of the Product compound.

STEP G:

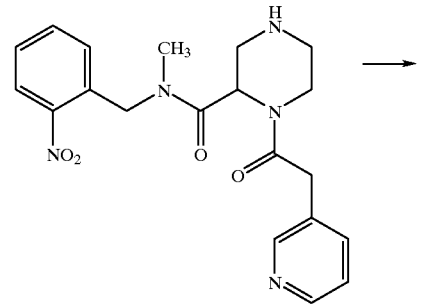

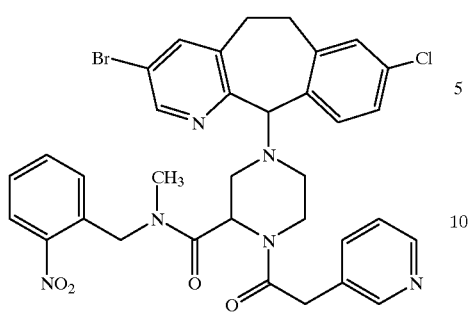

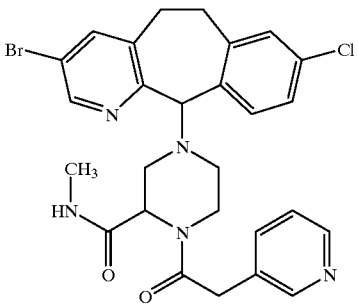

Example 32-A

Combine 0.096 g (0.242 mmol) of the product of Step F, 0.083 g (0.242 mmol) of the chloride Product of Preparative Example 40, Step B, of WO 95/10516, and 1 mL of THF, then 0.037 g (0.242 mmol) of DBU, and heat at 60° C. for 6 hours. Concentrate in vacuo to a residue and chromatograph (silica gel, 2% to 5% MeOH/CH$_2$Cl$_2$) to give 0.035 g of the title compound (Example 32) along with 0.042 g of a product of formula:

Analytical data for Example 32: $^1$H NMR (CDCl$_3$): 2.01–3.08 (m, 9H); 3.55–3.86 (m, 4H); 3.90–4.10 (m, 2H); 4.21–4.38 (m, 2H); 5.23–5.39 (m, 2H); 7.09–7.31 (m, 5H); 7.44 (t, 1 H); 7.52.7.70 (m, 3H); 8.09 (br. d, 1 H); 8.37–8.52 (m, 3H).

Analytical data for Example 32-A: $^1$H NMR (CDCl$_3$): 1.85–2.21 (m, 3H); 2.44–2.86 (m, 5H); 3.01–3.46 (m, 3H); 3.52–4.50 (m, 5H); 5.01 (br. s, 1H); 5.48–5.68 (m, 1 H); 7.07–7.99 (m, 3H); 7.24–7.31 (br. s, 1 H); 7.55–7.65 (m, 2H); 8.32–8.57 (m, 3H).

Using substantially the same procedure as described for Example 32, Steps A–G, but substituting the indicated amine for CH$_3$NH$_2$ in Step B, and or the indicated acid for 3-pyridylacetic acid in Step E, the following compounds were also prepared:

| Reagents used in Step B and/or Step E | Compound |
|---|---|
| Step B: i-propyl-amine | 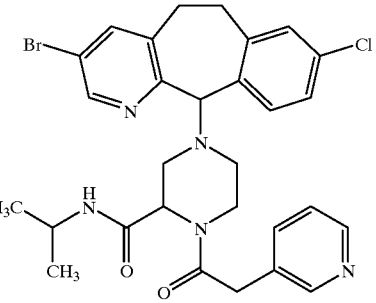<br>Example 32-B |
| Step B: i-propyl-amine<br>Step E: 4-pyridyl-acetic acid | 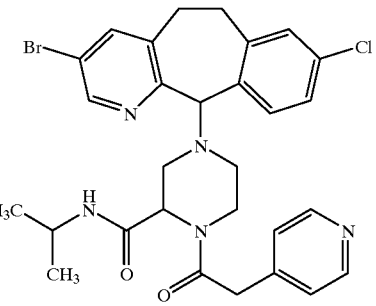<br>Example 32-C |

Analytical data for Example 32-B: $^1$H NMR (CDCl$_3$): 0.9–1.07 (m, 6H); 1.80–2.23 (m, 2H); 2.36–2.89 (m, 3H); 2.97–3.38 (m, 2H); 3.47–4.10 (m, 5H); 4.08–4.18 (m, 1H); 4.41 (br. d, 1H one diastereoisomer); 4.90 (br. s, 1H one diastereoisomer); 5.17–5.25 and 5.60–5.65 (m, 2H); 7.00–7.13 (m, 3H); 7.16–7.23 (br. s, 1H); 7.50–7.60 (m, 2H); 8.27–8.49 (m, 3H).

Analytical data for Example 32-C: $^1$H NMR (CDCl$_3$): 0.98–1.11 (m, 6H); 1.82–2.21 (m, 2H); 2.40–2.82 (m, 3H); 3.10 (t, 1H); 3.17–3.40 (m, 1H); 3.50–3.62 (m, 1H); 3.70–4.32 (m, 5H); 4.49 (br. d, 1H one diastereoisomer); 4.98 (br. s, 1H one diastereoisomer); 5.20–5.36 and 5.61–5.69 (m, 2H); 7.05–7.20 (m, 5H); 7.54–7.62 (m, 1H); 8.32–8.38 (m, 1H); 8.52–8.59 (m, 2H).

EXAMPLE 33

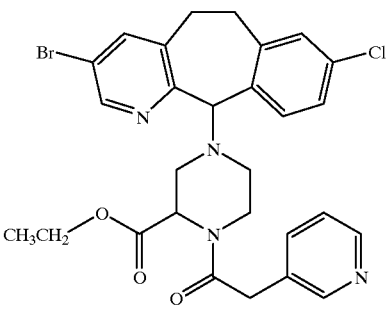

STEP A:

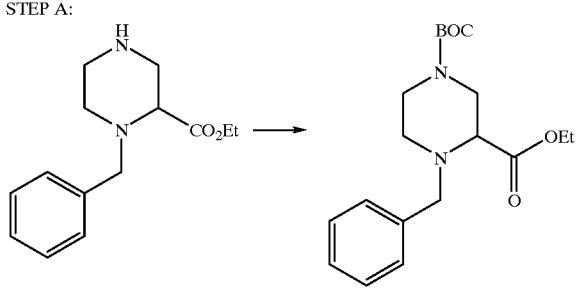

Combine 12.05 g (48.5 mmol) of ethyl 1-N-benzyl-2-piperazinecarboxylate in 100 mL of THF with 10.59 g (48.5 mmol) of di-t-butyl-dicarbonate and stir at room temperature for 3 hours. Concentrate in vacuo to give 17.17 g of the product compound.

STEP B:

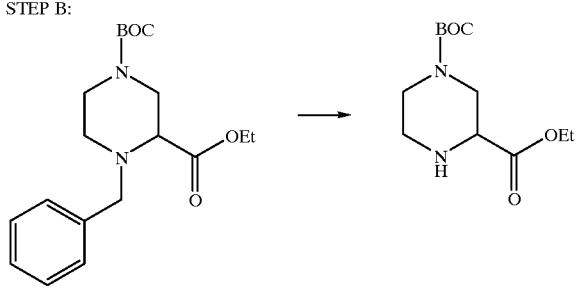

Combine 17.17 g of the product compound from Step A, 150 mL of MeOH, 7.5 mL of HOAc and 3.4 g of 10% Pd/C, and hydrogenate with H$_2$ (50 psi) for 18 hours at room temperature. Filter through celite®, wash the filter cake with MeOH and concentrate the filtrates in vacuo to a residue. Dissolve the residue in 300 mL of EtOAc and wash successively with saturated Na$_2$CO$_3$ (aqueous) (2×150 mL) and 100 mL of brine. Dry over MgSO4 and concentrate in vacuo to give 11.54 g of the product compound.

STEP C:

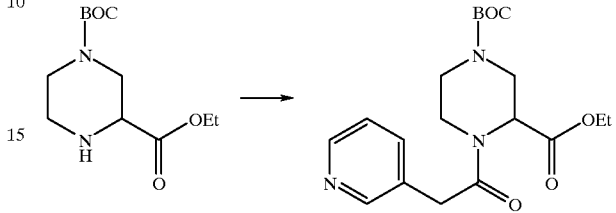

Combine 0.26 g (1 mmol) of the product compound from Step B, 1 mL of CH$_2$Cl$_2$, 0.174 g (1 mmol) of 3-pyridylacetic acid, 0.147 g (1.2 mmol) of DMAP and 0.248 g (1.2 mmol) of DCC, and stir at room temperature for 40 hours. Concentrate in vacuo to a residue and chromatograph (silica gel, 5% MeOH/CH$_2$Cl$_2$) to give 0.315 g of the product compound.

STEP D:

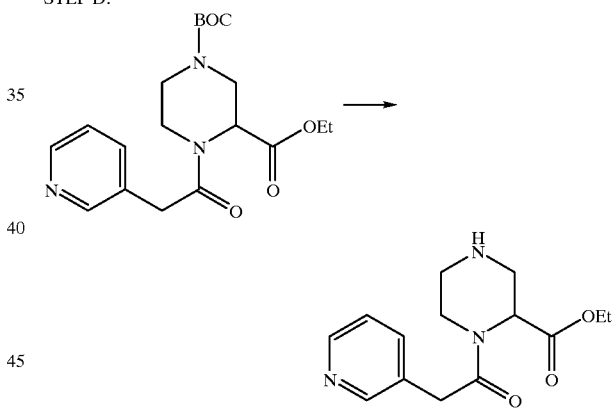

Combine 0.196 g (0.521 mmol) of the product compound from Step C and 0.5 mL of TFA, and stir at room temperature for 40 hours. Concentrate in vacuo to a residue, add 50 mL of EtOAc and wash with 10 mL of 1 N Na$_2$CO$_3$ (aqueous). Dry over Na$_2$SO$_4$ and concentrate in vacuo to give 0.077 g of the product compound.

STEP E:

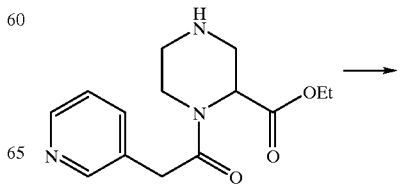

115

-continued

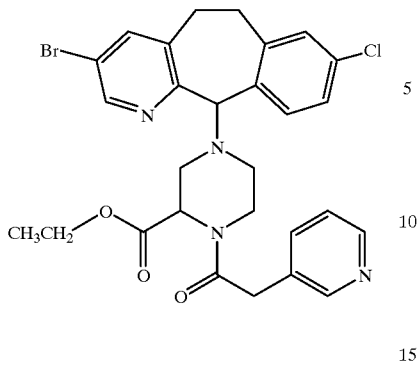

Combine 0.075 g (0.272 mmol) of the product compound from Step D, 0.091 g (0.265 mmol) of the chloride Product of Preparative Example 40, Step B, of WO 95/10516, 2 mL of THF and 0.40 g (0.265 mmol) of DBU, and stir at 50° C. for 24 hours. Cool to 25° C., concentrate in vacuo to a residue, and chromatograph (silica gel, 5% MeOH/CH$_2$Cl$_2$) to give 0.034 g of the product compound. $^1$H NMR (CDCl$_3$): 1.12 and 1.14 (t, 3H); 1.55–1.82 (m, 1H); 1,92–2,50 2H); 2.53–2.81 (m, 2H); 3.03–3.25 (m, 1H); 3.28–3.45 (m, 1H); 3.53–3.71 (m, 2H); 3.74 (s, 2H); 3.85–4.19 (m, 3H); 4.31 and 4.32 (s, 1H); 5.10–5.18 (m,3H).

EXAMPLE 34

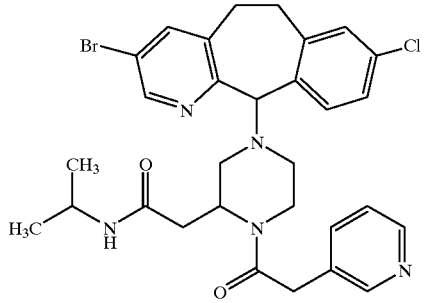

STEP A:

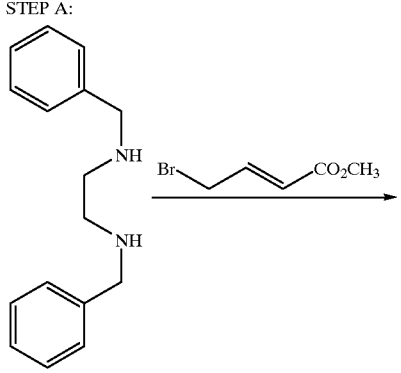

116

-continued

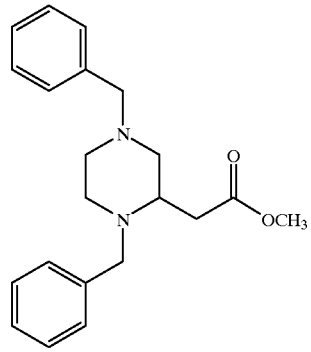

Combine 12 mL (50 mmol) of N,N'-dibenzylethylenediamine, 14 mL (100 mmol) of Et$_3$N and 250 mL toluene at 0° C., add 7 mL (50 mmol) of methyl 4-bromocrotonate (7 mL, 50 mmol), slowly warm to room temperature and stir for 24 hours. Filter, concentrate the filtrate in vacuo to a residue and treat with 10% aqueous HCl (300 mL). Filter again and wash the filtrate EtOAc (2×100 mL). Basify the filtrate with K$_2$CO$_3$, extract with EtOAc (3×150 mL), wash the combined extracts with brine, dry over MgSO$_4$ and concentrate in vacuo to give 13.7 g of the product compound. $^1$H NMR (CDCl$_3$) 2.28–2.50 (m, 4H), 2.5–2.75 (m, 4H), 3.1 (bs, 1H), 3.42 (d, 2H), 3.52 (d, 1H), 3.6 (s, 3H), 3.75 (dd 1H), 7.15–7.35 (m, 10H).

STEP B:

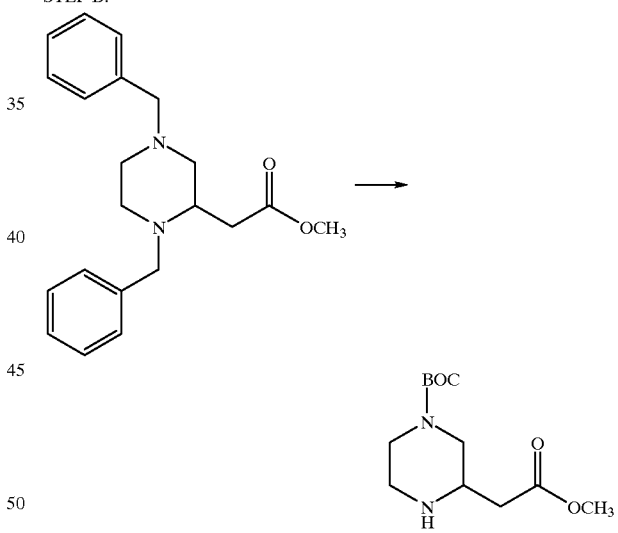

Combine 13.7 g (40 mmol) of the product of Step A, 150 mL of MeOH, 50 mL of 1 N HCl (aqueous) and 3 g of 10% Pd/C and hydrogenate with H$_2$ (50 psi) for 24 hours. Filter, concentrate the filtrate in vacuo to remove most of the MeOH, and basify with K$_2$CO$_3$ to pH=9–10. Slowly add 9.8 g (40 mmol) of BOC-ON at 0° C. and stir at 0° for 1 hour. Slowly warm up to room temperature, stir 2 hours, and extract with EtOAc (2×200 mL). Treat the combined extracts with 50 mL of 10% HCl (aqueous), wash the aqueous layer with EtOAc, basify with K$_2$CO$_3$ and extract three times with EtOAc. Wash the combined organic layers with brine, dry over MgSO$_4$ and concentrate in vacuo to give 7.89 g of the product compound. $^1$H NMR (CDCl$_3$): 1.4 (s, 9H), 2.31 (dd, 1H), 2.37 (dd, 1H), 2.55 (b, 1H), 2.69–3.02 (m. 4H), 3.75 (s, 3H), 3.88 (b, 2H).

STEP C:

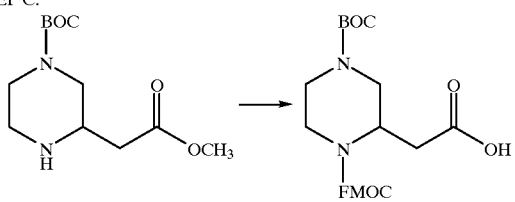

Combine 5.2 g (20 mmol) of the product of Step B, 60 mL of THF, 60 mL of 1 N NaOH (aqueous) and stir at room temperature for 6 hours. Cool to 0° C., add 10% HCl (aqueous) to adjust to pH=9–10, then add 5.2 g (20 mmol) of FMOC-Cl. Stir at room temperature for 6 hours, (adding 1 N NaOH (aqueous) to maintain pH=9–10), then acidify with 10% HCl to pH=1. Extract twice, wash the combined organic layers with brine, dry over $MgSO_4$ and concentrate in vacuo to give 8.56 g of the product compound. $^1$H NMR ($CDCl_3$): 1.4 (s, 9H), 2.5–3.0 (m, 5H), 3.9–4.2 (m, 6H), 4.5 (m, 1H), 7–25 (t, 4H), 7.32(t, 4H), 7.48(d, 4H), 7.75(d, 4H).

STEP D:

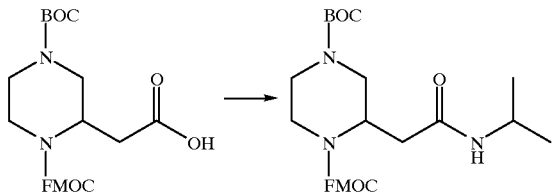

Combine 460 mg (1 mmol) of the product of Step C, 5 mL of $CH_2Cl_2$, 230 mg (1.2 mmol) of DEC and 130 μL (1.5 mmol) of i-propylamine, and stir at 25° C. for 6 hours. Treat with 10 mL of 1 N HCl (aqueous), extract with 30 mL of EtOAc, wash the extract with saturated $NaHCO_3$ (aqueous) and dry over $Na_2SO_4$. Concentrate in vacuo to give 454.6 mg of the product compound.

STEP E:

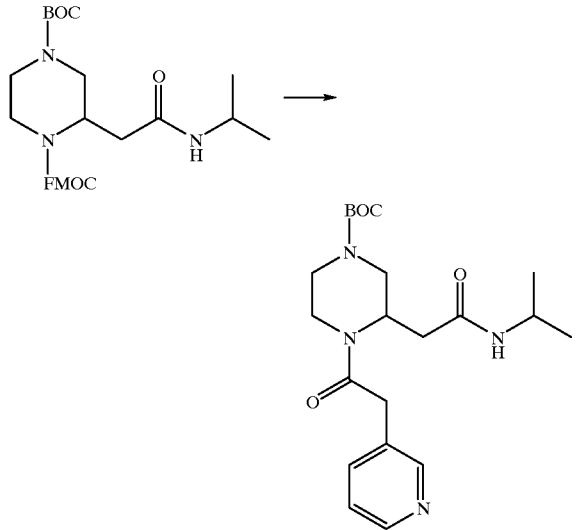

Combine a solution of 150 mg (0.3 mmol) of the product of Step D in DMF with 142 mg (0.45 mmol) of TBAF, and stir at 25° C. for 0.5 hours. Treat with 5 mL of 1 N HCl (aqueous) and wash with 10 mL of EtOAc. Basify with saturated $K_2CO_3$, extract three times with EtOAc and dry the combined extracts over $MgSO_4$. Concentrate in vacuo to a residue. Treat the residue with 3-pyridylacetic acid via substantially the same procedure as described for Example 33, Step C, to give 106.2 mg of the product compound.

STEP F:

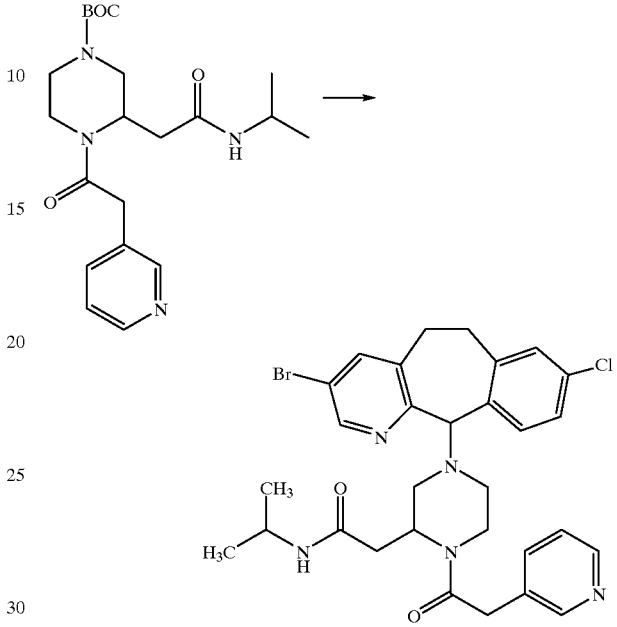

Combine 40 mg (0.1 mmol) of the product of Step E, 2 mL of $CH_2Cl_2$ and 1 mL of TFA, and stir at 25° C. for 0.5 hours. Concentrate in vacuo to a residue. Combine the residue with 90 μL (0.6 mmol) of DBU in 2 mL of THF, add 40 mg (0.12 mmol) of the product of Preparative Example 40, Step B, of WO 95/10516, and stir at 60° C. for 8 hours. Concentrate in vacuo to a residue and chromatograph to give 48.2 mg of the product compound.

EXAMPLE 36

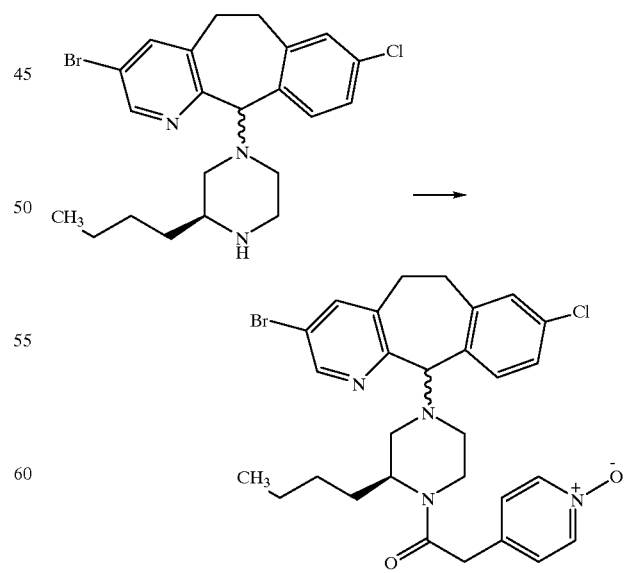

The title compound from Example 3B above (1 equivalent) (0.5 g.) was reacted with the title compound from Preparative Example 10B (1.5 equivalents) (0.2559 g.) and DEC (1.5 equivalents) (0.3203 g.), HOBT (1.5 equivalents) (0.169 g.) and N-methylmorpholine (1.5 equivalents) (0.245 ml.) in dry DMF (15 ml.) at 25° C. for 22 h. The reaction was worked up essentially as described in Example 20A and the product was purified on a silica gel column using 2.25% (10% concentrated ammonium hydroxide in methanol)-methylene chloride as the eluant to give the title compound. Yield: 609.4 mg., MH+ 585.0.

CMR data ($\delta_c$ (CDCl$_3$)) for the title compound: (1) tricyclic: (a) CH$_2$: 29.7/29.8/29.9/30.0/30.2/30.4, (b) CH: 146.6/146.7, 140.6/140.9, 132.1, 129.8/129.9/130.0/130.1, 125.9, 78.3/78.4/78.5, and (c) C: 119.6, 140.2/140.4, 134.6, 136.2/136.3, 136.4, 154.6/154.7/154.9/155.0; (2) piperazine: (a) CH$_3$: 13.5/13.6, (b) CH$_2$: 22.0/22.1, 28.7, 27.6/27.9, 37.0/37.1/38.0/38.5, 41.4/41.5, 50.8/51.6, 53.1/53.2/53.5/53.8/53.9, and (c) CH: 49.0; and (3) piperazine N-substituent: (a) CH$_2$: 51.2, (b) CH: 126.3, 126.3,138.5, 138.5, and (c) C: 133.8,166.4/166.7.

EXAMPLE 37

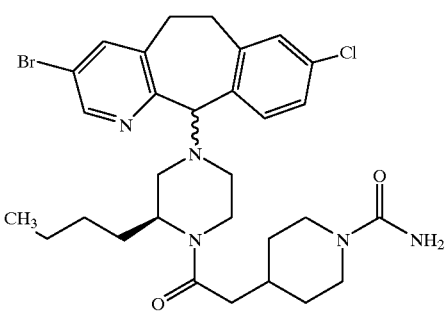

STEP A:

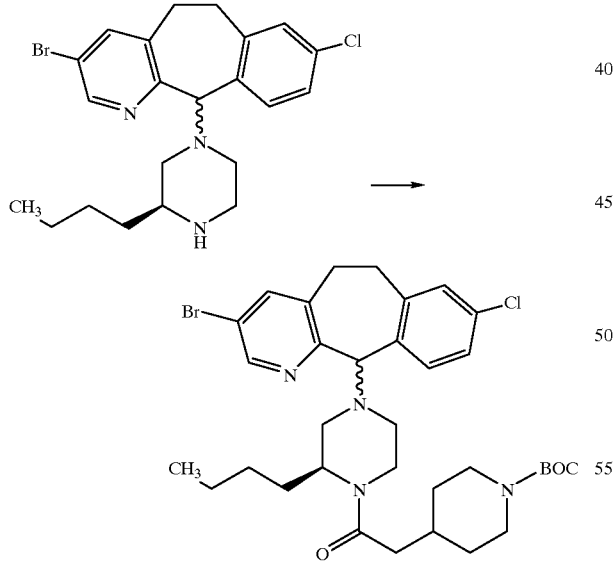

The title compound from Example 3B above (1 equivalent) (0.658 g.) was reacted with the title compound from Preparative Example 17D, of WO 95/10516, (1.3 equivalents) (0.4637 g.) and DEC (1.3 equivalents) (0.3654 g.), HOBT (1.3 equivalents) (0.2575 g.) and N-methylmorpholine (1.3 equivalents) (0.21 ml.) in dry DMF (25 ml.) at 25° C. for 25 h. The product was isolated as described in Example 20A and used directly in Step B below.

STEP B:

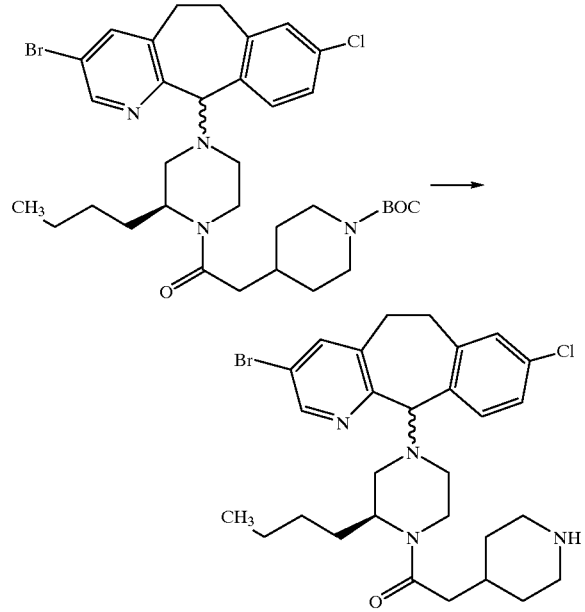

The title compound from Step A above was dissolved in methanol (5 ml.) and 10% (v/v) concentrated sulfuric acid in dioxane (15 ml.) was added and the reaction was run and worked up as described in Example 20B to give the title compound. Yield: 0.312 g., MH+ 575.4.

STEP C:

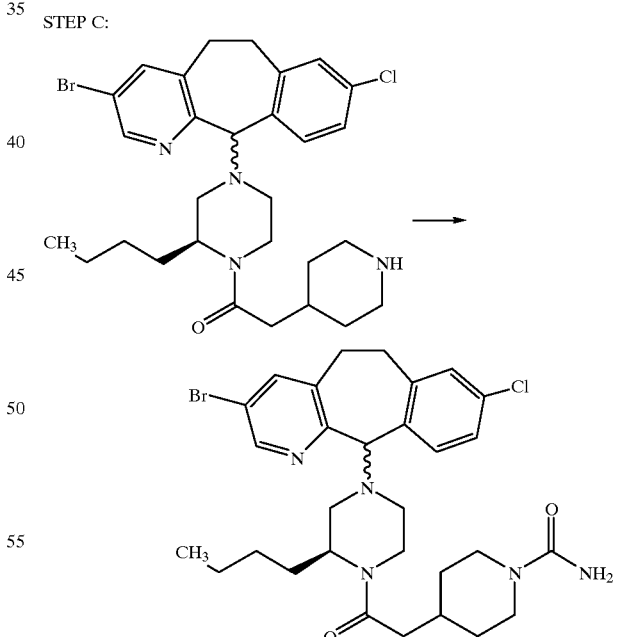

The title compound from Step B above (1 equivalent) (0.310 g. ) was dissolved in dry methylene chloride (5 ml.) and trimethylsilylisocyanate (6 equivalents) (0.3733 g.) (0.439 ml.) was added. The mixture was stirred at 25° C. for 77 h. under argon. Additional trimethylsilylisocyanate (6 equivalents) (0.3733 g.) (0.439 ml.) was added and the reaction was allowed to proceed for a total of 106 h. The mixture was diluted with methylene chloride and washed with saturated aqueous sodium bicarbonate, water and then dried over magnesium sulfate. Filtration followed by evaporation gave the title compound that was purified on a silica gel column using 2%(10% concentrated ammonium hydroxide in methanol)-methylene chloride as the eluant to give the title compound. Yield: 0.1758 g., MH+ 618.2.

CMR data ($\delta_c$ (CDCl$_3$))for the title compound: (1) tricyclic: (a) CH$_2$: 29.8, 30.1, (b) CH: 146.6/146.7, 140.8/140.9, 132.1, 125.8/125.9, 128.9/129.9/130.0/130.1, 78.5/78.6, and (c) C: 119.6, 140.2/140.4, 133.7/133.8, 134.7/134.8, 136.2/136.3, 155.0/155.7; (2) piperazine: (a) CH$_3$: 13.5/13.6, (b) CH$_2$: 40.9/41.0, 51.1/51.4/51.9, 53.2/53.3/53.4/53.9/54.2, 36.5, 22.1/22.2, 27.7/27.8, and (c) CH: 48.8; and (3) piperazine N-substituent: (a) CH$_2$: 44.0, 31.5, 31.5, 44.0, 39.1, (b) CH: 32.6, and (c) C: 157.5, 169.1/169.4.

EXAMPLE 38

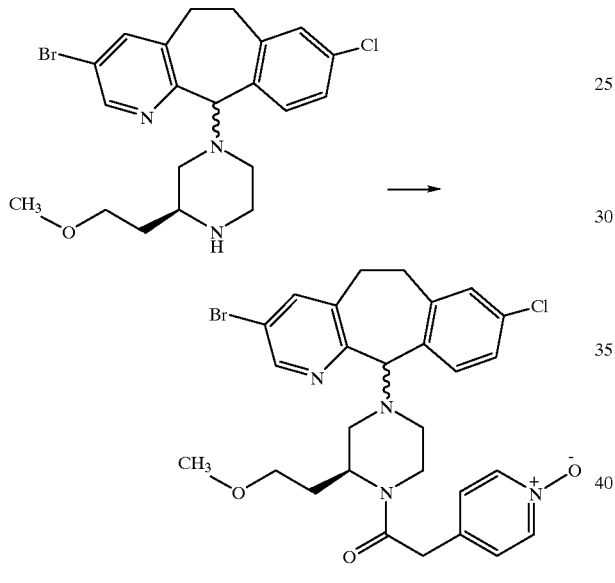

The title compound from Example 11B above (1 equivalent) (0.4 g.) was reacted with the title compound from Preparative Example 10B (1.5 equivalents) (0.2038 g.) and DEC (1.5 equivalents) (0.2552 g.), HOBT (1.5 equivalents) (0.1346 g.) and N-methylmorpholine (1.5 equivalents) (0.195 ml.) in dry DMF (15 ml.) at 25° C. for 17 h. The reaction was worked up essentially as described in Example 20A and the product was purified on a silica gel column using 3% (10% concentrated ammonium hydroxide in methanol)-methylene chloride as the eluant to give the title compound. Yield: 539.6 mg., MH+ 587.

CMR data ($\delta_c$ $_{(CDCl_3)}$)) for the title compound: (1) tricyclic: (a) CH$_2$: 29.8/30.0, 30.0/30.2, (b) CH: 146.6/146.7/146.8, 140.8,132.1/132.3, 129.9/130.0, 125.9/126.3, 78.4/78.5, and (c) C: 119.6, 140.2/140.3, 133.8, 134.3/134.4/134.6, 136.2/136.3, 154.6/154.8; (2) Piperazine: (a) CH$_3$: 58.2, (b) CH$_2$: 50.9/51.2/51.6, 54.3154.4/54.7, 37.4/37.6, 39.3142.3, 67.6/67.7/69.6, and (c) CH: 50.0; and (3) piperazine N-substituent: (a) CH$_2$: 36.6/36.8, (b) CH: 138.4/138.5, 126.4, 126.4, 138.4/138.5, and (c) C: 133.8.

EXAMPLE 39

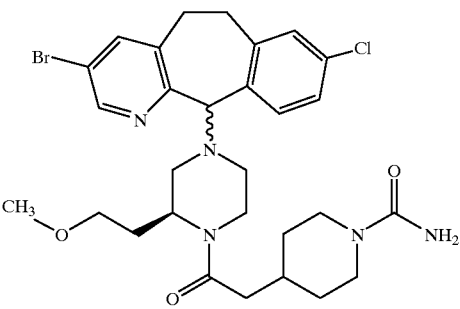

STEP A:

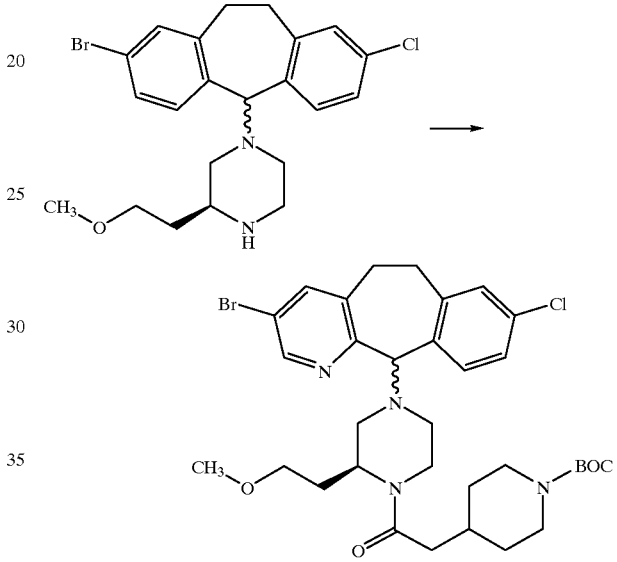

The title compound from Example 11B above (1 equivalent) (2.7 g.) was reacted with the title compound from Preparative Example 17D, of WO 95/10516, (1.3 equivalents) (1.89 g.) and DEC (1.3 equivalents) (1.49 g.), HOBT (1.3 equivalents) (1.05 g.) and N-methylmorpholine (1.3 equivalents) (0.7876 g.) (0.8561 ml.) in dry DMF (80 ml.) at 25° C. for 24 h. The product was isolated as described in Example 20A and chromatographed on a silica gel column using 0.5%(10% concentrated ammonium hydroxide in methanol)-methylene chloride as the eluant to give the title compound. Yield: 1.49 g., MH+ 677.

STEP B:

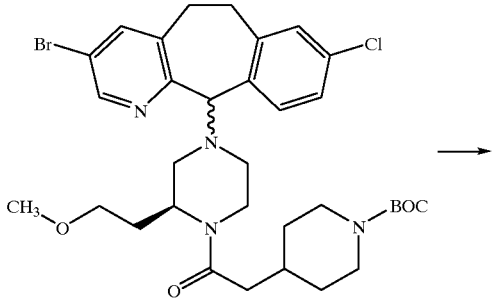

123

-continued

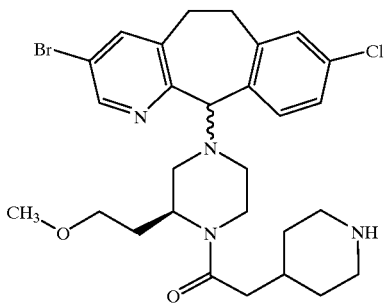

The title compound from Step A above (1.38 g.) was dissolved in methanol (10 ml.) and 10% (v/v) concentrated sulfuric acid in dioxane (30 ml.) was added and the reaction was run and worked up as described in Example 20B. The product was chromatographed on a silica gel column using 6–8%(10% concentrated ammonium hydroxide in methanol)-methylene chloride as the eluant to give the title compound. Yield: 0.7175 g., MH+ 577.

CMR data ($\delta_c$ (CDCl$_3$)) for the title compound: (1) tricyclic: (a) CH$_2$: 29.9/30.0, 30.1/30.2, (b) CH: 146.6/146.7, 140.7/140.8, 132.1/132.2, 125.8/125.9,129.9/130.0, 78.6, and (c) C: 119.5/119.6, 140.3/140.7, 133.7, 134.7/134.8, 136.2/136.4, 155.0/155.1; (2) piperazine: (a) CH$_3$: 58.1, (b) CH$_2$: 39.8/39.9/40.9, 51.3/51.5/51.9, 54.3/54.8/55.1, 36.2, 67.9/68.0/69.7/69.8, and (c) CH: 49.7/49.8; and (3) piperazine N-substituent: (a) CH$_2$: 45.9, 32.7, 32.7, 45.9, 39.0, (b) CH: 32.9; and (c) C: 169.7/170.2.

STEP C:

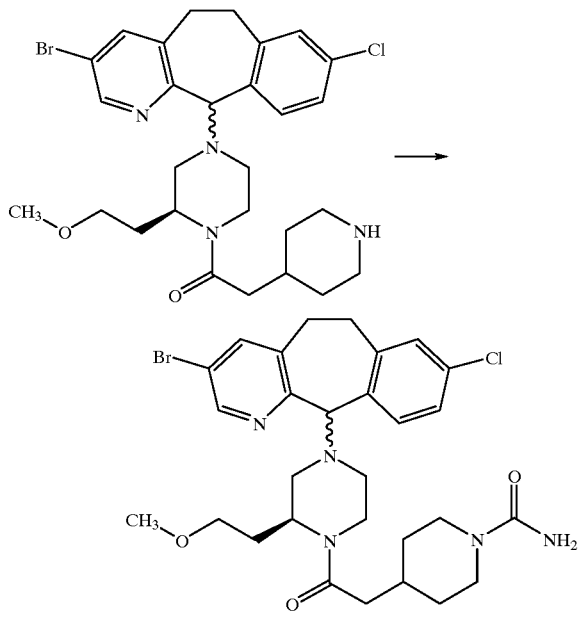

The title compound from Step B above (1 equivalent) (0.582 g.) was dissolved in dry methylene chloride (6 ml.) and trimethylsilylisocyanate (6 equivalents) (0.6985 g.) (0.821 ml.) was added. The mixture was stirred at 25° C. for 48 h. under argon. The mixture was diluted with methylene chloride and washed with saturated aqueous sodium bicarbonate, water and then dried over magnesium sulfate. Filtration followed by evaporation gave the title compound that was purified on a silica gel column using 3%(10% concentrated ammonium hydroxide in methanol)-methylene chloride as the eluant to give the title compound. Yield: 0.4926 g., MH+ 620.

CMR data ($\delta_c$ (CDCl$_3$)) for the title compound: (1) tricyclic: (a) CH$_2$: 29.9/30.0, 30.1, (b) CH: 146.6/146.7, 140.7/140.8, 132.1/132.2, 125.8/125.9, 130.0, 78.6, and (c) C: 119.5/119.6, 140.3, 133.8, 134.8, 136.2/136.4, 154.9/155.0; (2) piperazine: (a) CH$_3$: 58.1/58.2, (b) CH$_2$: 38.2/38.3, 51.2/51.5/51.8, 54.3/54.7/55.1, 36.2, 67.8167.9169.6169.8, and (c) CH: 49.7; and (3) piperazine N-substituent: (a) CH$_2$: 43.9/44.0, 40.8/40.9, 40.8/40.9, 43.9/44.0, 39.1, (b) CH: 32.5; and (c) C: 157.5, 169.3/169.9.

EXAMPLE 40

STEP A:

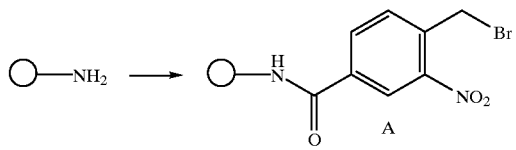

To a suspension of Tentagel® NH$_2$ Resin (Rapp Polymere Gmbh, Germany) (1.0 g, 0.28 mmol/g loading, 0.28 mmol) in DCM (10 mL) in a Merrifield reaction vessel was added 4-(bromomethyl)-3-nitrobenzoic acid (1.12 mmol, 0.29 g), HOBT (1.12 mmol, 0.15 g) and DIC (1.68 mmol, 0.21 g, 0.26 mL). The resin shook at room temperature for 16 h and was then washed with DCM (4×10 mL) and THF (3×10 mL).

STEP B

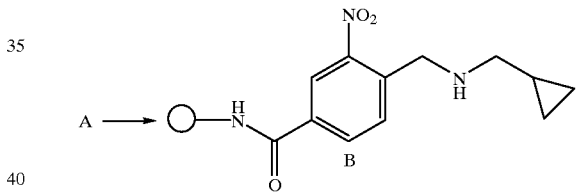

The resin (0.28 mmol theoretical loading) was suspended in THF (10 mL) and treated with (aminomethyl) cyclopropane (5.6 mmol, 0.40 g, 0.49 mL) at room temperature for 16 h. The resin was then washed with THF (2×10 mL).

STEP C:
B ⟶

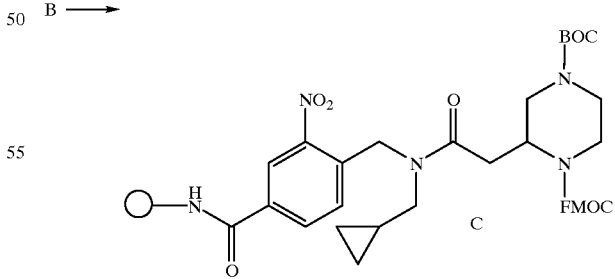

The resin (0.28 mmol theoretical loading) is suspended in DCM (10 mL) and reacted with 1-N-FMOC-4-BOC piperazine-2-acetic acid (1.12 mmol, 0.52 g), HATU (1.12 mmol, 0.43 g) and N,N-diisopropyethylamine (2.24 mmol, 0.29 g, 0.39 mL). The resin shook at room temperature for 16 h and was then washed with DCM (4×10 mL). The resin was then retreated with the same mixture of reagents in a second coupling cycle of 16 h. The resin was then washed with DCM (6×10 mL).

STEP D:

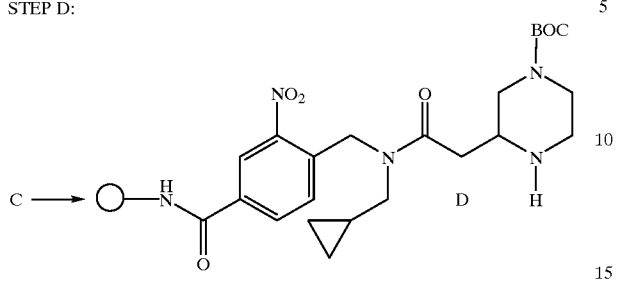

The resin (0.28 mmol theoretical loading) was washed once with DMF (10 mL) and was then treated with a 30% solution of piperidine in DMF (total volume=10 mL) at room temperature for 30 min. The resin was then washed with DMF (10 mL), methanol (2×10 mL) and DCM (3×10 mL).

STEP E:

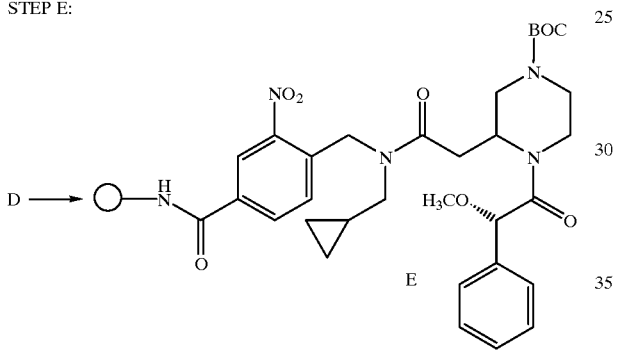

The resin (0.28 mmol theoretical loading) was suspended in DCM (10 mL) and treated with (S)-(+)-α-methoxyphenylacetic acid (1.12 mmol, 0.19 g), HATU (1.12 mmol, 0.43 g) and N,N-diisopropylethylamine (2.24 mmol, 0.29 g, 0.39 mL). The resin shook at room temperature for 16 h and was then washed with DCM (4×10 mL).

STEP F:

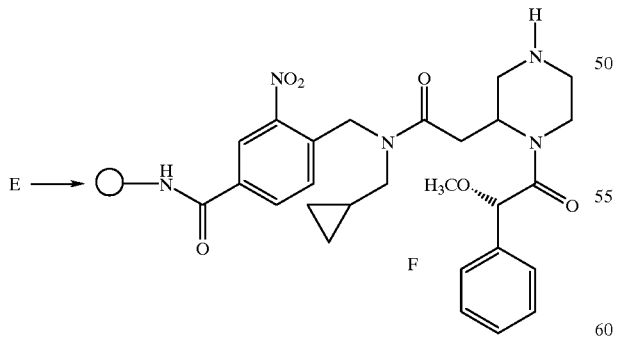

The resin (0.28 mmol theoretical loading) was treated with a 30% solution of TFA in DCM (10 mL) at room temperature for 1 h. The resin was then washed with DCM (2×10 mL) and methanol (3×10 mL) and then treated with a 20% solution of triethylamine in methanol (10 mL) for 30 min. The resin was then washed with methanol (2×10 mL) and DCM (4×10 mL).

STEP G:

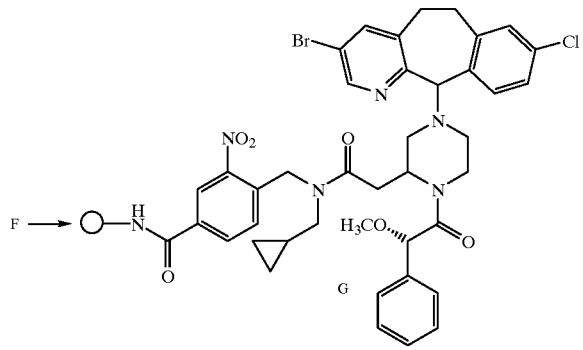

The resin (0.28 mmol theoretical loading) was suspended in DMA (10 mL) in a round-bottomed flask and treated with

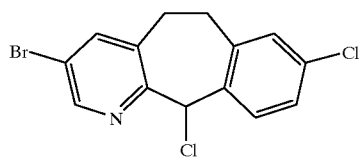

(1.12 mmol, 0.38 g), from Preparative Example 40 of WO 95/10516, and 1,2,2,6,6-pentamethylpiperidine (1.12 mmol, 0.17 g, 0.20 mL). The resin was stirred gently at 45° C. for 16 h and was then filtered and washed with DCM (5×10 mL), DMF (3×10 mL) and methanol (3×10 mL).

STEP H:

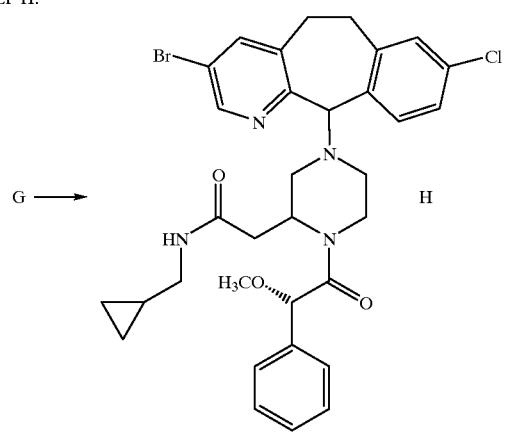

The resin (0.28 mmol theoretical loading) was washed from the filter funnel into a 25 mL round-bottomed flask with methanol (10 mL) and photolysed (UVP Blak-Ray lamp, 360 nm) for 3 h. The resin was filtered and washed with methanol (3×10 mL) and DCM (3×10 mL). The solvent and washings are combined and evaporated to dryness in vacuo giving compound H.

By employing the processes described above, as well as the processes described in WO 94/08051, as exemplified in Example 40, compounds of the formula:

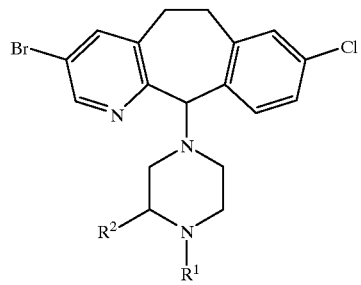

were prepared wherein R¹ and R² are defined in Table 3 below.

TABLE 3

| Example | R¹ | R² |
|---------|----|----|
| 41 | ![acetyl-piperidine-carboxamide] | ![N-butyl acetamide] |
| 42 | ![3-pyridyl acetone] | ![N-isopropyl propanamide] |
| 43 | ![phenyl butanone] | ![N-(3-pyridylmethyl) acetamide] |
| 44 | ![1-acetyl-4-acetoxy piperidine] | ![N-butyl acetamide] |
| 45 | ![3-pyridyl acetone] | ![N-methyl acetamide] |
| 46 | ![3-pyridyl acetone] | ![N-methyl propanamide] |
| 47 | ![4-pyridyl acetone] | ![N-cyclopropyl acetamide] |
| 48 | ![3-pyridyl acetone] | ![N-methyl-N-(2-nitrobenzyl) acetamide] |

TABLE 3-continued

| Example | R¹ | R² |
|---|---|---|
| 50 | pyridin-4-yl-CH₂-C(=O)- | -CH₂CH₂OH |
| 51 | pyridin-4-yl-CH₂-C(=O)- | -C(=O)CH₂CH₂-NH-CH₃ |
| 54 | pyridin-4-yl-CH₂-C(=O)- | -C(=O)CH₂CH₂-NH-cyclopropyl |
| 55 | pyridin-4-yl-CH₂-C(=O)- | -C(=O)CH₂-NH-CH(CH₃) |
| 56 | pyridin-4-yl-CH₂-C(=O)- | -C(=O)CH₂-N(CH₃)-CH(CH₃)₂ |

EXAMPLE 56A

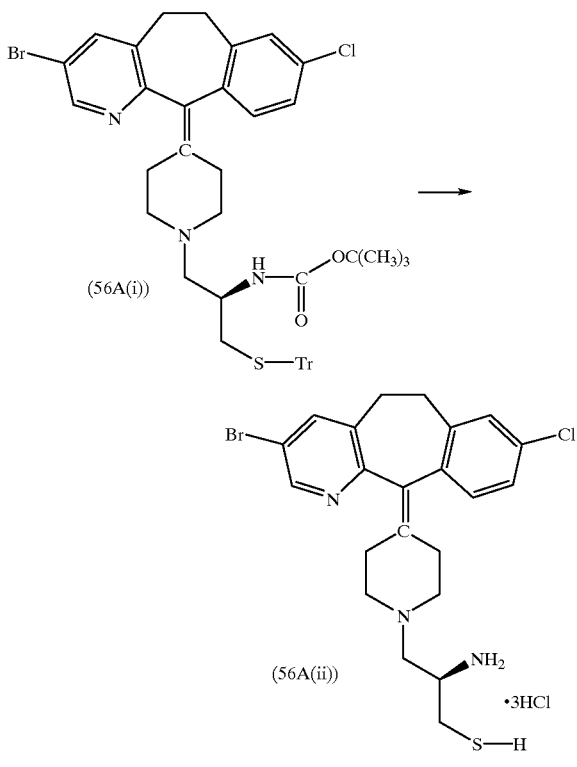

React the product of Preparative Example 2 following the procedure of Example 1 Step A to obtain Compound (56A (i)). Compound 56A(i) (320 mg), CH₂Cl₂ (2 mL), TFA (2 mL) and (C₂H₅)₃SiH (249 μL) were charged to a flask. The reaction mixture was stirred at room temperature for about three hours. All the solvents were removed on a rotavap. HCl (1N) was added to dissolve the product and the resulting solution was washed with hexanes. The solution was stripped down on a rotavap and then HCl (1 N) was added and the resulting solution was lyophilized to yield the title compound (56A(ii)). Mass Spec.: M+1=480.

The compounds in Tables 4–7 below exhibited biological activity at concentrations below about 10 μM using an in vitro assay measuring the inhibition of FPT. Under the test protocols employed, there were certain compounds within the scope of the invention which did not exhibit activity. It is believed that such compounds would exhibit activity under a different test protocol. For example, certain compounds wherein R¹ was:

(114.0)

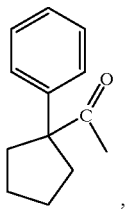

,

-continued (116.0)

[structure: 5-methoxyindole with -CH2-C(=O)- at 3-position]

(126.0)

[structure: (CH3)2CH-S(=O)2-CH3, isopropyl methyl sulfone type]

(130.0)

[structure: 2-naphthyl methyl sulfone]

(133.0)

[structure: 2-amino-thiazole with -C(=O)-C(=N-OCH3)- substituent]

(134.0)

[structure: imidazole-CH2-C(=O)-CH3]

(144.0)

[structure: furan-2-yl-C(=O)-C(=O)-CH3]

(162.0)

[structure: indole-3-yl-C(=O)-CH3], or

-continued (163.0)

[structure: indole with -CH2-C(=O)- at 3-position]

did not exhibit activity at the concentrations tested.

EXAMPLES 57–210

Compounds of the formula:

[structure: tricyclic compound with Br and Cl substituents, piperazine ring with R¹ and R² substituents]

were prepared, by procedures similar to those in Example 40, wherein R¹ and R² are defined in Table 4 below. In Table 4 the numbers in the column for R¹ refer to the formula numbers of the R¹ groups exemplified In Table 4, R² is —C(O)R⁶⁵ (i.e., formula (84.0)). The numbers in the R² column refer to the formula numbers of the R⁶⁵ groups exemplified In Table 4, the column labeled "EX" refers to the example number.

TABLE 4

| EX | R² (R⁶⁵) | R¹ | EX | R² (R⁶⁵) | R¹ | EX | R² (R⁶⁵) | R¹ |
|---|---|---|---|---|---|---|---|---|
| 57 | 201.0 | (S)-110.0 | 58 | 201.0 | 143.0 | 59 | 201.0 | 147.0 |
| 60 | 202.0 | 101.0 | 61 | 202.0 | 103.0 | 62 | 202.0 | 104.0 |
| 63 | 202.0 | 105.0 | 64 | 202.0 | 136.0 | 65 | 202.0 | 137.0 |
| 66 | 202.0 | 152.0 | 67 | 202.0 | 153.0 | 68 | 202.0 | 157.0 |
| 69 | 202.0 | 160.0 | 70 | 202.0 | 161.0 | 71 | 202.0 | 136.0 |
| 72 | 203.0 | 101.0 | 73 | 203.0 | 102.0 | 74 | 203.0 | 103.0 |
| 75 | 203.0 | 104.0 | 76 | 203.0 | 105.0 | 77 | 203.0 | 106.0 |
| 78 | 203.0 | (S)-110.0 | 79 | 203.0 | 113.0 | 80 | 203.0 | 118.0 |
| 81 | 203.0 | 120.0 | 82 | 203.0 | 124.0 | 83 | 203.0 | 125.0 |
| 84 | 203.0 | 137.0 | 85 | 203.0 | 143.0 | 86 | 203.0 | 152.0 |
| 87 | 203.0 | 153.0 | 88 | 203.0 | 154.0 | 89 | 203.0 | 156.0 |
| 90 | 203.0 | 157.0 | 91 | 203.0 | 160.0 | 92 | 203.0 | 161.0 |
| — | — | — | 94 | 204.0 | 101.0 | 95 | 204.0 | 102.0 |
| 96 | 204.0 | 103.0 | 97 | 204.0 | 104.0 | 98 | 204.0 | 105.0 |
| 99 | 204.0 | 106.0 | 100 | 204.0 | (R)-110.0 | 101 | 204.0 | 123.0 |
| 102 | 204.0 | 124.0 | 103 | 204.0 | 129.0 | 104 | 204.0 | 136.0 |
| 105 | 204.0 | 137.0 | 106 | 204.0 | 152.0 | 107 | 204.0 | 154.0 |
| 108 | 204.0 | 157.0 | — | — | — | — | — | — |
| 111 | 205.0 | 101.0 | 112 | 205.0 | 120.0 | 113 | 205.0 | 124.0 |
| 114 | 205.0 | 157.0 | 115 | 206.0 | 101.0 | 116 | 206.0 | 102.0 |
| 117 | 206.0 | 104.0 | 118 | 206.0 | 105.0 | 119 | 206.0 | 122.0 |
| 120 | 208.0 | 125.0 | 121 | 206.0 | 137.0 | 122 | 206.0 | 139.0 |
| 123 | 206.0 | 152.0 | 124 | 206.0 | 157.0 | — | — | — |
| 126 | 207.0 | 101.0 | 127 | 207.0 | 122.0 | 128 | 207.0 | 137.0 |
| 129 | 208.0 | 101.0 | 130 | 208.0 | 103.0 | 131 | 208.0 | 104.0 |
| 132 | 208.0 | 106.0 | 133 | 208.0 | 112.0 | 134 | 208.0 | 124.0 |

TABLE 4-continued

| EX | R² (R⁶⁵) | R¹ | EX | R² (R⁶⁵) | R¹ | EX | R² (R⁶⁵) | R¹ |
|---|---|---|---|---|---|---|---|---|
| 135 | 208.0 | 137.0 | 136 | 208.0 | 152.0 | 137 | 208.0 | 153.0 |
| 138 | 208.0 | 155.0 | 139 | 208.0 | 157.0 | 140 | 209.0 | 104.0 |
| 141 | 209.0 | 137.0 | 142 | 209.0 | 157.0 | 143 | 210.0 | 101.0 |
| 144 | 210.0 | 102.0 | 145 | 210.0 | 104.0 | 146 | 210.0 | 105.0 |
| 147 | 210.0 | 120.0 | 148 | 210.0 | 124.0 | 149 | 210.0 | 125.0 |
| 150 | 210.0 | 136.0 | 151 | 210.0 | 137.0 | 152 | 210.0 | 149.0 |
| 153 | 210.0 | 150.0 | 154 | 210.0 | 153.0 | 155 | 210.0 | 155.0 |
| 156 | 210.0 | 157.0 | 157 | 212.0 | 137.0 | 158 | 214.0 | 137.0 |
| 159 | 214.0 | 148.0 | 160 | 215.0 | 125.0 | 161 | 216.0 | 124.0 |
| 162 | 216.0 | 157.0 | 163 | (S)-217.0 | 101.0 | 164 | (S)-217.0 | 103.0 |
| 165 | (S)-217.0 | 107.0 | 166 | (S)-217.0 | 137.0 | 167 | (S)-217.0 | 138.0 |
| 168 | (S)-217.0 | 152.0 | 169 | (S)-217.0 | 157.0 | 170 | (S)-217.0 | 160.0 |
| — | — | — | 172 | (R)-217.0 | 122.0 | 173 | (R)-217.0 | 136.0 |
| 174 | (R)-217.0 | 137.0 | 175 | (R)-217.0 | 157.0 | 176 | (R)-217.0 | 161.0 |
| 177 | 219.0 | 147.0 | 178 | 220.0 | 157.0 | 179 | 221.0 | 117.0 |
| 180 | 223.0 | 124.0 | 181 | 225.0 | 101.0 | 182 | 225.0 | 102.0 |
| 183 | 225.0 | 103.0 | 184 | 225.0 | 105.0 | 185 | 225.0 | 106.0 |
| 186 | 225.0 | 107.0 | 187 | 225.0 | 108.0 | 188 | 225.0 | 109.0 |
| 189 | 225.0 | (R)-110.0 | 190 | 225.0 | (S)-110.0 | 191 | 225.0 | 112.0 |
| 192 | 225.0 | 113.0 | 193 | 225.0 | 119.0 | 194 | 225.0 | 120.0 |
| 195 | 225.0 | 136.0 | 196 | 225.0 | 137.0 | 197 | 225.0 | 151.0 |
| 198 | 225.0 | 152.0 | — | — | — | 200 | 226.0 | 106.0 |
| 202 | 227.0 | 108.0 | 202 | 227.0 | (R)-110.0 | 203 | 227.0 | 148.0 |
| — | — | — | 205 | 229.0 | 157.0 | 206 | 230.0 | 131.0 |
| 207 | 230.0 | 137.0 | 208 | 230.0 | 161.0 | 209 | 231.0 | 137.0 |
| 210 | 231.0 | 145.0 | 211 | 231.0 | 157.0 | — | — | — |

EXAMPLES 211–248

Compounds of the formula:

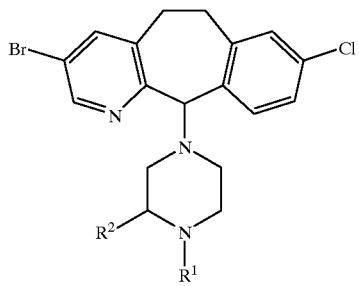

were prepared, by procedures similar to those in Example 40, wherein $R^1$ and $R^2$ are defined in Table 5 below. In Table 5 the numbers. in the column for $R^1$ refer to the formula numbers of the $R^1$ groups exemplified above. In Table 5 $R^2$ is —$CH_2C(O)R^{65}$ (i.e., formula (86.0)). The numbers in the $R^2$ column refer to the formula numbers of the $R^{65}$ groups exemplified above. In Table 5 the column labeled "EX" refers to the example number.

TABLE 5

| EX | R² (R⁶⁵) | R¹ | EX | R² (R⁶⁵) | R¹ | EX | R² (R⁶⁵) | R¹ |
|---|---|---|---|---|---|---|---|---|
| 211 | 202.0 | 105.0 | 212 | 202.0 | 120.0 | 213 | 202.0 | 140.0 |
| 214 | 202.0 | 157.0 | 215 | 203.0 | 102.0 | 216 | 203.0 | 104.0 |
| 217 | 203.0 | 120.0 | 218.0 | 203.0 | 124.0 | 219 | 203.0 | 137.0 |

TABLE 5-continued

| EX | R² (R⁶⁵) | R¹ | EX | R² (R⁶⁵) | R¹ | EX | R² (R⁶⁵) | R¹ |
|---|---|---|---|---|---|---|---|---|
| 220 | 203.0 | 138.0 | 221 | 203.0 | 140.0 | 222 | 203.0 | 153.0 |
| 223 | 203.0 | 156.0 | 224 | 205.0 | 138.0 | 225 | 205.0 | 152.0 |
| 226 | 205.0 | 157.0 | 227 | 205.0 | 161.0 | 228 | 207.0 | 158.0 |
| 229 | 208.0 | 120.0 | 230 | 208.0 | 146.0 | 231 | 208.0 | 157.0 |
| 232 | 209.0 | 150.0 | 233 | 209.0 | 161.0 | — | — | — |
| 235 | 211.0 | 120.0 | 236 | 213.0 | 147.0 | 237 | 214.0 | 139.0 |
| 238 | 216.0 | 101.0 | 239 | 216.0 | 132.0 | 240 | (S)-217.0 | 148.0 |
| 241 | (R)-217.0 | 102.0 | 242 | (R)-217.0 | 103.0 | 243 | 219.0 | 125.0 |
| 244 | 221.0 | 125.0 | — | — | — | 246 | 226.0 | 103.0 |
| 247 | 226.0 | 127.0 | 248 | 229.0 | 155.0 | — | — | — |

EXAMPLES 249–280

Compounds of the formula:

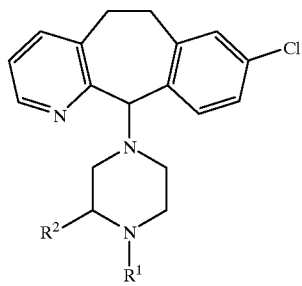

were prepared, by procedures similar to those in Example 40, wherein $R^1$ and $R^2$ are defined in Table 6 below. In Table 6 the numbers in the column for $R^1$ refer to the formula numbers of the $R^1$ groups exemplified above. In Table 6 $R^2$ is —$C(O)R^{65}$ (i.e., (84.0)). The numbers In the $R^2$ column refer to the formula numbers of the $R^{65}$ groups exemplified above. In Table 6 the column labeled "EX" refers to the example number.

TABLE 6

| EX | R² (R⁶⁵) | R¹ | EX | R² (R⁶⁵) | R¹ | EX | R² (R⁶⁵) | R¹ |
|---|---|---|---|---|---|---|---|---|
| 249 | 202.0 | 157.0 | 250 | 203.0 | 129.0 | 251 | 203.0 | 157.0 |
| 252 | 204.0 | 109.0 | 253 | 204.0 | 157.0 | 254 | 205.0 | 124.0 |
| 255 | 210.0 | 154.0 | 256 | 215.0 | 112.0 | 257 | (S)-217.0 | 106.0 |
| 258 | (R)-217.0 | 120.0 | 259 | (R)-217.0 | 143.0 | 260 | 219.0 | 106.0 |
| 261 | 219.0 | 115.0 | 262 | 221.0 | 146.0 | 263 | 222.0 | 108.0 |
| 264 | 222.0 | 132.0 | 265 | 222.0 | 151.0 | 266 | 225.0 | 101.0 |
| 267 | 225.0 | 102.0 | 268 | 225.0 | 103.0 | 269 | 225.0 | 104.0 |
| 270 | 225.0 | 106.0 | 271 | 225.0 | 108.0 | 272 | 225.0 | (R)-110.0 |
| 273 | 225.0 | 112.0 | 274 | 225.0 | 124.0 | 275 | 225.0 | 136.0 |
| 276 | 225.0 | 141.0 | 277 | 225.0 | 143.0 | 278 | 225.0 | 152.0 |
| 279 | 225.0 | 157.0 | 280.0 | 228.0 | 101.0 | — | — | — |

EXAMPLES 281–288

Compounds of the formula:

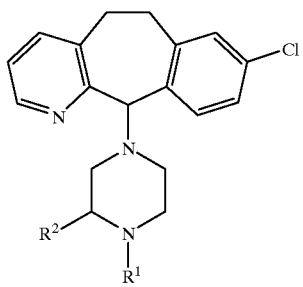

were prepared, by procedures similar to those in Example 40, wherein $R^1$ and $R^2$ are defined in Table 7 below. In Table 7 the numbers in the column for $R^1$ refer to the formula numbers of the $R^1$ groups exemplified above. In Table 7 $R^2$ is —$CH_2C(O)R^{65}$ (i.e., formula (86.0)). The numbers in the $R^2$ column refer to the formula numbers of the $R^{65}$ groups exemplified above. In Table 7 the column labeled "EX" refers to the example number.

TABLE 7

| EX | $R^2$ ($R^{65}$) | $R^1$ | EX | $R^2$ ($R^{65}$) | $R^1$ | EX | $R^2$ ($R^{65}$) | $R^1$ |
|---|---|---|---|---|---|---|---|---|
| 281 | 202.0 | 102.0 | 282 | 202.0 | 151.0 | 283 | 202.0 | 157.0 |
| 284 | 203.0 | 157.0 | 285 | 212.0 | 150.0 | 286 | (S)-217.0 | 105.0 |
| 287 | 221.0 | 159.0 | 288 | 223.0 | 149.0 | — | — | — |

EXAMPLES 289–306

Compounds of the formula:

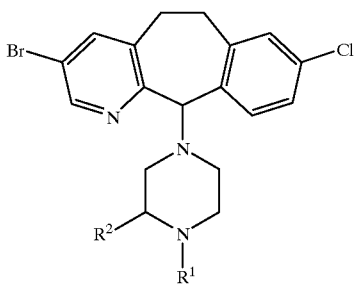

could be prepared, if procedures similar to those in Example 40, were to be followed, wherein $R^1$ and $R^2$ are defined in Table 8 below. In Table 8 the numbers in the column for $R^1$ refer to the formula numbers of the $R^1$ groups exemplified above. In Table 8 $R^2$ is —$C(O)R^{65}$ (i.e., (84.0)) or —$CH_2C(O)R^{65}$ (i.e., (86.0)). The numbers in the $R^2$ column refer to the formula numbers of the $R^{65}$ groups exemplified above. In Table 8 the column labeled "EX" refers to the example number.

TABLE 8

| EX | $R^2$ (—$C(O)R^{65}$) ($R^{65}$) | $R^2$ (—$CH_2C(O)R^{65}$) ($R^{65}$) | $R^1$ |
|---|---|---|---|
| 289 | 203.0 | — | 124.0 |
| 290 | 204.0 | — | 121.0 |
| 291 | 204.0 | — | 122.0 |
| 292 | 204.0 | — | 125.0 |
| 293 | 206.0 | — | 136.0 |
| 294 | 217.0 | — | 125.0 |
| 295 | 217.0 | — | 157.0 |
| 296 | 225.0 | — | 142.0 |
| 297 | 228.0 | — | 125.0 |
| 298 | 228.0 | — | 109.0 |
| 299 | — | 209.0 | 136.0 |
| 300 | — | 209.0 | 137.0 |
| 301 | — | 225.0 | 140.0 |
| 302 | — | 225.0 | 141.0 |

Assays

In some assays, FPT $IC_{50}$ (inhibition of farnesyl protein transferase, in vitro enzyme assay) is determined by the methods described in WO 95/10516. COS Cell $IC_{50}$ (Cell-Based Assay) and Cell Mat assay are determined by the methods described in WO 95/10516. GGPT $IC_{50}$ (geranylgeranyl protein transferase, in vitro enzyme assay) and in vitro tumor activity can be determined by the methods disclosed in WO 95/10516.

In some assays, the inhibition of farnesyl protein transferase was assayed by measuring the transfer of [$^3$H]farnesyl from [$^3$H]farnesylpsyrophosphate to biotinylated Ras-peptide (biotin-KKSKTKCVIM) using the conditions described below for each 96-well plate to be tested.

An assay buffer is prepared consisting of 40 mM Hepes, pH 7.5; 5 mM dithiothreitol; 20 mM magnesium chloride and 0.01 (v/v) % Igepal non-ionic detergent.

A SPA (scintillation proximity assay) bead suspension is prepared consisting of 50 mg of Streptavidin SPA beads (Amersham Life-Science) suspended in 2.5 mL of PBS (phosphate buffered saline). Immediately prior to running the assay a stop solution is prepared consisting of 480 μL of the SPA bead suspension mixed with 6720 μL of a solution consisting of 250 mM EDTA (pH 8.0) and 0.5% Bovine Serium Albumin (Fraction V, 96–99% albumin).

In some assays, to determine FPT $IC_{50}$, an assay mixture is prepared consisting of 480 μL of assay buffer and 3052.8 μL of water. This mixture is vortexed to homogeneity and 48 μL of the Ras peptide is added. The mixture is vortexed and 15.36 μL of FPP and 3.84 μL of [$^3$H]FPP are added and the mixture vortexed again. 37.5 μL of this assay mixture and 2.5 μL of a DMSO solution (at test concentration) of the compound being tested are then added to each well of a Costar polypropylene U-bottom microtiter plate. The plate is sonicated for 15 minutes at 37° C. and then shaken for 15 minutes on a plate shaker. 10 μL of the enzyme (recombinant Human famesyl protein transferase) is added to each well using a Beckman Biomek 2000. The plate is incubated at room temperature for 20 minutes and then quenched with 75 μL of the stop solution. 100 μL of the quenched reaction mixture from each well is then transferred to a Wallac crosstalk-free microtiter plate using a Beckman Biomek 2000. Radioactivity is measured in a Wallac 1450 Microbeta plus liquid scintillation counter. Percent inhibition is calculated relative to an uninhibited control.

In some assays, to determine famesyl transferase inhibition, an assay mixture is prepared consisting of 480 μL of assay buffer, 3052.8 μL of water and 240 μL of DMSO. This mixture is vortexed to homogeneity and 48 μL of the Ras peptide is added. The mixture is vortexed and 15.36 μL of FPP and 3.84 μL of [$^3$H]FPP are added and the mixture vortexed again. 40 μL of this assay mixture is then added to each well of a Costar polypropylene U-bottom microtiter plate, each well of which contains a dry sample of the compound being tested. The plate is sonicated for 15 minutes at 37° C. and then shaken for 15 minutes on a plate shaker. 10 μL of the enzyme (recombinant Human famesyl protein transferase) is added to each well using a Beckman Biomek 2000. The plate is incubated at room temperature for 20 minutes and then quenched with 75 μL of the stop solution. 100 μL of the quenched reaction mixture from each well is then transferred to a Wallac crosstalk-free microtiter plate using a Beckman Biomek 2000. Radioactivity is measured in a Wallac 1450 Microbeta plus liquid scintillation counter. Percent inhibition is calculated relative to an uninhibited control.

| Compound Tested | FPT Inhibition $IC_{50}$ in μM | Activity in COS Cells Inhibition of RAS Processing $IC_{50}$ in μM | Cell Growth Inhibition MAT Assay | |
|---|---|---|---|---|
| | | | Tumor Cells $IC_{50}$ in μM | Normal Cells $IC_{50}$ in μM |
| EX 1 | 19% @ 10 μM | — | — | — |
| EX 20, Step B | 2 | — | — | — |
| EX 21, Step B | 2.1 | — | — | — |
| EX 30 | 3.05 | 0 | >50 | >50 |
| EX 31 | 6.39 | 0 | 12.5 | 18 |
| EX 32-A | 0.440 0.500 | — | — | — |
| EX 32-B | 0.840 0.930 | — | — | — |
| EX 32-C | 0.210 0.340 | — | — | — |
| EX 33 | 0.870 1.2 | — | — | — |
| EX 34 | 2.5 2.3 | — | — | — |
| EX 36 | 0.060 | 0.63 | 1.6 | >25 |
| EX 37, Step C | 0.092 | 1.7 | 3.1 | 18 |
| Ex 38 | 0.034 | <0.25 | — | — |
| EX 39, Step B | 0.069 | — | — | — |
| EX 39, Step C | 0.027 | 0.600 | <1.6 | >25 |
| EX 41 | 0.077 | — | — | — |
| EX 43 | 0.035 0.021 | — | — | — |
| EX 44 | 4.1 8.0 | — | — | — |
| EX 46 | 0.900 1.4 | — | — | — |
| EX 47 | 0.170 | — | — | — |
| EX 48 | >10 20 | — | — | — |
| EX 50 | 9.0 13 | — | — | — |
| EX 51 | 0.330 0.380 | — | — | — |
| EX 54 | 0.068 | — | — | — |
| EX 55 | 0.600 | — | — | — |
| EX 56 | 0.240 0.160 | — | — | — |
| EX 56A | 18% @ 10.2 μM | — | — | — |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula

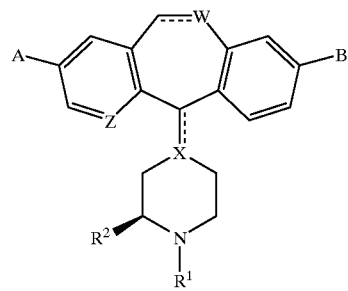

(1.0)

wherein:

A and B are independently selected from H, halo or $C_1$–$C_6$ alkyl;

Z is N or CH;

W is CH, $CH_2$, O or S, wherein the dotted line to W represents a double bond which is present when W is CH;

X is C, CH or N, wherein the dotted line connecting X to the tricyclic ring system represents a double bond which is present when X is C;

$R^1$ is selected from:

1) a group of the formula:

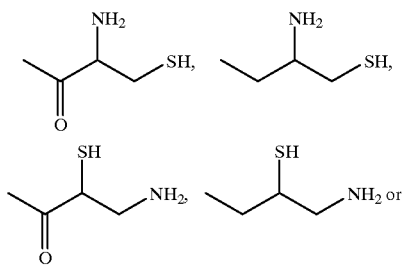

disulfide dimers thereof;

2) a group of the formula:

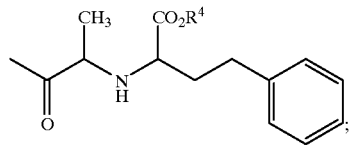

3) a group of the formula:

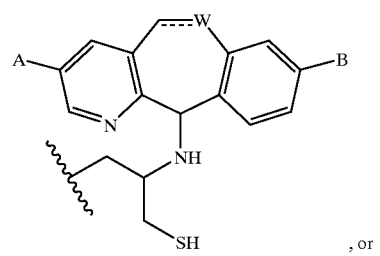

, or

-continued

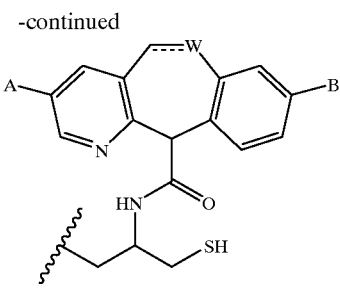

wherein W, A and B are as defined above;
4) a group of the formula:

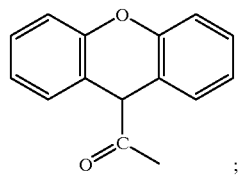

(159.0)

5) a group of the formula:

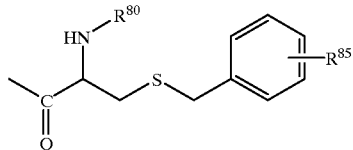

wherein $R^{80}$ is selected from H or —C(O)OR$^{90}$ wherein $R^{90}$ is a $C_1$–$C_6$ alkyl group, and $R^{85}$ is a $C_1$–$C_6$ alkoxy group; and
6) a group of the formula:

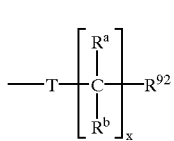

(82.0)

wherein:
(a) T is selected from:

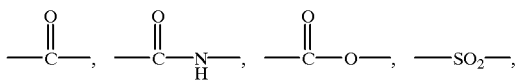

or a single bond;
(b) x is 0, 1, 2, 3, 4, 5 or 6;
(c) each $R^a$ and each $R^b$ is independently selected from H, aryl, alkyl, alkoxy, aralkyl, amino, alkylamino, heterocyloalkyl, —COOR$^{60}$, —NH{C(O)}$_z$R$^{60}$ (wherein z is 0 or 1), or —(CH)$_w$S(O)$_m$R$^{60}$ (wherein w is 0, 1, 2 or 3, and m is 0, 1 or 2); or $R^a$ and $R^b$ taken together can represent cycloalkyl, =N—O-alkyl, =O or heterocycloalkyl with the proviso that for the same carbon, $R^a$ is not selected from alkoxy, amino, alkylamino or —NH{C(O)}$_z$R$^{60}$ when $R^b$ is selected from alkoxy, amino, alkylamino or —NH{C(O)}$_z$R$^{60}$; and with the proviso that when T is a single bond, for the first carbon containing $R^a$ and $R^b$, $R^a$ and $R^b$ are not selected from alkoxy, alkylamino, amino or —NHR$^{60}$; and (d) $R^{92}$ can represent H, alkyl, aryl, aryloxy, arylthio, aralkoxy, aralkyl, heteroaryl or heterocycloalkyl;

$R^{60}$ represents H, alkyl, aryl or aralkyl;

$R^4$ is H or $C_1$–$C_6$ alkyl;

$R^2$ is selected from: —C(O)OR$^6$, $C_2$–$C_8$ alkynyl, substituted ($C_2$–$C_8$)alkenyl, substituted ($C_2$–$C_8$)alkynyl, wherein said substituted groups have one or more substituents selected from:
1) aryl, arylalkyl, heteroarylalkyl, heteroaryl, heterocycloalkyl, B-substituted aryl, B-substituted arylalkyl, B-substituted heteroarylalkyl, B-substituted heteroaryl or B-substituted heterocycloalkyl, wherein B is selected from $C_1$–$C_4$ alkyl, —(CH$_2$)$_n$OR$^6$, —(CH$_2$)$_n$NR$^6$R$^7$ and halo;
2) $C_3$–$C_6$ cycloalkyl;
3) —OR$^6$;
4) —SH or —S(O)$_t$R$^6$;
5) —NR$^6$R$^7$;
6) —N(R$^6$)—C(O)R$^7$;
7) —N(R$^6$)—C(O)NR$^7$R$^{12}$;
8) —O—C(O)NR$^6$R$^7$;
9) —O—C(O)OR$^6$;
10) —SO$_2$NR$^6$R$^7$;
11) —N(R$^6$)—SO$_2$—R$^7$; and
(12) —C(O)OR$^6$;

$R^6$, $R^7$ and $R^{12}$ are independently selected from H, $C_1$–$C_4$ alkyl, ($C_3$–$C_6$) cycloalkyl, aryl, arylalkyl, heteroaryl, heteroarylalkyl, heterocycloalkyl, substituted ($C_1$–$C_4$) alkyl, substituted ($C_3$–C6)cycloalkyl, substituted aryl, substituted arylalkyl, substituted heteroaryl, substituted heteroarylalkyl or substituted heterocycloalkyl, wherein said substituted groups have one or more substituents selected from: $C_1$–$C_4$ alkoxy, aralkyl, heteroarylalkyl, —NO$_2$, $C_3$–$C_{10}$-alkoxyalkoxy, $C_3$–$C_6$ cycloalkyl, aryl, —CN, nitrophenyl, methylenedioxyphenyl, heteroaryl, heterocycloalkyl, halo, —OH, —C(O)R$^{14}$, —C(O)NR$^6$R$^7$, —N(R$^6$)C(O)R$^{14}$, —S(O)$_t$R$^{14}$ or —NR$^{95}$R$^{15}$; provided that $R^6$, $R^7$ and $R^{12}$ are not CH$_2$OH or —CH$_2$NR$^{95}$R$^{15}$ when said $R^6$, $R^7$ or $R^{12}$ is directly bonded to a heteroatom, and further provided that $R^6$ is not H for groups 4) and 9), and $R^7$ is not H for group 6);

optionally, when $R^6$ and $R^7$ are bound to the same nitrogen, $R^6$ and $R^7$ together with the nitrogen to which they are bound, form a 5 to 7 membered heterocycloalkyl ring which optionally contains O, NR$^6$, or S(O)$_t$ wherein t is 0, 1 or 2;

optionally, when $R^7$ and $R^{12}$ are bound to the same nitrogen, $R^7$ and $R^{12}$ together with the nitrogen to which they are bound, form a 5 to 7 membered heterocycloalkyl ring which optionally contains O, NR$^6$, or S(O)$_t$ wherein t is 0, 1 or 2;

$R^{95}$ and $R^{15}$ are independently H, $C_1$–$C_4$ alkyl or aralkyl;

$R^{14}$ is $C_1$–$C_4$ alkyl, aryl or arylalkyl;

n=0, 1, 2, 3 or 4; and t=0, 1 or 2;

or pharmaceutically acceptable salts thereof.

2. A compound selected from:

(Example 36)
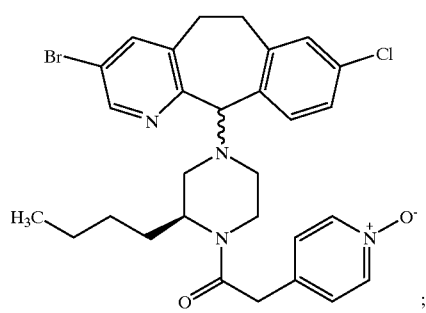
;

(Example 37)
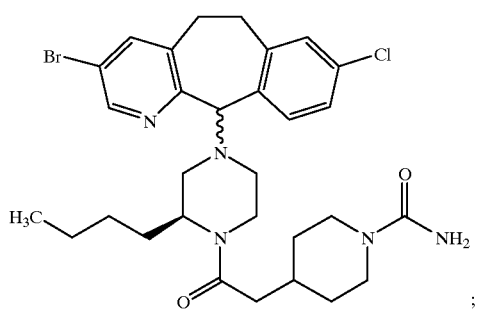
;

(Example 38)
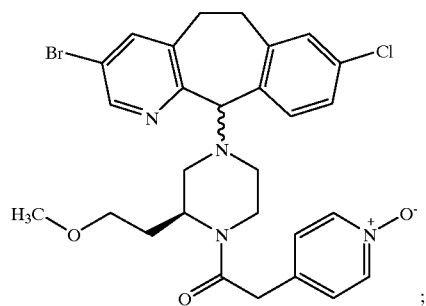
;

(Example 39 Step B)
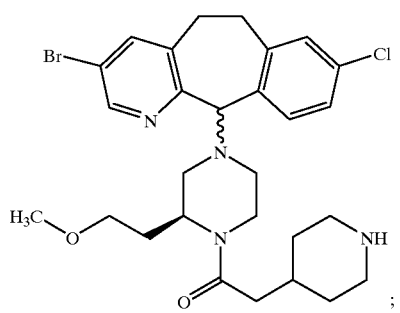
;

(Example 39 Step C)
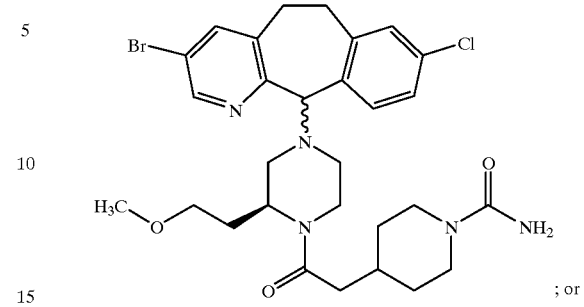
; or (Example 50)
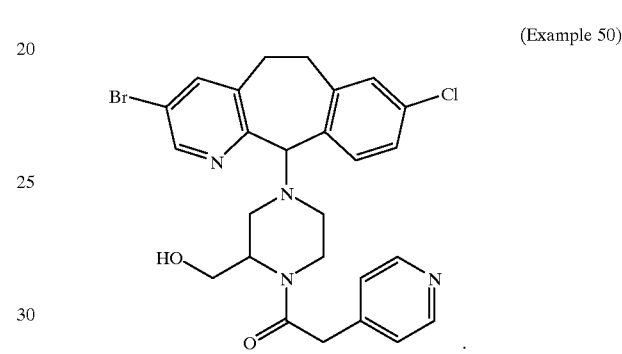
.

3. A method for inhibiting the abnormal growth of cells comprising administering an effective amount of a compound of claim 1.

4. The method of claim 3 wherein the cells inhibited are tumor cells expressing an activated ras oncogene.

5. The method of claim 4 wherein the cells inhibited are pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells.

6. The method of claim 4 wherein the inhibition of the abnormal growth of cells occurs by the inhibition of farnesyl protein transferase.

7. The method of claim 3 wherein the inhibition is of tumor cells wherein the Ras protein is activated as a result of oncogenic mutation in genes other than the Ras gene.

8. A pharmaceutical composition for inhibiting the abnormal growth of cells comprising an effective amount of compound of claim 1 in combination with a pharmaceutically acceptable carrier.

* * * * *